United States Patent
Hiramatsu et al.

(10) Patent No.: US 11,355,833 B2
(45) Date of Patent: Jun. 7, 2022

(54) WIRELESS COMMUNICATION DEVICE AND COMMUNICATION SYSTEM

(71) Applicant: KYOCERA Corporation, Kyoto (JP)

(72) Inventors: Nobuki Hiramatsu, Yokohama (JP); Hiroshi Uchimura, Kagoshima (JP); Masato Fujishiro, Yokohama (JP); Hiroshi Yamasaki, Yokohama (JP); Shotaro Sugita, Maibara (JP); Takahiro Watanabe, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 77 days.

(21) Appl. No.: 16/963,815

(22) PCT Filed: Nov. 2, 2018

(86) PCT No.: PCT/JP2018/040906
§ 371 (c)(1),
(2) Date: Jul. 21, 2020

(87) PCT Pub. No.: WO2019/142445
PCT Pub. Date: Jul. 25, 2019

(65) Prior Publication Data
US 2021/0057803 A1  Feb. 25, 2021

(30) Foreign Application Priority Data

Jan. 22, 2018  (JP) .............................. JP2018-008419

(51) Int. Cl.
*H01Q 1/27* (2006.01)
*H01Q 1/24* (2006.01)
(Continued)

(52) U.S. Cl.
CPC ............... *H01Q 1/273* (2013.01); *A61B 5/00* (2013.01); *H01Q 1/24* (2013.01); *H01Q 1/36* (2013.01); *H01Q 1/44* (2013.01); *H01Q 13/08* (2013.01)

(58) Field of Classification Search
CPC ............ H01Q 1/27; H01Q 1/273; H01Q 1/36; H01Q 1/24; H01Q 1/243; H01Q 1/44; H01Q 13/08
See application file for complete search history.

(56) References Cited

U.S. PATENT DOCUMENTS 6,567,053 B1 * 5/2003 Yablonovitch ......... H01Q 13/12
343/700 MS
9,653,785 B2 * 5/2017 Vance .................... A61B 5/681
(Continued)

FOREIGN PATENT DOCUMENTS

GB  2067842 A * 7/1981 ........... H01Q 19/005
JP  201155036 A  3/2011
(Continued)

OTHER PUBLICATIONS

Thijs Castel et al., "Reliable communication between rescuers during interventions using textile antenna systems", 2015 IEEE 20th International Workshop on Computer Aided Modelling and Design of Communication Links and Networks (CAMED), Sep. 7, 2015, pp. 135-139, 5pp.
(Continued)

*Primary Examiner* — Thai Pham
(74) *Attorney, Agent, or Firm* — Hauptman Ham, LLP

(57) ABSTRACT

According to an aspect, a wireless communication device is wearable on a living body. The wireless communication device includes an antenna and an attachment. The antenna has a first conductor, a second conductor, at least one third conductor, a fourth conductor, and a feeding line. The first conductor and the second conductor are opposed to each
(Continued)

other in a first axis. The third conductor is positioned between the first conductor and the second conductor. The third conductor extends in the first axis. The fourth conductor extends in the first axis. The feeding line is electromagnetically connected to any one of at least one third conductor. The first conductor and the second conductor are capacitively connected to each other through the third conductor. The attachment allows the fourth conductor to be opposed to the living body.

14 Claims, 101 Drawing Sheets

(51) Int. Cl.
    *H01Q 1/44*     (2006.01)
    *A61B 5/00*     (2006.01)
    *H01Q 1/36*     (2006.01)
    *H01Q 13/08*     (2006.01)

(56) References Cited

U.S. PATENT DOCUMENTS

| | | |
|---|---|---|
| 2014/0203987 A1 | 7/2014 | Itoh et al. |
| 2014/0226844 A1* | 8/2014 | Kerselaers ............ H01Q 1/273 |
| | | 381/315 |
| 2016/0380340 A1* | 12/2016 | Inoue ..................... H01Q 1/48 |
| | | 343/702 |
| 2017/0339479 A1 | 11/2017 | Levine |
| 2017/0374447 A1 | 12/2017 | Baum |

FOREIGN PATENT DOCUMENTS

| | | |
|---|---|---|
| JP | 2014523163 A | 9/2014 |
| JP | 201528754 A | 2/2015 |
| WO | 2009041497 A1 | 4/2009 |
| WO | 2015182016 A1 | 12/2015 |

OTHER PUBLICATIONS

Yasutaka Murakami et al., Low-Profile Design and Bandwidth Characteristics of Artificial Magnetic Conductor with Dielectric Substrate, 2015, pp. 172-179, vol. J98-B, No. 2, IEEE, Japan, 9pp.

Yasutaka Murakami et al., Optimum Configuration of Reflector for Dipole Antenna with AMC Reflector, 2015, pp. 1212-1220, vol. 98-B, No. 11, IEEE, 10pp.

* cited by examiner

WIRELESS COMMUNICATION DEVICE AND COMMUNICATION SYSTEM

CROSS REFERENCE TO RELATED APPLICATIONS

This application is a National Stage of PCT international application Ser. No. PCT/JP2018/040906 filed on Nov. 2, 2018 which designates the United States, incorporated herein by reference, and which is based upon and claims the benefit of priority from Japanese Patent Application No. 2018-008419 filed on Jan. 22, 2018, the entire contents of which are incorporated herein by reference.

FIELD

The present disclosure relates to a wireless communication device and a communication system.

BACKGROUND

Conventionally, there are wireless communication techniques using an antenna proximate to a living body, such as a wireless earphone. The living body has a water content of about 60% and thus can be considered as a conductive body and as a dielectric body. When a living body is considered as a conductive body, a technique as follows is known. Electromagnetic waves emitted from an antenna are reflected by a conductive body. The electromagnetic wave reflected by the conductive body is phase-shifted by 180°. The reflected electromagnetic wave is synthesized with the electromagnetic wave emitted from the antenna. The electromagnetic wave emitted from the antenna may have the amplitude reduced due to the synthesis with the phase-shifted electromagnetic wave. Consequently, the amplitude of the electromagnetic wave emitted from the antenna becomes smaller. The distance between the antenna and the conductive body is set to ¼ of the wavelength $\lambda$ of the emitted electromagnetic wave, whereby the effect by the reflected wave is reduced.

In comparison, a technique that reduces the effect by the reflected wave using an artificial magnetic conductor has been proposed. This technique is described in, for example, Non Patent Literatures 1 and 2.

CITATION LIST

Non Patent Literatures

Non Patent Literature 1: Murakami et al., "Low-Profile Design and Bandwidth Characteristics of Artificial Magnetic Conductor with Dielectric Substrate" IEICE trans. B, Vol. J98-B No. 2, pp. 172-179

Non Patent Literature 2: Murakami et al., "Optimum Configuration of Reflector for Dipole Antenna with AMC Reflector" IEICE trans. B, Vol. J98-B No. 11, pp. 1212-1220

SUMMARY

According to an aspect of the present disclosure, a wireless communication device wearable on a living body, includes: an antenna including a first conductor and a second conductor opposed to each other in a first axis, at least one third conductor positioned between the first conductor and the second conductor and extending in the first axis, a fourth conductor connected to the first conductor and the second conductor and extending in the first axis, and a feeding line electromagnetically connected to any one of the at least one third conductor, the first conductor and the second conductor being capacitively connected to each other through the third conductor; and an attachment configured to allow the fourth conductor to be opposed to the living body.

According to an aspect of the present disclosure, a communication system includes: a first wireless communication device; and a second wireless communication device, the first wireless communication device including: a tenth antenna including an eleventh conductor and a twelfth conductor opposed to each other in an eleventh axis, at least one thirteenth conductor positioned between the eleventh conductor and the twelfth conductor and extending in the eleventh axis, a fourteenth conductor connected to the eleventh conductor and the twelfth conductor and extending in the eleventh axis, and a tenth feeding line electromagnetically connected to any one of the at least one thirteenth conductor, the eleventh conductor and the twelfth conductor being capacitively connected to each other through the thirteenth conductor; and a tenth attachment configured to attach the tenth antenna to a living body such that the eleventh axis is oriented in a circumferential direction of an axis of a wearing part of the living body, the second wireless communication device including: a twentieth antenna including a twenty-first conductor and a twenty-second conductor opposed to each other in a twenty-first axis, at least one twenty-third conductor positioned between the twenty-first conductor and the twenty-second conductor and extending in the twenty-first axis, a twenty-fourth conductor connected to the twenty-first conductor and the twenty-second conductor and extending in the twenty-first axis, and a twentieth feeding line electromagnetically connected to any one of the at least one twenty-third conductor, the twenty-first conductor and the twenty-second conductor being capacitively connected to each other through the twenty-third conductor; and a twentieth attachment configured to attach the twentieth antenna to the living body such that the twenty-first axis is oriented in the circumferential direction of the axis of the wearing part.

DESCRIPTION OF EMBODIMENTS

Figure 89:
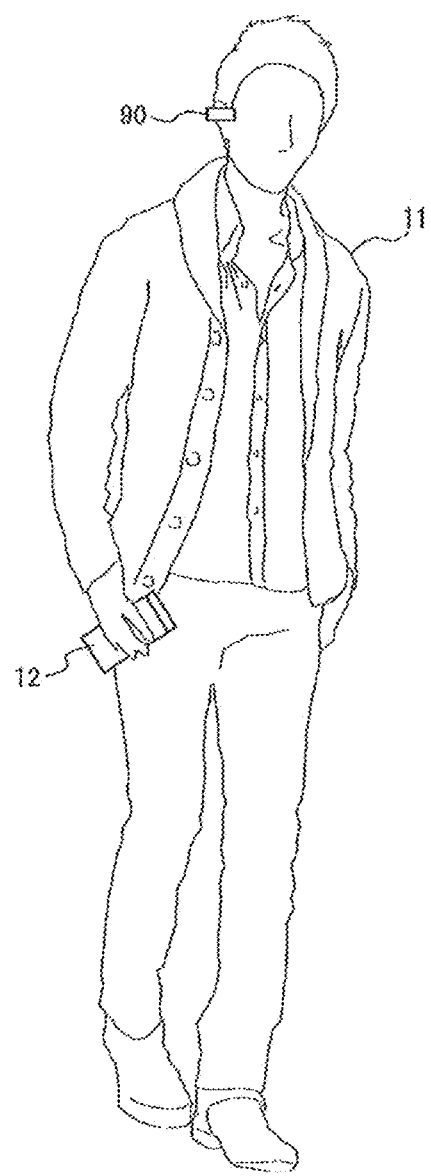
FIG. 89 is a diagram illustrating a usage manner of a wireless communication device according to an embodiment.

FIG. 89 is a diagram illustrating a usage manner of a wireless communication device according to an embodiment of the present disclosure. A wireless communication device 90 is worn on a living body 11 and used. The living body 11 is, for example, a human body. The living body 11 may be, for example, a pet animal and a livestock animal. The wireless communication device 90 may be worn on a variety of wearing parts of the living body 11. The parts wearing the wireless communication device 90 of the living body 11 may be, for example, head, arm, torso, leg, and finger.

The wireless communication device 90 has an antenna as described later and wirelessly communicates with an electronic device 12 around the wireless communication device 90. The wireless communication device 90 is, for example, an earphone and worn on the head of the living body 11 to be used. The electronic device 12 may be, for example, a multi-function terminal and a music player and communicates sound as a signal with the wireless communication device 90. The electronic device 12 may be, for example, a wireless communication base station. The wireless communication device 90 may be a hearing aid, a biological data acquisition system, a bearable data acquisition system, a headset, a headphone, and an animal monitoring device.

The antenna included in the wireless communication device 90 has an artificial magnetic conductor character as described later. Because of this character, the antenna can reduce the effect of a conductive body during emission of electromagnetic waves, even when worn on a conductive body such as a living body 11. Because of this character, the antenna can reduce the effect caused by absorption of electromagnetic waves into a dielectric body during emission of the electromagnetic waves, even when worn on a dielectric body such as a living body 11. The wireless communication device 90 is thus worn on a living body 11 and can be used in a wide variety of applications described later.

(Antenna)

An antenna according to embodiments of the present disclosure will be described below. A resonant structure may include a resonator. The resonant structure includes a resonator and other members and may be implemented in a complex form. A resonator 10 illustrated in FIG. 1 to FIG. 62 includes a base 20, pair conductors 30, a third conductor 40, and a fourth conductor 50. The base 20 is in contact with the pair conductors 30, the third conductor 40, and the fourth conductor 50. In the resonator 10, the pair conductors 30, the third conductor 40, and the fourth conductor 50 function as resonators. The resonator 10 may resonate at a plurality of resonance frequencies. Of the resonance frequencies of the resonator 10, one resonance frequency is referred to as a first frequency $f_1$. The first frequency $f_1$ has a wavelength of $\lambda_1$. The resonator 10 may have at least one of at least one resonance frequency as an operating frequency. The resonator 10 has the first frequency $f_1$ as an operating frequency.

The base 20 may include any one of a ceramic material and a resin material as its composition. Examples of the ceramic material include sintered aluminum oxide, sintered aluminum nitride, sintered mullite, sintered glass ceramics, crystallized glass including a crystalline component deposited in a glass base material, and sintered fine crystals such as mica or aluminum titanate. Examples of the resin material include those obtained by curing uncured products such as epoxy resins, polyester resins, polyimide resins, polyamide-imide resins, polyetherimide resins, and liquid crystal polymers.

The pair conductors 30, the third conductor 40, and the fourth conductor 50 may include any of a metal material, an alloy of a metal material, a hardened product of metal paste, and a conductive polymer as their compositions. All of the pair conductors 30, the third conductor 40, and the fourth conductor 50 may be of the same material. All of the pair conductors 30, the third conductor 40, and the fourth conductor 50 may be of different materials. The combination of any of the pair conductors 30, the third conductor 40, and the fourth conductor 50 may be of the same material. Examples of the metal material include copper, silver, palladium, gold, platinum, aluminum, chromium, nickel, cadmium lead, selenium, manganese, tin, vanadium, lithium, cobalt, and titanium. The alloy includes a plurality of metal materials. Examples of the metal paste agent include those obtained by mixing powder of a metal material with an organic solvent and a binder. Examples of the binder include epoxy resins, polyester resins, polyimide resins, polyamide-imide resins, and polyetherimide resins. Examples of the conductive polymer include polythiophene-based polymers, polyacethylene-based polymers, polyaniline-based polymers, and polypyrrole-based polymers.

The resonator 10 has two pair conductors 30. The pair conductors 30 include a plurality of conductive bodies. The pair conductors 30 include a first conductor 31 and a second conductor 32. The pair conductors 30 may include three or more conductive bodies. Each conductor of the pair conductors 30 is spaced apart from another conductor in a first axis. In the conductors of the pair conductors 30, one conductor may be paired with another conductor. Each conductor of the pair conductors 30 can be viewed as an electric conductor from the resonator between the paired conductors. The first conductor 31 is positioned away from the second conductor 32 in the first axis. The conductors 31 and 32 extend along a second plane intersecting the first axis.

In the present disclosure, the first axis (first axis) is denoted as x direction. In the present disclosure, a third axis (third axis) is denoted as y direction. In the present disclosure, a second axis (second axis) is denoted as z direction. In the present disclosure, a first plane (first plane) is denoted as xy plane. In the present disclosure, a second plane (second plane) is denoted as yz plane. In the present disclosure, a third plane (third plane) is denoted as zx plane. These planes are planes (plane) in a coordinate space (coordinate space) and are not intended to indicate a particular plate (plate) or a particular surface (surface). In the present disclosure, the surface integral (surface integral) in the xy plane may be denoted as first surface integral. In the present disclosure, the surface integral in the yz plane may be denoted as second surface integral. In the present disclosure, the surface integral in the zx plane may be denoted as third surface integral. The surface integral (surface integral) is represented by a unit such as square meter (square meter). In the present disclosure, the length in the x direction may be simply referred to as "length". In the present disclosure, the length in the y direction may be simply referred to as "width". In the present disclosure, the length in the z direction may be simply referred to as "height".

In an example, the conductors 31 and 32 are positioned at end portions of the base 20 in the x direction. A part of each of the conductor 31, 32 may partially face the outside of the base 20. A part of each of the conductor 31, 32 may be positioned inside the base 20 and another part thereof may be positioned outside the base 20. Each of the conductor 31, 32 may be positioned in the base 20.

The third conductor 40 functions as a resonator. The third conductor 40 may include at least one type of line-type, patch-type, and slot-type resonators. In an example, the third conductor 40 is positioned on the base 20. In an example, the third conductor 40 is positioned at an end of the base 20 in the z direction. In an example, the third conductor 40 may be positioned in the base 20. A part of the third conductor 40 may be positioned inside the base 20 and another part may be positioned outside the base 20. The surface of a part of the third conductor 40 may face the outside of the base 20.

The third conductor 40 includes at least one conductive body. The third conductor 40 may include a plurality of conductive bodies. When the third conductor 40 includes a plurality of conductive bodies, the third conductor 40 may be called a third conductor group. The third conductor 40 includes at least one conductive layer. The third conductor 40 includes at least one conductive body in one conductive layer. The third conductor 40 may include a plurality of conductive layers. For example, the third conductor 40 may include three or more conductive layers. The third conductor 40 includes at least one conductive body in each of a plurality of conductive layers. The third conductor 40 extends in the xy plane. The xy plane includes the x direction. Each conductive layer of the third conductor 40 extends along the xy plane.

In an example of a plurality of embodiments, the third conductor 40 includes a first conductive layer 41 and a second conductive layer 42. The first conductive layer 41 extends along the xy plane. The first conductive layer 41 may be positioned on the base 20. The second conductive layer 42 extends along the xy plane. The second conductive layer 42 may be capacitively coupled to the first conductive layer 41. The second conductive layer 42 may be electrically connected to the first conductive layer 41. Two conductive layers capacitively coupled may be opposed to each other in the y direction. Two conductive layers capacitively coupled may be opposed to each other in the x direction. Two conductive layers capacitively coupled may be opposed to each other in the first plane. Two conductive layers opposed to each other in the first plane may be paraphrased as "two conductive bodies are present in one conductive layer". At least a part of the second conductive layer 42 may overlap the first conductive layer 41 as viewed in the z direction. The second conductive layer 42 may be positioned in the base 20.

The fourth conductor 50 is positioned away from the third conductor 40. The fourth conductor 50 is electrically connected to each conductor 31, 32 of the pair conductors 30. The fourth conductor 50 is electrically connected to the first conductor 31 and the second conductor 32. The fourth conductor 50 extends along the third conductor 40. The fourth conductor 50 extends along the first plane. The fourth conductor 50 extends from the first conductor 31 to the second conductor 32. The fourth conductor 50 is positioned on the base 20. The fourth conductor 50 may be positioned in the base 20. A part of the fourth conductor 50 may be positioned inside the base 20 and another part may be positioned outside the base 20. The surface of a part of the fourth conductor 50 may face the outside of the base 20.

In an example of a plurality of embodiments, the fourth conductor 50 may function as a ground conductor in the resonator 10. The fourth conductor 50 may serve as a potential reference of the resonator 10. The fourth conductor 50 may be connected to the ground of a device having the resonator 10.

In an example of a plurality of embodiments, the resonator 10 may include the fourth conductor 50 and a reference potential layer 51. The reference potential layer 51 is positioned away from the fourth conductor 50 in the z direction. The reference potential layer 51 is electrically insulated from the fourth conductor 50. The reference potential layer 51 may serve as a potential reference of the resonator 10. The reference potential layer 51 may be electrically connected to the ground of a device having the resonator 10. The fourth conductor 50 may be electrically isolated from the ground of a device having the resonator 10. The reference potential layer 51 is opposed to the third conductor 40 or the fourth conductor 50 in the z direction.

In an example of a plurality of embodiments, the reference potential layer 51 is opposed to the third conductor 40 with the fourth conductor 50 interposed therebetween. The fourth conductor 50 is positioned between the third conductor 40 and the reference potential layer 51. The spacing between the reference potential layer 51 and the fourth conductor 50 is narrower than the spacing between the third conductor 40 and the fourth conductor 50.

In the resonator 10 including the reference potential layer 51, the fourth conductor 50 may include one or more conductive bodies. In the resonator 10 including the reference potential layer 51, the fourth conductor 50 may include one or more conductive bodies, and the third conductor 40 may be one conductive body connected to the pair conductors 30. In the resonator 10 including the reference potential layer 51, each of the third conductor 40 and the fourth conductor 50 may include at least one resonator.

In the resonator 10 including the reference potential layer 51, the fourth conductor 50 may include a plurality of conductive layers. For example, the fourth conductor 50 may include a third conductive layer 52 and a fourth conductive layer 53. The third conductive layer 52 may be capacitively coupled to the fourth conductive layer 53. The third conductive layer 52 may be electrically connected to the first conductive layer 41. Two conductive layers capacitively coupled may be opposed to each other in the y direction. Two conductive layers capacitively coupled may be opposed to each other in the x direction. Two conductive layers capacitively coupled may be opposed to each other in the xy plane.

The distance between two conductive layers opposed to each other in the z direction and capacitively coupled is shorter than the distance between the conductor group and the reference potential layer 51. For example, the distance between the first conductive layer 41 and the second conductive layer 42 is shorter than the distance between the third conductor 40 and the reference potential layer 51. For example, the distance between the third conductive layer 52 and the fourth conductive layer 53 is shorter than the distance between the fourth conductor 50 and the reference potential layer 51.

Each of the first conductor 31 and the second conductor 32 may include one or more conductive bodies. Each of the first conductor 31 and the second conductor 32 may be one conductive body. Each of the first conductor 31 and the second conductor 32 may include a plurality of conductive bodies. Each of the first conductor 31 and the second conductor 32 may include at least one fifth conductive layer 301 and a plurality of fifth conductors 302. The pair conductors 30 include at least one fifth conductive layer 301 and a plurality of fifth conductors 302.

The fifth conductive layer 301 extends in the y direction. The fifth conductive layer 301 extends along the xy plane. The fifth conductive layer 301 is a conductive body in the form of a layer. The fifth conductive layer 301 may be positioned on the base 20. The fifth conductive layer 301 may be positioned in the base 20. A plurality of fifth conductive layers 301 are spaced apart from each other in the z direction. A plurality of fifth conductive layers 301 are arranged in the z direction. A plurality of fifth conductive layers 301 partially overlap as viewed in the z direction. The fifth conductive layer 301 electrically connects a plurality of fifth conductors 302. The fifth conductive layer 301 is a connecting conductor that connects a plurality of fifth conductors 302. The fifth conductive layer 301 may be electrically connected to any conductive layer of the third conductor 40. In an embodiment, the fifth conductive layer 301 is electrically connected to the second conductive layer 42. The fifth conductive layer 301 may be integrated with the second conductive layer 42. In an embodiment, the fifth conductive layer 301 may be electrically connected to the fourth conductor 50. The fifth conductive layer 301 may be integrated with the fourth conductor 50.

Each fifth conductor 302 extends in the z direction. A plurality of fifth conductors 302 are spaced apart from each other in the y direction. The distance between the fifth conductors 302 is equal to or less than ½ wavelength of $\lambda_1$. When the distance between the fifth conductors 302 electrically connected is equal to or shorter than $\lambda_1/2$, each of the first conductor 31 and the second conductor 32 can reduce leakage of electromagnetic waves in the resonance frequency band from between the fifth conductors 302. The pair conductors 30 can be viewed as electric conductors from a unit structure since leakage of electromagnetic waves in the resonance frequency band is small. At least a part of a plurality of fifth conductors 302 is electrically connected to the fourth conductor 50. In an embodiment, a part of a plurality of fifth conductors 302 may electrically connect the fourth conductor 50 to the fifth conductive layer 301. In an embodiment, a plurality of fifth conductors 302 may be electrically connected to the fourth conductor 50 through the fifth conductive layer 301. One or some of a plurality of fifth conductors 302 may electrically connect one fifth conductive layer 301 to another fifth conductive layer 301. A via conductor and a through hole conductor may be employed as the fifth conductor 302.

The resonator 10 includes the third conductor 40 functioning as a resonator. The third conductor 40 may function as an artificial magnetic conductor (AMC; Artificial Magnetic Conductor). The artificial magnetic conductor may be referred to as a reactive impedance surface (RIS; Reactive Impedance Surface).

The resonator 10 includes the third conductor 40 functioning as a resonator between two pair conductors 30 opposed to each other in the x direction. Two pair conductors 30 can be viewed as electric conductors (Electric Conductor) extending from the third conductor 40 in the yz plane. The resonator 10 is electrically open at an end thereof in the y direction. The resonator 10 has a high impedance in the zx planes at both ends thereof in the y direction. The zx planes at both ends in the y direction of the resonator 10 are viewed as magnetic conductors (Magnetic Conductor) from the third conductor 40. Since the resonator 10 is surrounded by two electric conductors and two high-impedance planes (Magnetic Conductor), the resonator of the third conductor 40 has an artificial magnetic conductor character (Artificial Magnetic Conductor character) in the z direction. Surrounded by two electric conductors and two high-impedance planes, the resonator of the third conductor 40 has an artificial magnetic conductor character in a finite number.

In the "artificial magnetic conductor character", the phase difference between an incident wave and a reflected wave at an operating frequency is 0 degrees. In the resonator 10, the phase difference between an incident wave and a reflected wave at a first frequency $f_1$ is 0 degrees. In the "artificial magnetic conductor character", the phase difference between an incident wave and a reflected wave in an operating frequency band is −90 degrees to +90 degrees. The operating frequency band is a frequency band between a second frequency $f_2$ and a third frequency $f_3$. The second frequency $f_2$ is a frequency at which the phase difference between an incident wave and a reflected wave is +90 degrees. The third frequency $f_3$ is a frequency at which the phase difference between an incident wave and a reflected wave is −90 degrees. The width of the operating frequency band determined based on the second and the third frequencies may be equal to or greater than 100 MHz, for example, when the operating frequency is about 2.5 GHz. The width of the operating frequency band may be equal to or greater than 5 MHz, for example, when the operating frequency is about 400 MHz.

The operating frequency of the resonator 10 may be different from the resonance frequency of each resonator of the third conductor 40. The operating frequency of the resonator 10 may vary depending on the length, size, shape, material, etc. of the base 20, the pair conductors 30, the third conductor 40, and the fourth conductor 50.

<<Embodiments of Arrangement of Independent Resonators. In Terms of Making Finite>>

In an example of a plurality of embodiments, the third conductor 40 may include at least one unit resonator 40X. The third conductor 40 may include one unit resonator 40X. The third conductor 40 may include a plurality of unit resonators 40X. The unit resonator 40X is positioned overlapping with the fourth conductor 50 as viewed in the z direction. The unit resonator 40X is opposed to the fourth conductor 50. The unit resonator 40X may function as a frequency selective surface (FSS; Frequency Selective Surface). A plurality of unit resonators 40X are arranged along the xy plane. A plurality of unit resonators 40X may be arranged regularly in the xy plane. The unit resonators 40X may be arranged in the form of a square grid (square grid), an oblique grid (oblique grid), a rectangular grid (rectangular grid), and a hexagonal grid (hexagonal grid).

The third conductor 40 may include a plurality of conductive layers arranged in the z direction. Each of the plurality of conductive layers of the third conductor 40 includes an equivalent of at least one unit resonator. For example, the third conductor 40 includes a first conductive layer 41 and a second conductive layer 42.

The first conductive layer 41 includes an equivalent of at least one first unit resonator 41X. The first conductive layer 41 may include one first unit resonator 41X. The first conductive layer 41 may include a plurality of first divisional resonators 41Y obtained by dividing one first unit resonator 41X into a plurality of pieces. The plurality of first divisional resonators 41Y may be an equivalent of at least one first unit resonator 41X with an adjacent unit structure 10X. A plurality of first divisional resonators 41Y are positioned at an end portion of the first conductive layer 41. The first unit resonator 41X and the first divisional resonator 41Y may be called a third conductor.

The second conductive layer 42 includes an equivalent of at least one second unit resonator 42X. The second conductive layer 42 may include one second unit resonator 42X. The second conductive layer 42 may include a plurality of second divisional resonators 42Y obtained by dividing one second unit resonator 42X into a plurality of pieces. The plurality of second divisional resonators 42Y may be an equivalent of at least one second unit resonator 42X with an adjacent unit structure 10X. The plurality of second divisional resonators 42Y are positioned at an end portion of the second conductive layer 42. The second unit resonator 42X and the second divisional resonator 42Y may be called a third conductor.

At least a part of the second unit resonator 42X and the second divisional resonator 42Y is positioned overlapping with the first unit resonator 41X and the first divisional resonator 41Y as viewed in the Z direction. In the third conductor 40, at least a part of the unit resonator and the divisional resonator in each layer is stacked in the Z direction to form one unit resonator 40X. The unit resonator 40X includes an equivalent of at least one unit resonator in each layer.

When the first unit resonator 41X includes a line-type or patch-type resonator, the first conductive layer 41 has at least one first unit conductor 411. The first unit conductor 411 may function as a first unit resonator 41X or a first divisional resonator 41Y. The first conductive layer 41 has a plurality of first unit conductors 411 arranged in n rows and m columns in the xy directions, where n and m are natural numbers of 1 or greater independent of each other. In an example illustrated in FIGS. 1 to 9, etc., the first conductive layer 41 has six first unit conductors 411 arranged in a grid of two rows and three columns. The first unit conductors 411 may be arranged in the form of a square grid, an oblique grid, a rectangular grid, and a hexagonal grid. The first unit conductor 411 corresponding to the first divisional resonator 41Y is positioned at an end portion in the xy plane of the first conductive layer 41.

When the first unit resonator 41X is a slot-type resonator, at least one conductive layer of the first conductive layer 41 extends in the xy directions. The first conductive layer 41 has at least one first unit slot 412. The first unit slot 412 may function as a first unit resonator 41X or a first divisional resonator 41Y. The first conductive layer 41 may include a plurality of first unit slots 412 arranged in n rows and m columns in the xy directions, where n and m are natural numbers of 1 or greater independent of each other. In an example illustrated in FIGS. 6 to 9, etc., the first conductive layer 41 has six first unit slots 412 arranged in a grid of two rows and three columns. The first unit slots 412 may be arranged in the form of a square grid, an oblique grid, a rectangular grid, and a hexagonal grid. The first unit slot 412 corresponding to the first divisional resonator 41Y is positioned at an end portion in the xy plane of the first conductive layer 41.

When the second unit resonator 42X is a line-type or patch-type resonator, the second conductive layer 42 includes at least one second unit conductor 421. The second conductive layer 42 may include a plurality of second unit conductors 421 arranged in the xy directions. The second unit conductors 421 may be arranged in the form of a square grid, an oblique grid, a rectangular grid, and a hexagonal grid. The second unit conductor 421 may function as a second unit resonator 42X or a second divisional resonator 42Y. The second unit conductor 421 corresponding to the second divisional resonator 42Y is positioned at an end portion in the xy plane of the second conductive layer 42.

At least a part of the second unit conductor 421 overlaps with at least one of the first unit resonator 41X and the first divisional resonator 41Y as viewed in the z direction. The second unit conductor 421 may overlap with a plurality of first unit resonators 41X. The second unit conductor 421 may overlap with a plurality of first divisional resonators 41Y. The second unit conductor 421 may overlap with one first unit resonator 41X and four first divisional resonators 41Y. The second unit conductor 421 may overlap only with one first unit resonator 41X. The centroid of the second unit conductor 421 may overlap with one first unit conductor 41X. The centroid of the second unit conductor 421 may be positioned between a plurality of first unit conductors 41X and the first divisional resonator 41Y. The centroid of the second unit conductor 421 may be positioned between two first unit resonators 41X arranged in the x direction or the y direction.

At least a part of the second unit conductor 421 may overlap with two first unit conductors 411. The second unit conductor 421 may overlap only with one first unit conductor 411. The centroid of the second unit conductor 421 may be positioned between two first unit conductors 411. The centroid of the second unit conductor 421 may overlap with one first unit conductor 411. At least a part of the second unit conductor 421 may overlap with the first unit slot 412. The second unit conductor 421 may overlap only with one first unit slot 412. The centroid of the second unit conductor 421 may be positioned between two first unit slots 412 arranged in the x direction or the y direction. The centroid of the second unit conductor 421 may overlap with one first unit slot 412.

When the second unit resonator 42X is a slot-type resonator, at least one conductive layer of the second conductive layer 42 extends along the xy plane. The second conductive layer 42 has at least one second unit slot 422. The second unit slot 422 may function as a second unit resonator 42X or a second divisional resonator 42Y. The second conductive layer 42 may include a plurality of second unit slots 422 arranged in the xy plane. The second unit slots 422 may be arranged in the form of a square grid, an oblique grid, a rectangular grid, and a hexagonal grid. The second unit slot 422 corresponding to the second divisional resonator 42Y is positioned at an end portion in the xy plane of the second conductive layer 42.

At least a part of the second unit slot 422 overlaps with at least one of the first unit resonator 41X and the first divisional resonator 41Y in the y direction. The second unit slot 422 may overlap with a plurality of first unit resonators 41X. The second unit slot 422 may overlap with a plurality of first divisional resonators 41Y. The second unit slot 422 may overlap with one first unit resonator 41X and four first divisional resonators 41Y. The second unit slot 422 may overlap only with one first unit resonator 41X. The centroid of the second unit slot 422 may overlap with one first unit conductor 41X. The centroid of the second unit slot 422 may be positioned between a plurality of first unit conductors 41X. The centroid of the second unit slot 422 may be positioned between two first unit resonators 41X and the first divisional resonator 41Y arranged in the x direction or the y direction.

At least a part of the second unit slot 422 may overlap with two first unit conductors 411. The second unit slot 422 may overlap only with one first unit conductor 411. The centroid of the second unit slot 422 may be positioned between two first unit conductors 411. The centroid of the second unit slot 422 may overlap with one first unit conductor 411. At least a part of the second unit slot 422 may overlap with the first unit slot 412. The second unit slot 422 may overlap only with one first unit slot 412. The centroid of the second unit slot 422 may be positioned between two first unit slots 412 arranged in the x direction or the y direction. The center of the second unit slot 422 may overlap with one first unit slot 412.

The unit resonator 40X includes an equivalent of at least one first unit resonator 41X and an equivalent of at least one second unit resonator 42X. The unit resonator 40X may include one first unit resonator 41X. The unit resonator 40X may include a plurality of first unit resonators 41X. The unit resonator 40X may include one first divisional resonator 41Y. The unit resonator 40X may include a plurality of first divisional resonators 41Y. The unit resonator 40X may include a part of the first unit resonator 41X. The unit resonator 40X may include one or more partial first unit resonators 41X. The unit resonator 40X includes a plurality of partial resonators among one or more partial first unit resonators 41X and one or more first divisional resonators 41Y. A plurality of partial resonators included in the unit resonator 40X are combined into a first unit resonator 41X equivalent to at least one. The unit resonator 40X does not necessarily include a first unit resonator 41X but may include a plurality of first divisional resonators 41Y. The unit resonator 40X may include, for example, four first divisional resonators 41Y. The unit resonator 40X may include only a plurality of partial first unit resonators 41X. The unit resonator 40X may include one or more partial first unit resonators 41X and one or more first divisional resonators 41Y. The unit resonator 40X may include, for example, two partial first unit resonators 41X and two first divisional resonators 41Y. In the unit resonator 40X, the mirror images of the included first conductive layer 41 at the ends in the x direction may be substantially identical. In the unit resonator 40X, the included first conductive layer 41 may be substantially symmetric with respect to the center line extending in the z direction.

The unit resonator 40X may include one second unit resonator 42X. The unit resonator 40X may include a plurality of second unit resonators 42X. The unit resonator 40X may include one second divisional resonator 42Y. The unit resonator 40X may include a plurality of second divisional resonators 42Y. The unit resonator 40X may include a part of the second unit resonator 42X. The unit resonator 40X may include one or more partial second unit resonators 42X. The unit resonator 40X includes a plurality of partial resonators among one or more partial second unit resonators 42X and one or more second divisional resonators 42Y. A plurality of partial resonators included in the unit resonator 40X are combined into a second unit resonator 42X equivalent to one. The unit resonator 40X does not necessarily include a second unit resonator 42X but may include a plurality of second divisional resonators 42Y. The unit resonator 40X may include, for example, four second divisional resonators 42Y. The unit resonator 40X may include only a plurality of partial second unit resonators 42X. The unit resonator 40X may include one or more partial second unit resonators 42X and one or more second divisional resonators 42Y. The unit resonator 40X may include, for example, two partial second unit resonators 42X and two second divisional resonators 42Y. In the unit resonator 40X, the mirror images of the included second conductive layer 42 at the ends in the x direction may be substantially identical. In the unit resonator 40X, the included second conductive layer 42 may be substantially symmetric with respect to the centerline extending in the y direction.

In an example of a plurality of embodiments, the unit resonator 40X includes one first unit resonator 41X and a plurality of partial second unit resonators 42X. For example, the unit resonator 40X includes one first unit resonator 41X and half of four second unit resonators 42X. This unit resonator 40X includes an equivalent of one first unit resonator 41X and an equivalent of two second unit resonators 42X. The configuration of the unit resonator 40X is not limited to this example.

The resonator 10 may include at least one unit structure 10X. The resonator 10 may include a plurality of unit structures 10X. The plurality of unit structures 10X may be arranged in the xy plane. The plurality of unit structures 10X may be arranged in the form of a square grid, an oblique grid, a rectangular grid, and a hexagonal grid. The unit structure 10X includes a repetition unit of any one of a square grid (square grid), an oblique grid (oblique grid), a rectangular grid (rectangular grid), and a hexagonal grid (hexagonal grid). The unit structures 10X may be arranged infinitely along the xy plane to function as an artificial magnetic conductor (AMC).

The unit structure 10X may include at least a part of the base 20, at least a part of the third conductor 40, and at least a part of the fourth conductor 50. The sections of the base 20, the third conductor 40, and the fourth conductor 50 included in the unit structure 10X overlap as viewed in the z direction. The unit structure 10X includes a unit resonator 40X, a part of the base 20 overlapping with the unit resonator 40X as viewed in the z direction, and the fourth conductor 50 overlapping with the unit resonator 40X as viewed in the z direction. The resonator 10 may include, for example, six unit structures 10X arranged in two rows and three columns.

The resonator 10 may have at least one unit structure 10X between two pair conductors 30 opposed to each other in the x direction. Two pair conductors 30 can be viewed as electric conductors extending from the unit structure 10X in the yz plane. The unit structure 10X is open at an end in the y direction. The unit structure 10X has a high impedance in the zx planes at both ends in the y direction. The unit structure 10X can be viewed as magnetic conductors in the zx planes at both ends in the y direction. The unit structures 10X may be in line symmetry with respect to the z direction when repeatedly arranged. Surrounded by two electric conductors and two high-impedance planes (magnetic conductors), the unit structure 10X has an artificial magnetic conductor character in the z direction. Surrounded by two electric conductors and two high-impedance planes (magnetic conductors), the unit structure 10X has an artificial magnetic conductor character in a finite number.

The operating frequency of the resonator 10 may be different from the operating frequency of the first unit resonator 41X. The operating frequency of the resonator 10 may be different from the operating frequency of the second unit resonator 42X. The operating frequency of the resonator 10 may vary depending on, for example, coupling of the first unit resonator 41X and the second unit resonator 42X that constitute the unit resonator 40X.

Additional Embodiments; Zeroth Order Resonant System

The third conductor 40 may include a first conductive layer 41 and a second conductive layer 42. The first conductive layer 41 includes at least one first unit conductor 411. The first unit conductor 411 includes a first connecting conductor 413 and a first floating conductor 414. The first connecting conductor 413 is connected to one of the pair conductors 30. The first floating conductor 414 is not connected to the pair conductors 30. The second conductive layer 42 includes at least one second unit conductor 421. The second unit conductor 421 includes a second connecting conductor 423 and a second floating conductor 424. The second connecting conductor 423 is connected to one of the pair conductors 30. The second floating conductor 424 is not connected to the pair conductors 30. The third conductor 40 may include a first unit conductor 411 and a second unit conductor 421.

The first connecting conductor 413 may have a length along the x direction longer than the first floating conductor 414. The first connecting conductor 413 may have a length along the x direction shorter than the first floating conductor 414. The first connecting conductor 413 may have half of the length along the x direction, compared with the first floating conductor 414. The second connecting conductor 423 may have a length along the x direction longer than the second floating conductor 424. The second connecting conductor 423 may have a length along the x direction shorter than the second floating conductor 424. The second connecting conductor 423 may have half of the length along the x direction, compared with the second floating conductor 424.

The third conductor 40 may include a current path 40I serving as a current path between the first conductor 31 and the second conductor 32 when the resonator 10 resonates. The current path 40I may be connected to the first conductor 31 and the second conductor 32. The current path 40I has capacitance between the first conductor 31 and the second conductor 32. The capacitance of the current path 40I is connected electrically in series between the first conductor 31 and the second conductor 32. In the current path 40I, a conductive body is isolated between the first conductor 31 and the second conductor 32. The current path 40I may include a conductive body connected to the first conductor 31 and a conductive body connected to the second conductor 32.

In a plurality of embodiments, in the current path 40I, the first unit conductor 411 and the second unit conductor 421 are partially opposed to each other in the z direction. In the current path 40I, the first unit conductor 411 and the second unit conductor 421 are capacitively coupled. The first unit conductor 411 has a capacitance component at an end portion in the x direction. The first unit conductor 411 may have a capacitance component at an end portion in the y direction opposed to the second unit conductor 421 in the z direction. The first unit conductor 411 may have a capacitance component at an end portion in the x direction opposed to the second unit conductor 421 in the z direction and at an end portion in the y direction. The second unit conductor 421 has a capacitance component at an end portion in the x direction. The second unit conductor 421 may have a capacitance component at an end portion in the y direction opposed to the first unit conductor 411 in the z direction. The second unit conductor 421 may have a capacitance component at an end portion in the x direction opposed to the first unit conductor 411 in the z direction and at an end portion in the y direction.

The resonator 10 can have a lower resonance frequency by increasing the capacitive coupling in the current path 40I. When achieving a desired operating frequency, the resonator 10 can have a shorter length along the x direction by increasing the capacitance coupling of the current path 40I. In the third conductor 40, the first unit conductor 411 and the second unit conductor 421 are opposed to each other in the stacking direction of the base 20 and capacitively coupled. The third conductor 40 can adjust the capacitance between the first unit conductor 411 and the second unit conductor 421 by the opposing surface integrals.

In a plurality of embodiments, the length along the y direction of the first unit conductor 411 differs from the length along the y direction of the second unit conductor 421. When the relative position between the first unit conductor 411 and the second unit conductor 421 is shifted along the xy plane from an ideal position, the resonator 10 can reduce variation in magnitude of the capacitance since the length along the third axis differs between the first unit conductor 411 and the second unit conductor 421.

In a plurality of embodiments, the current path 40I is formed of one conductive body spatially away from the first conductor 31 and the second conductor 32 and capacitively coupled to the first conductor 31 and the second conductor 32.

In a plurality of embodiments, the current path 40I includes a first conductive layer 41 and a second conductive layer 42. This current path 40I includes at least one first unit conductor 411 and at least one second unit conductor 421. This current path 40I includes two first connecting conductors 413, two second connecting conductors 423, and one of one first connecting conductor 413 and one second connecting conductor 423. In this current path 40I, the first unit conductor 411 and the second unit conductor 421 may be alternately arranged along the first axis.

In a plurality of embodiments, the current path 40I includes a first connecting conductor 413 and a second connecting conductor 423. This current path 40I includes at least one first connecting conductor 413 and at least one second connecting conductor 423. In this current path 40I, the third conductor 40 has capacitance between the first connecting conductor 413 and the second connecting conductor 423. In an example of embodiments, the first connecting conductor 413 may be opposed to the second connecting conductor 423 and have capacitance. In an example of embodiments, the first connecting conductor 413 may be capacitively connected to the second connecting conductor 423 through another conductive body.

In a plurality of embodiments, the current path 40I includes a first connecting conductor 413 and a second floating conductor 424. This current path 40I includes two first connecting conductors 413. In this current path 40I, the third conductor 40 has capacitance between two first connecting conductors 413. In an example of embodiments, two first connecting conductors 413 may be capacitively connected to each other through at least one second floating conductor 424. In an example of embodiments, two first connecting conductors 413 may be capacitively connected to each other through at least one first floating conductor 414 and a plurality of second floating conductors 424.

In a plurality of embodiments, the current path 40I includes a first floating conductor 414 and a second connecting conductor 423. This current path 40I includes two second connecting conductors 423. In this current path 40I, the third conductor 40 has capacitance between two second connecting conductors 423. In an example of embodiments, two second connecting conductors 423 may be capacitively connected to each other through at least one first floating conductor 414. In an example of embodiments, two second connecting conductors 423 may be capacitively connected to each other through a plurality of first floating conductors 414 and at least one second floating conductor 424.

In a plurality of embodiments, each of the first connecting conductor 413 and the second connecting conductor 423 may have a length one-fourth of the wavelength λ at a resonance frequency. Each of the first connecting conductor 413 and the second connecting conductor 423 may function as a resonator with half a length of the wavelength λ. Each of the first connecting conductor 413 and the second connecting conductor 423 may oscillate in the odd mode and the even mode when the individual resonators are capacitively coupled. In the resonator 10, the resonance frequency in the even mode after capacitively coupling may be the operating frequency.

The current path 40I may be connected to the first conductor 31 at a plurality of points. The current path 40I may be connected to the second conductor 32 at a plurality of points. The current path 40I may include a plurality of electric conductive paths that conduct electricity independently, from the first conductor 31 to the second conductor 32.

In the second floating conductor 424 capacitively coupled to the first connecting conductor 413, an end of the second floating conductor 424 on the capacitively coupled side has a shorter distance to the first connecting conductor 413 than the distance to the pair conductor 30. In the first floating conductor 414 capacitively coupled to the second connecting conductor 423, an end of the first floating conductor 414 on the capacitively coupled side has a shorter distance to the second connecting conductor 423 than the distance to the pair conductor 30.

In the resonator 10 in a plurality of embodiments, the conductive layers of the third conductor 40 may have individually different lengths in the y direction. A conductive layer of the third conductor 40 is capacitively coupled to another conductive layer in the z direction. In the resonator 10, when the conductive layers differ in length in the y direction, variation in capacitance is reduced even when the conductive layers are shifted in the y direction. When the conductive layers differ in length in the y direction, the resonator 10 can expand the acceptable range of shift in the y direction of the conductive layers.

In the resonator 10 in a plurality of embodiments, the third conductor 40 has capacitance by capacitive coupling between the conductive layers. A plurality of capacitance bodies having the capacitance may be arranged in the y direction. The plurality of capacitance bodies arranged in the y direction may be electromagnetically parallel. When the resonator 10 has a plurality of capacitance bodies arranged electrically in parallel, the individual capacitance errors can complement each other.

When the resonator 10 is in a resonant state, current flowing through the pair conductors 30, the third conductor 40, and the fourth conductor 50 loops. When the resonator 10 is in a resonant state, alternating current flows through the resonator 10. In the resonator 10, current flowing through the third conductor 40 is referred to as first current, and current flowing through the fourth conductor 50 is referred to as second current. When the resonator 10 is in a resonant state, the first current flows in a direction different from the second current in the x direction. For example, when the first current flows in the +x direction, the second current flows in the −x direction. For example, when the first current flows in the −x direction, the second current flows in the +x direction. That is, when the resonator 10 is in a resonant state, loop current flows alternately in the +x direction and the −x direction. The loop current forming a magnetic field is repeatedly inverted whereby the resonator 10 emits electromagnetic waves.

In a plurality of embodiments, the third conductor 40 includes a first conductive layer 41 and a second conductive layer 42. Since the third conductor 40 has the first conductive layer 41 and the second conductive layer 42 capacitively coupled, current appears to flow in one direction globally in a resonant state. In a plurality of embodiments, current flowing through each conductor has a higher density at an end portion in the y direction.

In the resonator 10, the first current and the second current loop through the pair conductors 30. In the resonator 10, the first conductor 31, the second conductor 32, the third conductor 40, and the fourth conductor 50 form a resonant circuit. The resonance frequency of the resonator 10 is the resonance frequency of a unit resonator. When the resonator 10 includes one unit resonator or when the resonator 10 includes a part of a unit resonator, the resonance frequency of the resonator 10 varies depending on the base 20, the pair conductors 30, the third conductor 40, and the fourth conductor 50, and electromagnetic coupling of the resonator 10 with the surroundings. For example, when the periodicity of the third conductor 40 is poor, the entire resonator 10 is one unit resonator or the entire resonator 10 is a part of one unit resonator. For example, the resonance frequency of the resonator 10 varies depending on the length in the z direction of the first conductor 31 and the second conductor 32, the length in the x direction of the third conductor 40 and the fourth conductor 50, and the capacitance of the third conductor 40 and the fourth conductor 50. For example, in the resonator 10 having a large capacitance between the first unit conductor 411 and the second unit conductor 421, the resonance frequency can be lowered while the length in the z direction of the first conductor 31 and the second conductor 32 and the length in the x direction of the third conductor 40 and the fourth conductor 50 are reduced.

In a plurality of embodiments, in the resonator 10, the first conductive layer 41 is an effective radiation plane of electromagnetic waves in the z direction. In a plurality of embodiments, in the resonator 10, the first surface integral of the first conductive layer 41 is larger than the first surface integral of another conductive layer. In this resonator 10, increasing the first surface integral of the first conductive layer 41 can increase radiation of electromagnetic waves.

In a plurality of embodiments, the resonator 10 may include one or more impedance elements 45. The impedance element 45 has an impedance value between a plurality of terminals. The impedance element 45 changes the resonance frequency of the resonator 10. The impedance element 45 may include a resistor (Resistor), a capacitor (Capacitor), and an inductor (Inductor). The impedance element 45 may include a variable element that can change the impedance value. The variable element may change the impedance value by an electrical signal. The variable element may change the impedance value by a physical mechanism.

The impedance element 45 may be connected to two unit conductors arranged in the x direction of the third conductor 40. The impedance element 45 may be connected to two first unit conductors 411 arranged in the x direction. The impedance element 45 may be connected to the first connecting conductor 413 and the first floating conductor 414 arranged in the x direction. The impedance element 45 is connected to the first conductor 31 and the first floating conductor 414. The impedance element 45 may be connected to a unit conductor of the third conductor 40 at a central portion in the y direction. The impedance element 45 may be connected to a central portion in the y direction of two first unit conductors 411.

The impedance element 45 is connected electrically in series between two conductive bodies arranged in the x direction in the xy plane. The impedance element 45 may be connected electrically in series between two first unit conductors 411 arranged in the x direction. The impedance element 45 may be connected electrically in series between the first connecting conductor 413 and the first floating conductor 414 arranged in the x direction. The impedance element 45 may be connected electrically in series between the first conductor 31 and the first floating conductor 414.

The impedance element 45 may be connected electrically in parallel to two first unit conductors 411 and the second unit conductor 421 stacked in the z direction and having capacitance. The impedance element 45 may be connected electrically in parallel to the second connecting conductor 423 and the first floating conductor 414 stacked in the z direction and having capacitance.

The resonator 10 can additionally include a capacitor as the impedance element 45 to make the resonance frequency lower. The resonator 10 may additionally include an inductor as the impedance element 45 to make the resonance frequency higher. The resonator 10 may include impedance elements 45 having different impedance values. The resonator 10 may include capacitors with different electric capacitances as the impedance elements 45. The resonator 10 may include inductors with different inductances as the impedance elements 45. The resonator 10 additionally includes impedance elements 45 with different impedance values to increase the adjustment range of the resonance frequency. The resonator 10 may include both a capacitor and an inductor as impedance elements 45. The resonator 10 additionally includes both a capacitor and an inductor as impedance elements 45 to increase the adjustment range of the resonance frequency. With the provision of the impedance element 45, the entire resonator 10 may be one unit resonator or the entire resonator 10 may be a part of one unit resonator.

DESCRIPTION WITH FIGURES

Figure 1:
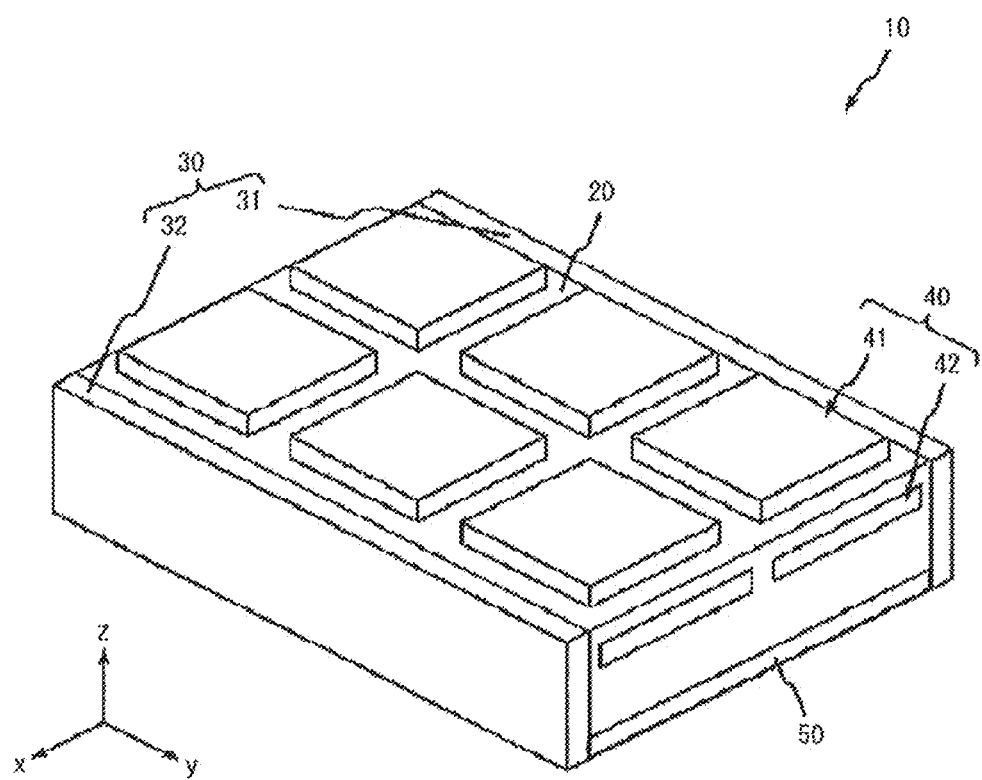
FIG. 1 is a perspective view illustrating an embodiment of a resonator.
Figure 2:
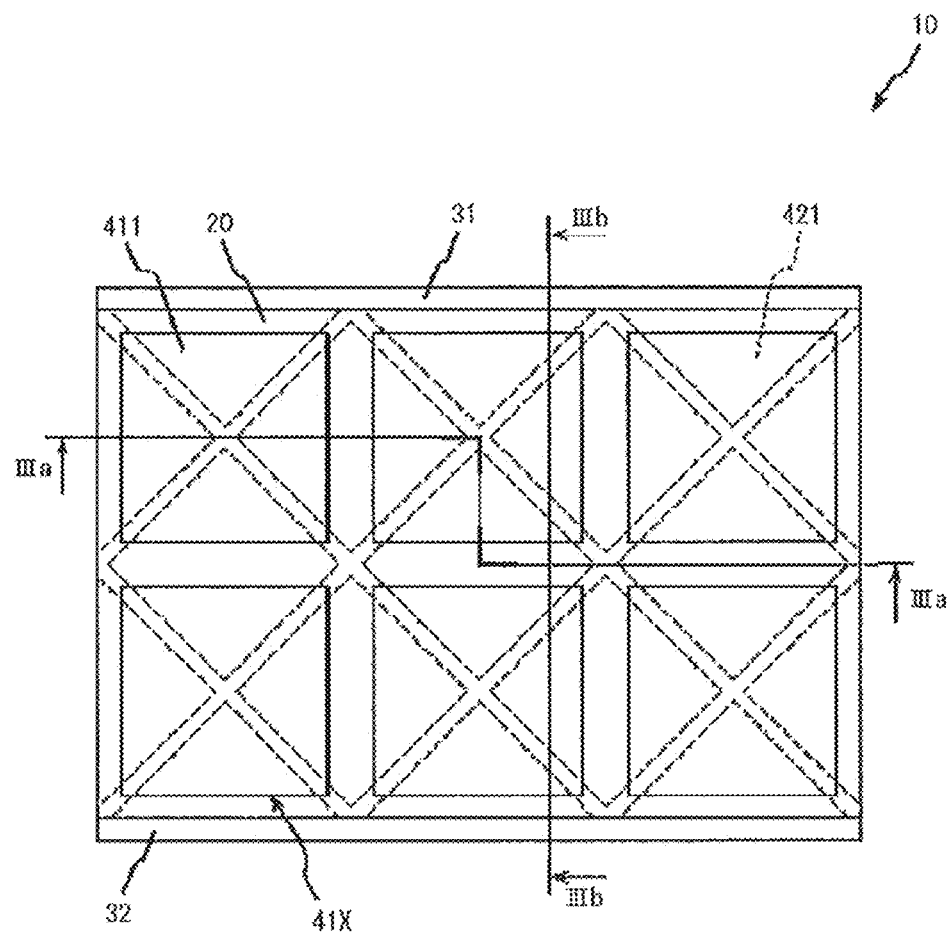
FIG. 2 is a planar view of the resonator illustrated in FIG. 1.
Figure 3A:
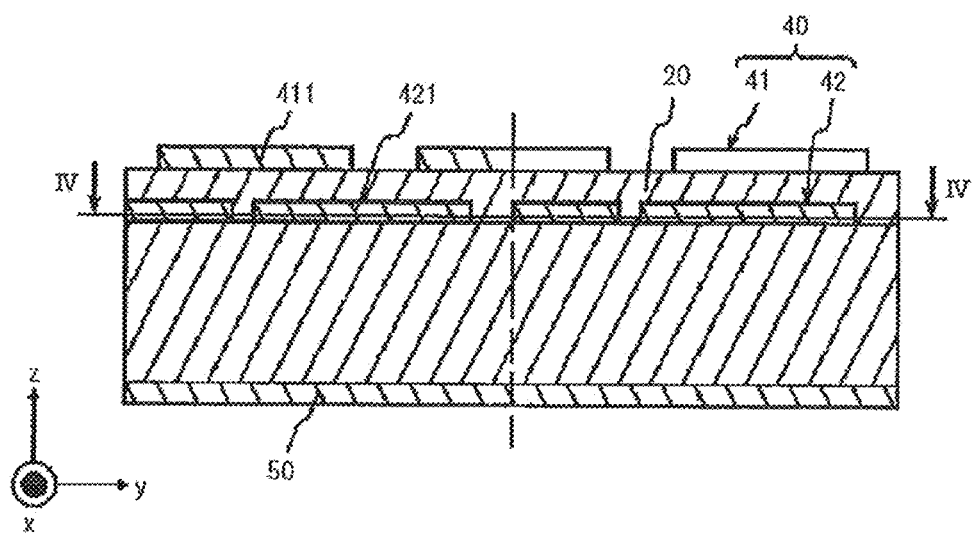
FIG. 3A is a cross-sectional view of the resonator illustrated in FIG. 1.
Figure 3B:
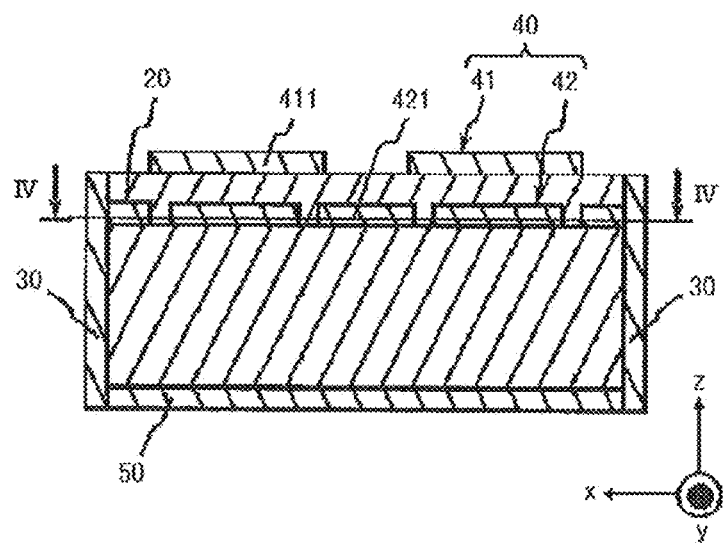
FIG. 3B is a cross-sectional view of the resonator illustrated in FIG. 1.
Figure 4:
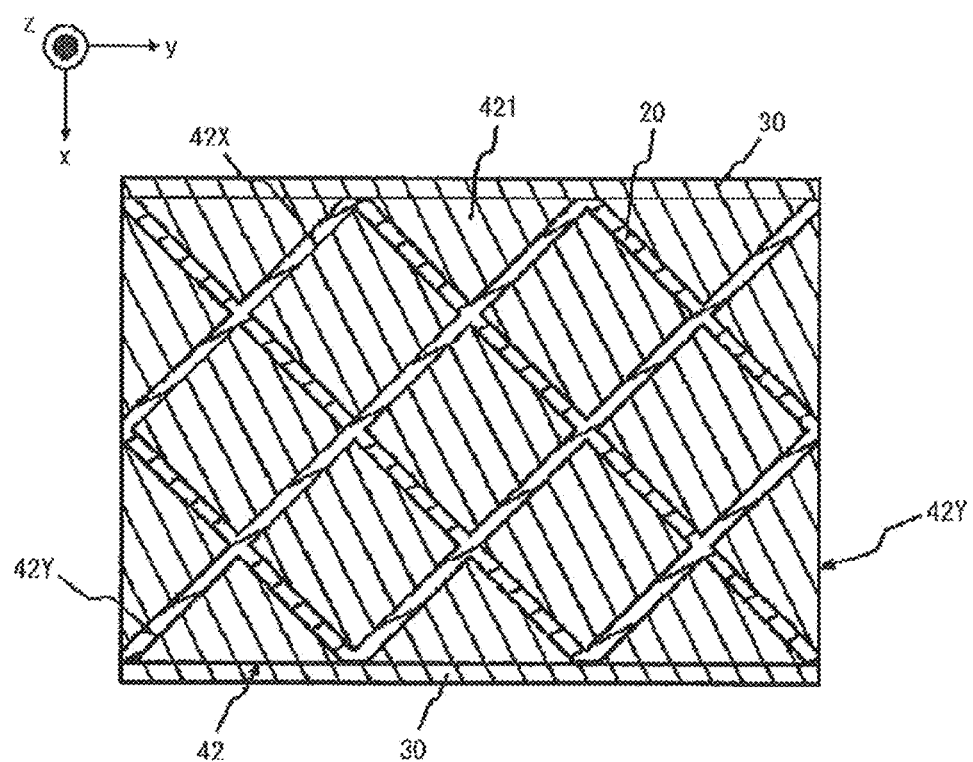
FIG. 4 is a cross-sectional view of the resonator illustrated in FIG. 1.
Figure 5:
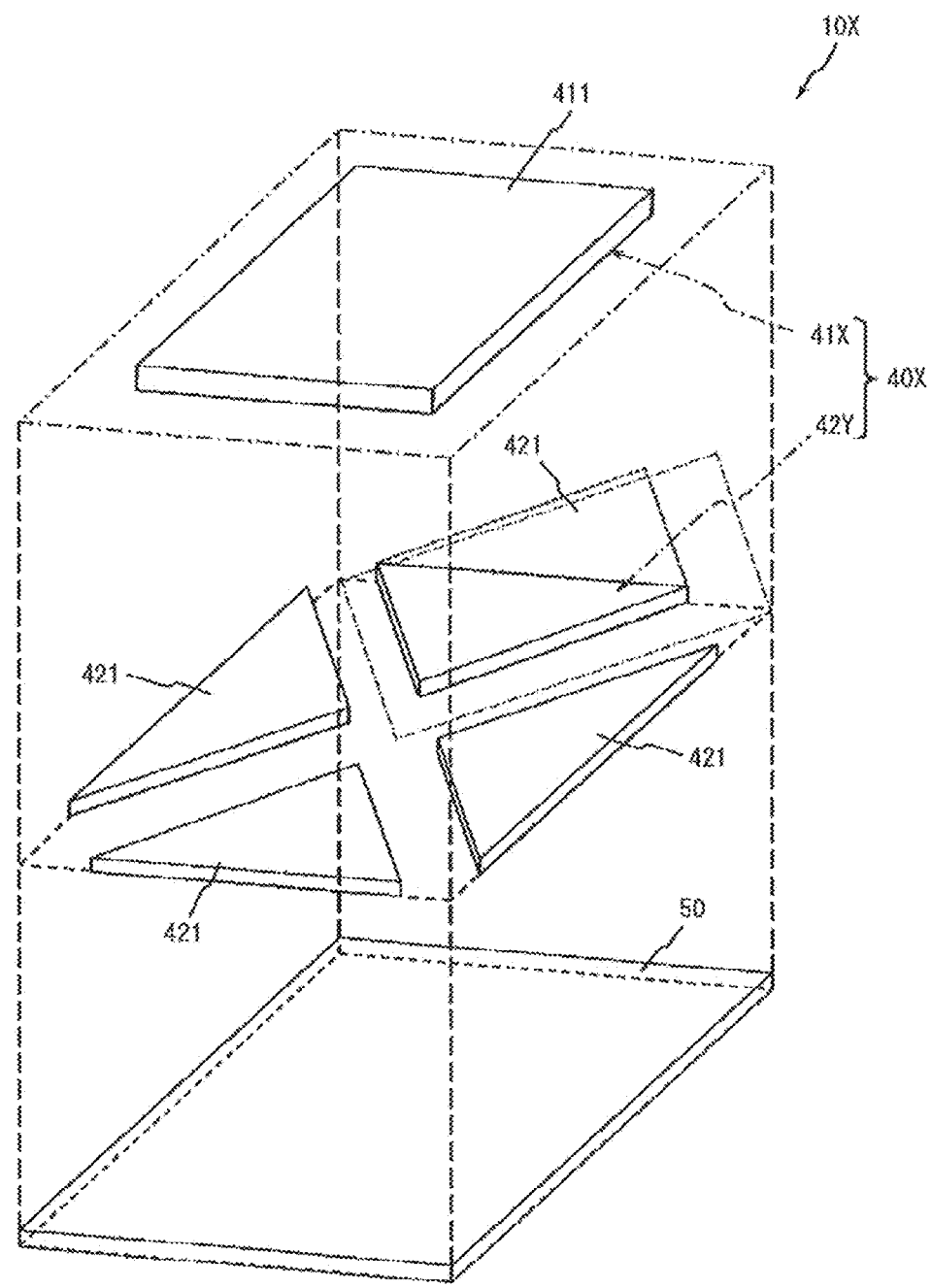
FIG. 5 is a conceptual diagram illustrating a unit structure of the resonator illustrated in FIG. 1.

FIGS. 1 to 5 are diagrams illustrating a resonator 10 that is an example of a plurality of embodiments. FIG. 1 is a schematic diagram of the resonator 10. FIG. 2 is a planar view of the xy plane from the z direction. FIG. 3A is a cross-sectional view taken along line IIIa-IIIa illustrated in FIG. 2. FIG. 3B is a cross-sectional view taken along line IIIb-IIIb illustrated in FIG. 2. FIG. 4 is a cross-sectional view taken along line IV-IV illustrated in FIGS. 3A and 3B. FIG. 5 is a conceptual diagram illustrating a unit structure 10X that is an example of a plurality of embodiments.

In the resonator 10 illustrated in FIGS. 1 to 5, a first conductive layer 41 includes a patch-type resonator as a first unit resonator 41X. A second conductive layer 42 includes a patch-type resonator as a second unit resonator 42X. The unit resonator 40X includes one first unit resonator 41X and four second divisional resonators 42Y. The unit structure 10X includes a unit resonator 40X as well as a part of the base 20 and a part of the fourth conductor 50 that overlap with the unit resonator 40X as viewed in the z direction.

Figure 6:
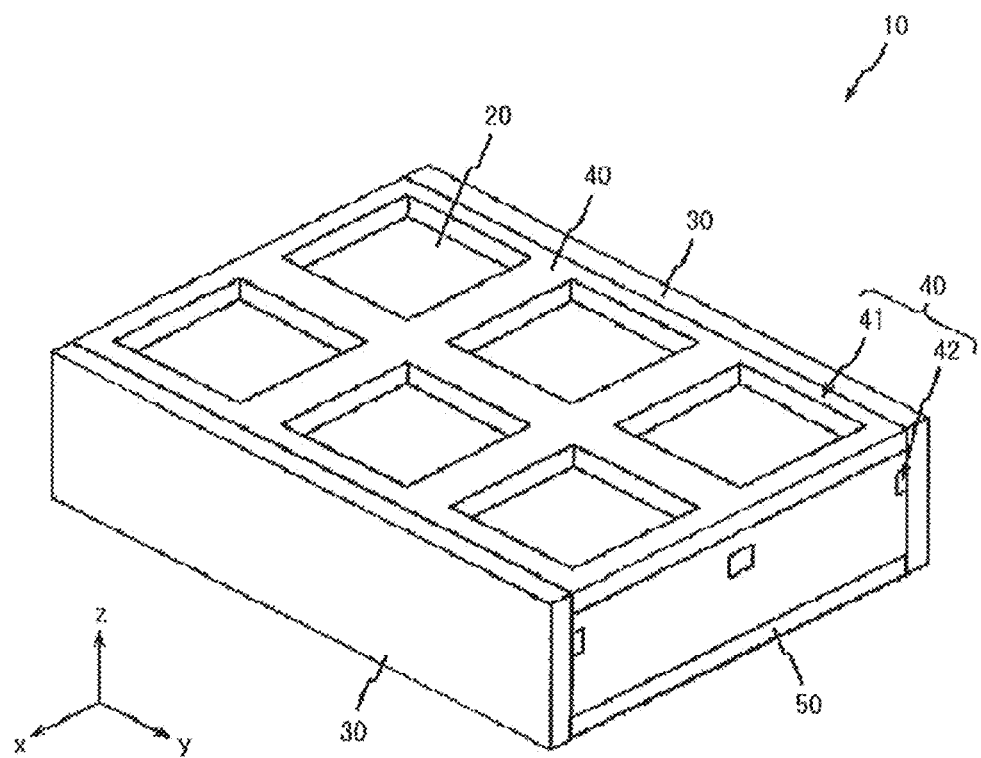
FIG. 6 is a perspective view illustrating an embodiment of a resonator.
Figure 7:
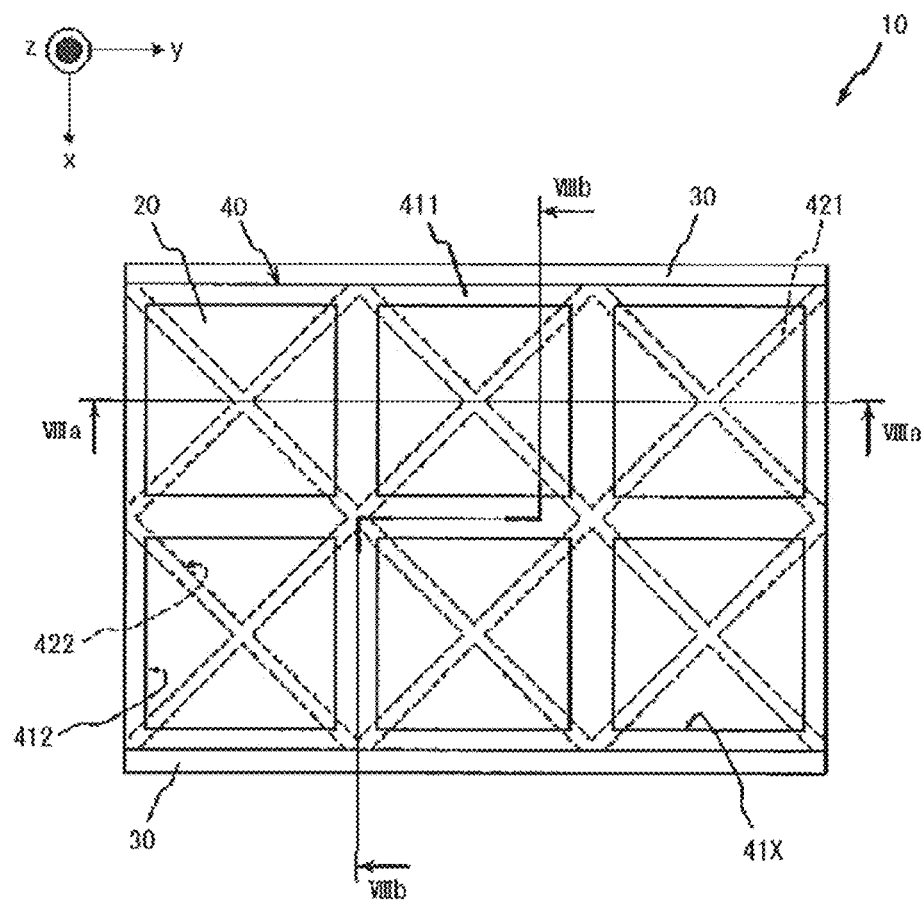
FIG. 7 is a planar view of the resonator illustrated in FIG. 6.
Figure 8A:
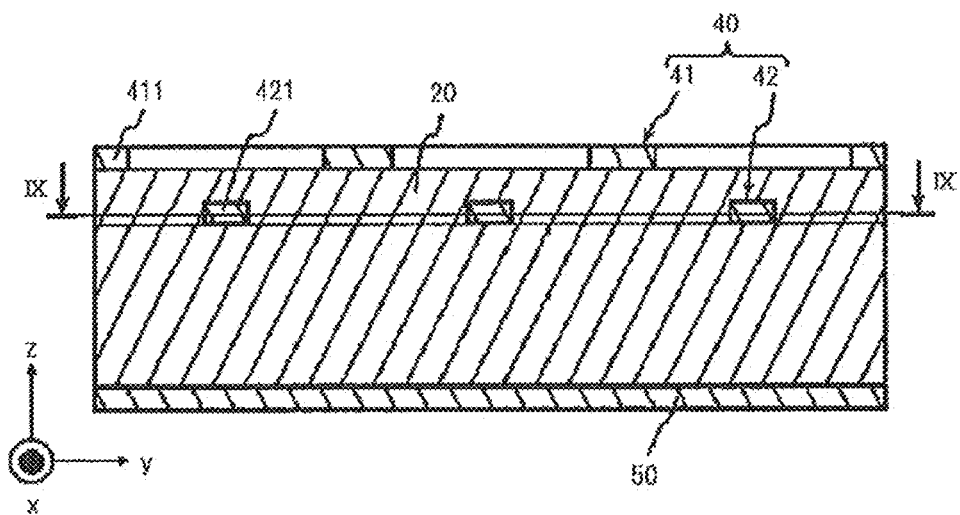
FIG. 8A is a cross-sectional view of the resonator illustrated in FIG. 6.
Figure 8B:
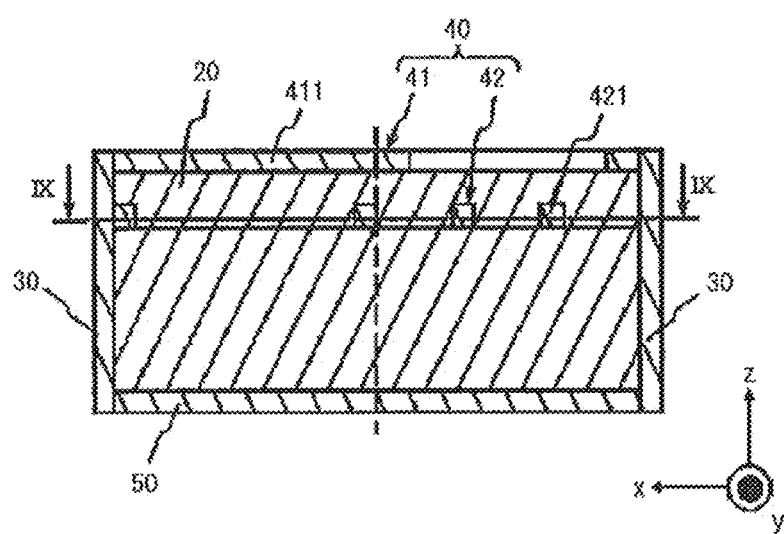
FIG. 8B is a cross-sectional view of the resonator illustrated in FIG. 6.
Figure 9:
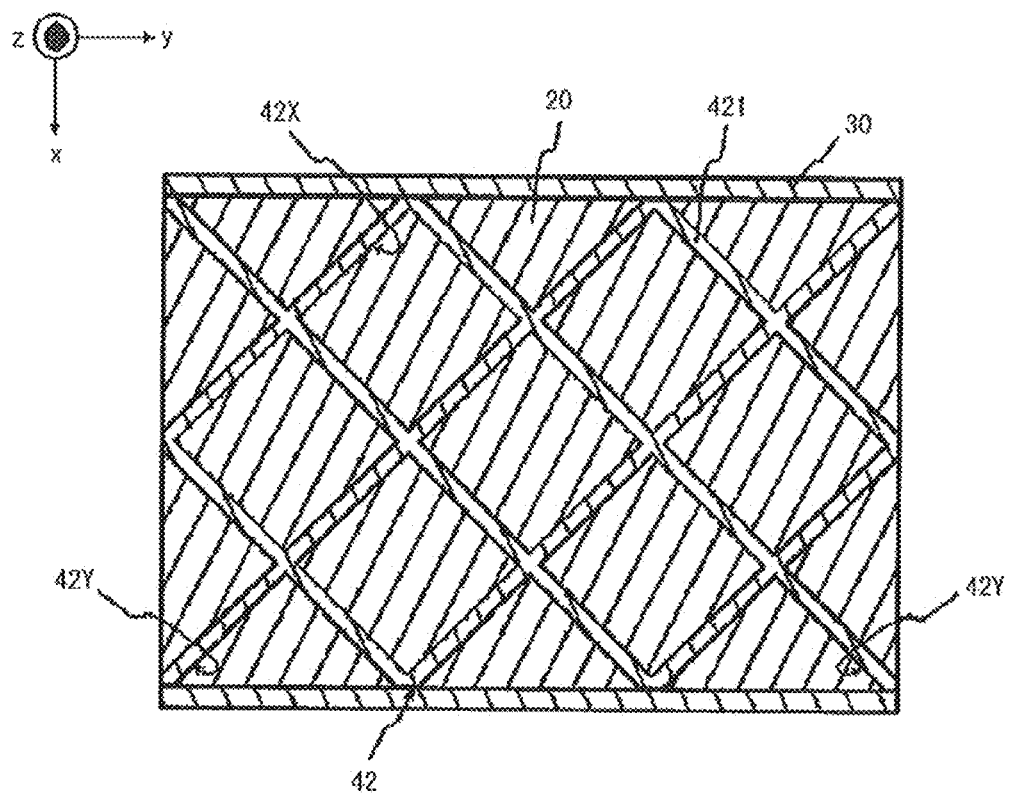
FIG. 9 is a cross-sectional view of the resonator illustrated in FIG. 6.

FIGS. 6 to 9 are diagrams illustrating a resonator 10 that is an example of a plurality of embodiments. FIG. 6 is a schematic diagram of the resonator 10. FIG. 7 is a planar view of the xy plane from the z direction. FIG. 8A is a cross-sectional view taken along line VIIIa-VIIIa illustrated in FIG. 7. FIG. 8B is a cross-sectional view taken along line VIIIb-VIIIb illustrated in FIG. 7. FIG. 9 is a cross-sectional view taken along line IX-IX illustrated in FIGS. 8A and 8B.

In the resonator 10 illustrated in FIGS. 6 to 9, the first conductive layer 41 includes a slot-type resonator as a first unit resonator 41X. The second conductive layer 42 includes a slot-type resonator as a second unit resonator 42X. The unit resonator 40X includes one first unit resonator 41X and four second divisional resonators 42Y. The unit structure 10X includes a unit resonator 40X as well as a part of the base 20 and a part of the fourth conductor 50 that overlap with the unit resonator 40X as viewed in the z direction.

Figure 10:
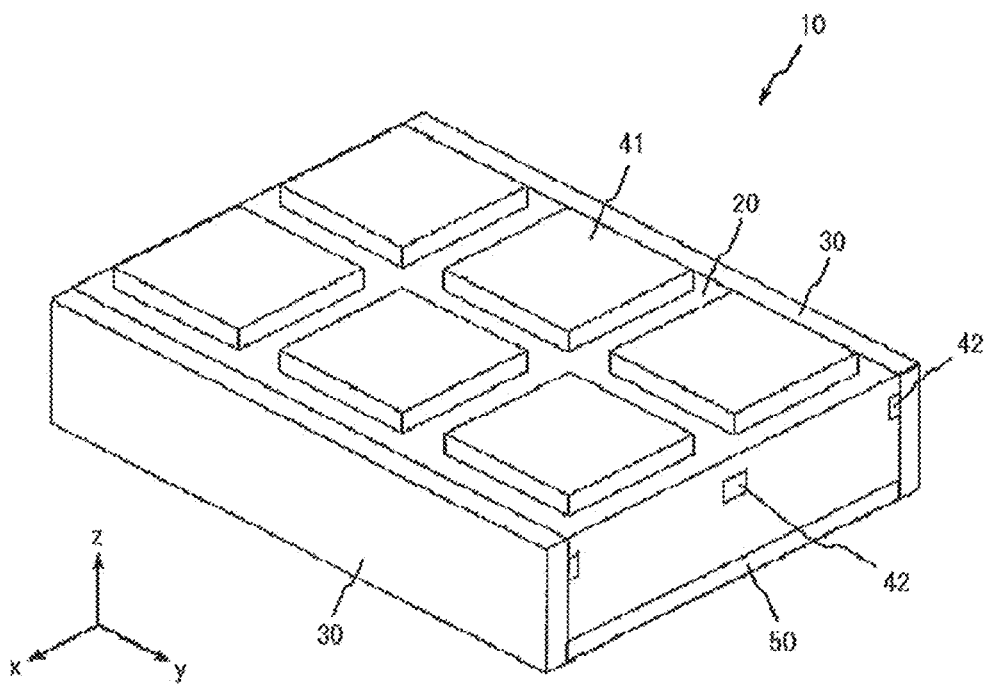
FIG. 10 is a perspective view illustrating an embodiment of a resonator.
Figure 11:
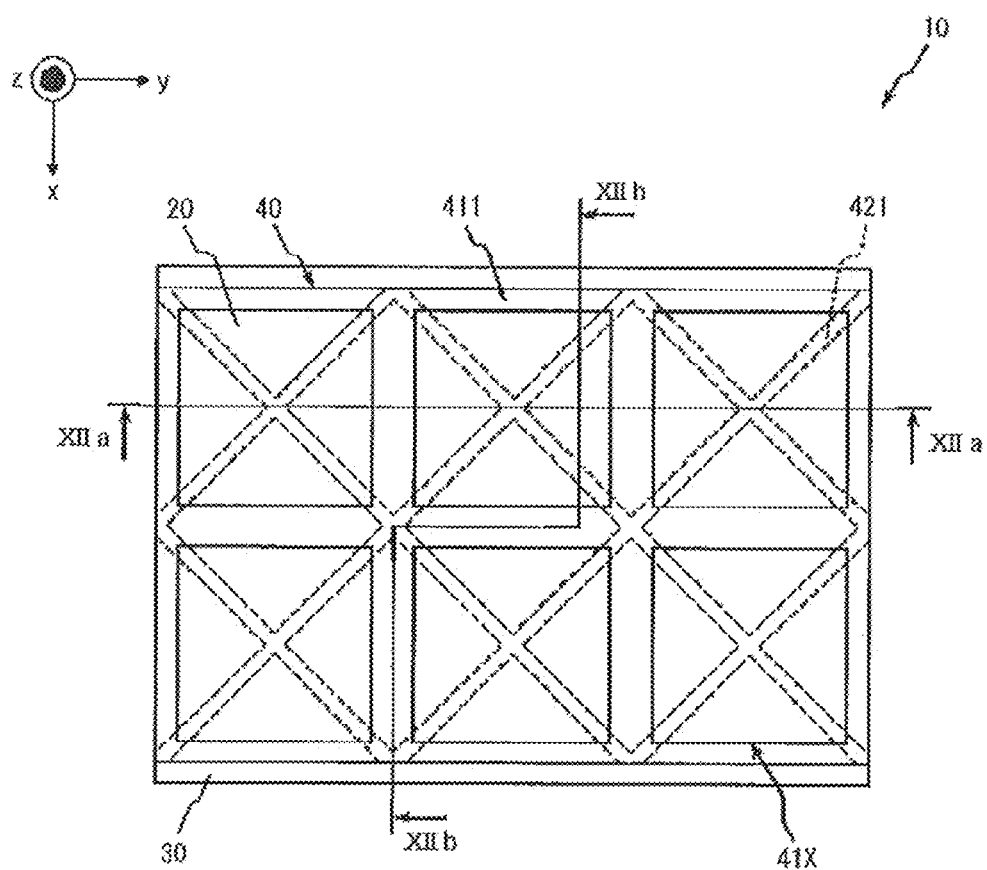
FIG. 11 is a planar view of the resonator illustrated in FIG. 10.
Figure 12A:
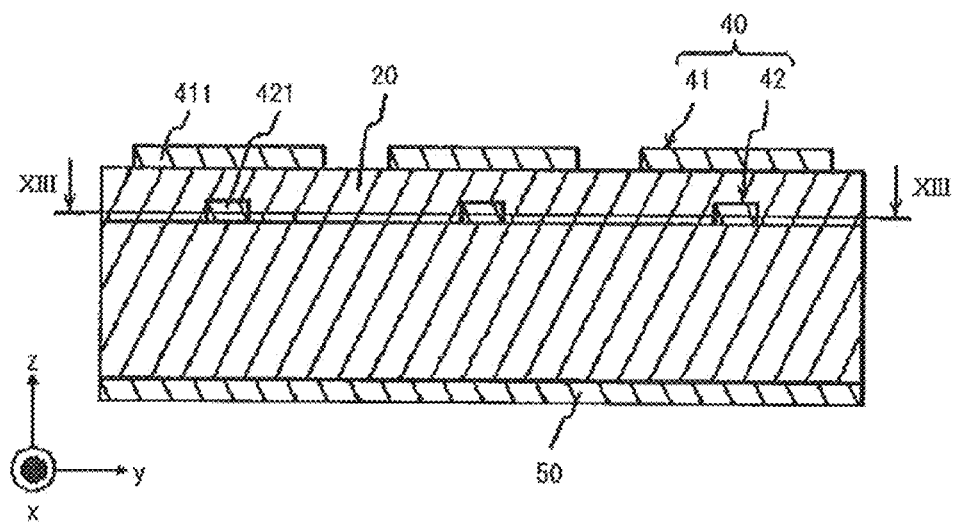
FIG. 12A is a cross-sectional view of the resonator illustrated in FIG. 10.
Figure 12B:
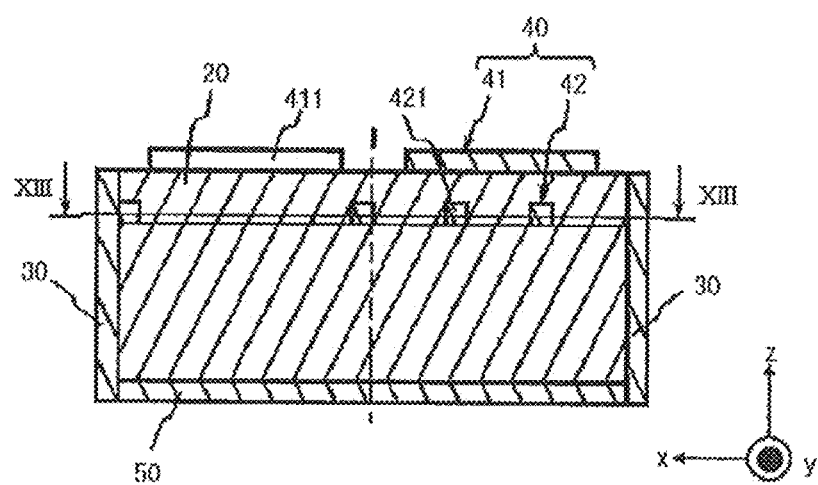
FIG. 12B is a cross-sectional view of the resonator illustrated in FIG. 10.
Figure 13:
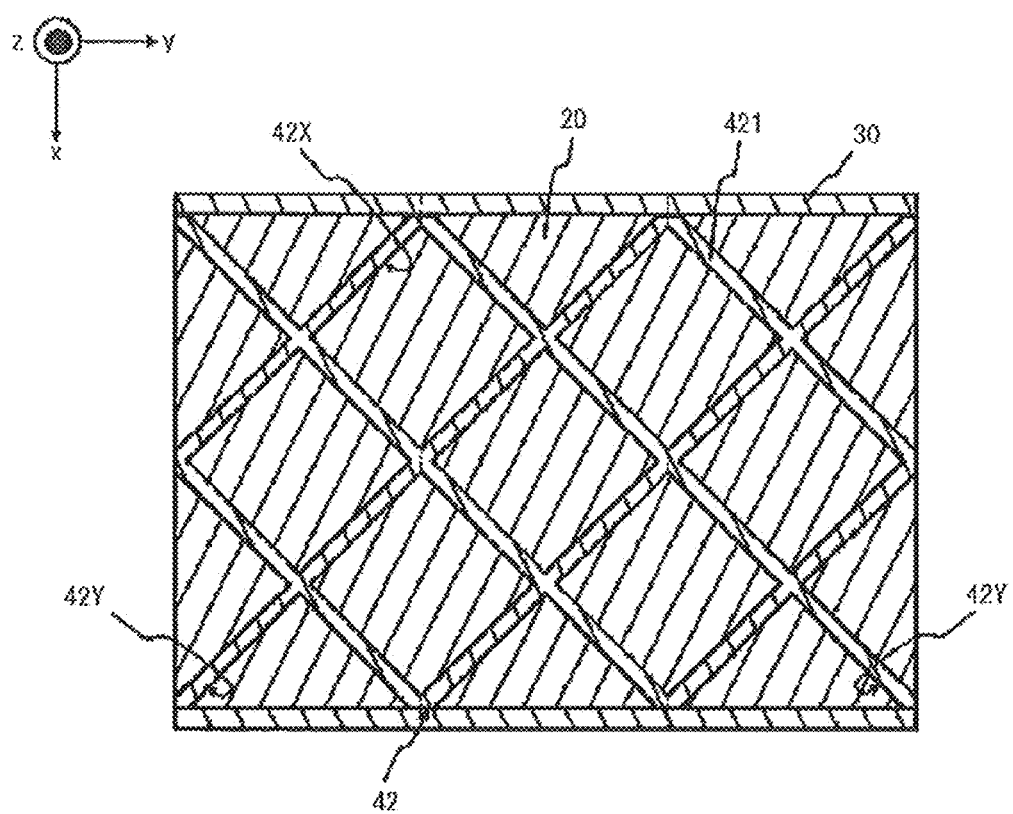
FIG. 13 is a cross-sectional view of the resonator illustrated in FIG. 10.

FIGS. 10 to 13 are diagrams illustrating a resonator 10 that is an example of a plurality of embodiments. FIG. 10 is a schematic diagram of the resonator 10. FIG. 11 is a planar view of the xy plane from the z direction. FIG. 12A is a cross-sectional view taken along line XIIa-XIIa illustrated in FIG. 11. FIG. 12B is a cross-sectional view taken along line XIIb-XIIb illustrated in FIG. 11. FIG. 13 is a cross-sectional view taken along line XIII-XIII illustrated in FIGS. 12A and 12B.

In the resonator 10 illustrated in FIGS. 10 to 13, the first conductive layer 41 includes a patch-type resonator as a first unit resonator 41X. The second conductive layer 42 includes a slot-type resonator as a second unit resonator 42X. The unit resonator 40X includes one first unit resonator 41X and four second divisional resonators 42Y. The unit structure 10X includes a unit resonator 40X as well as a part of the base 20 and a part of the fourth conductor 50 that overlap with the unit resonator 40X as viewed in the z direction.

Figure 14:
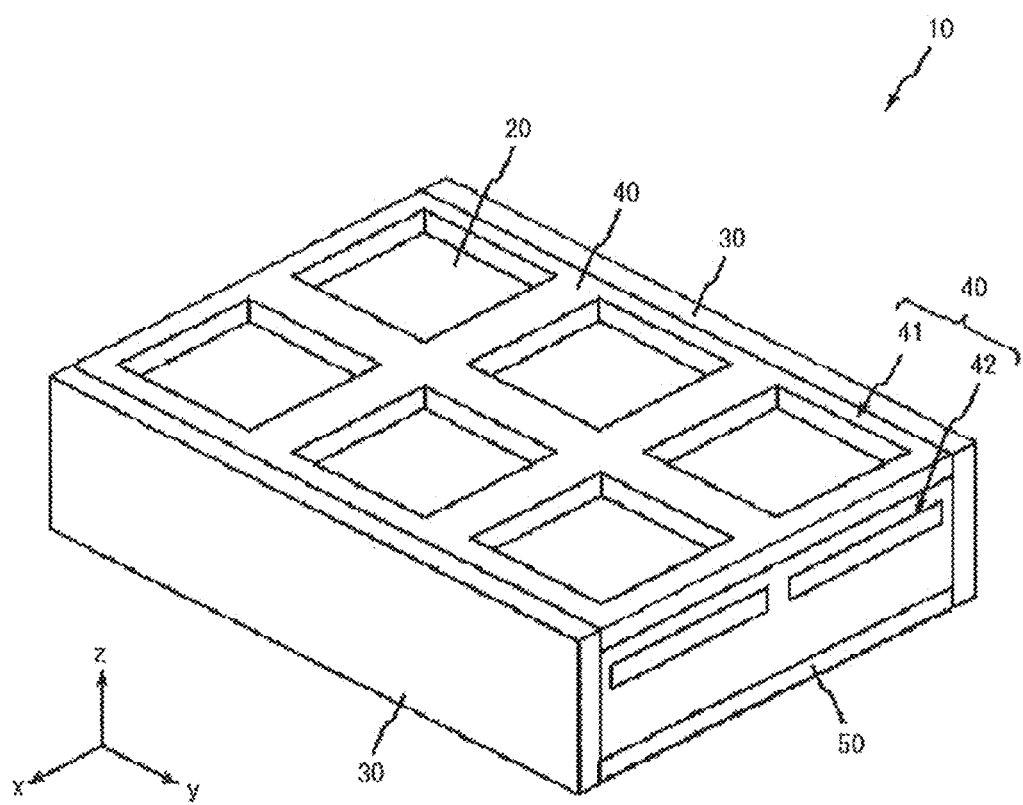
FIG. 14 is a perspective view illustrating an embodiment of a resonator.
Figure 15:
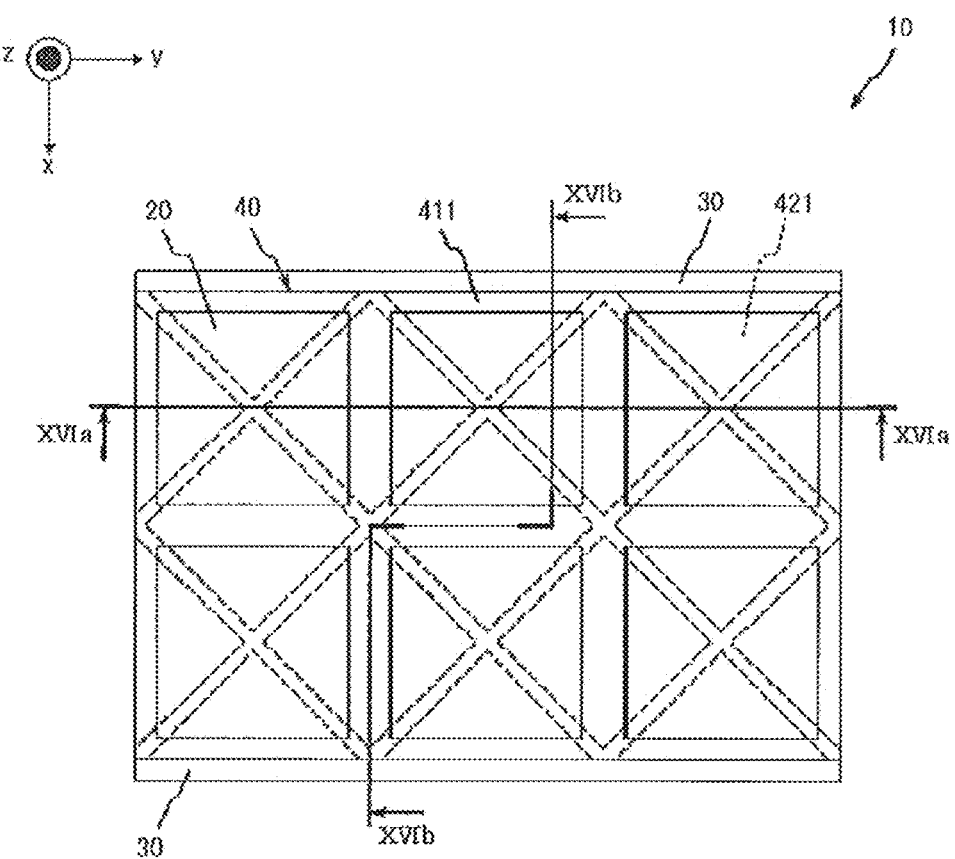
FIG. 15 is a planar view of the resonator illustrated in FIG. 14.
Figure 16A:
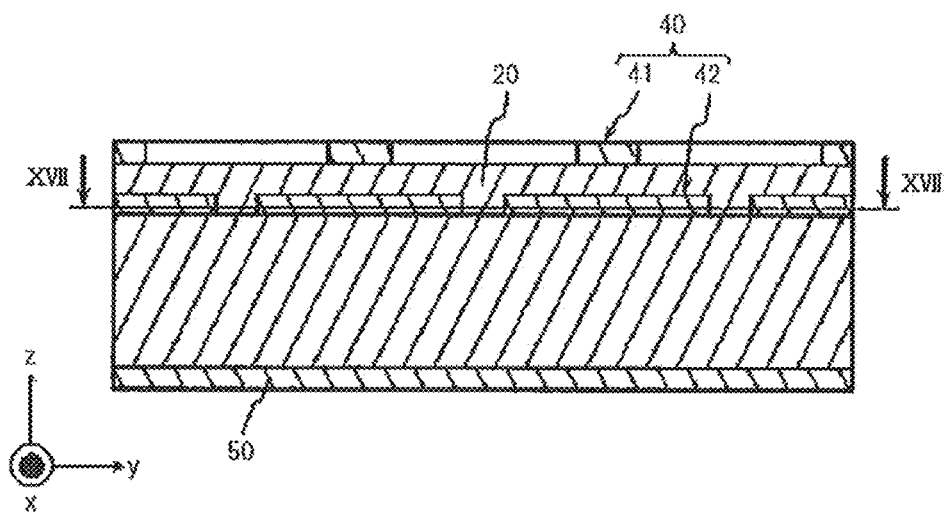
FIG. 16A is a cross-sectional view of the resonator illustrated in FIG. 14.
Figure 16B:
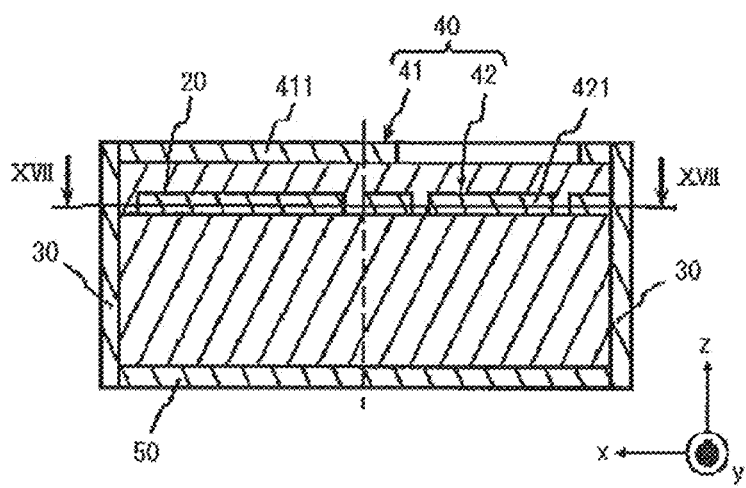
FIG. 16B is a cross-sectional view of the resonator illustrated in FIG. 14.
Figure 17:
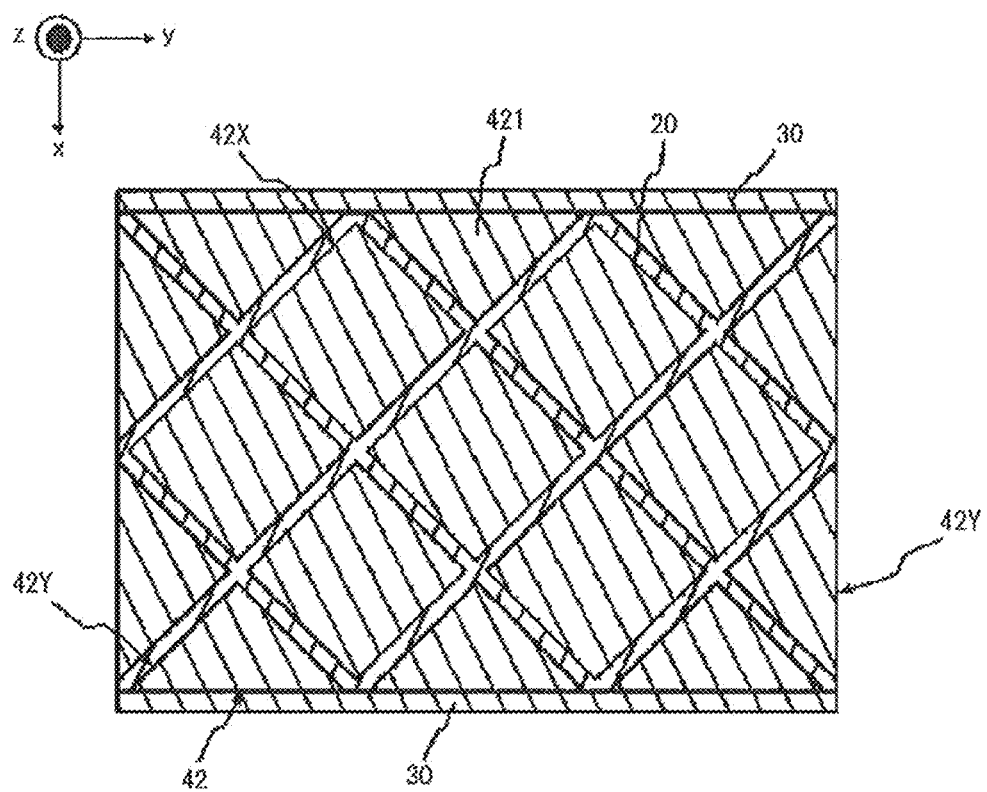
FIG. 17 is a cross-sectional view of the resonator illustrated in FIG. 14.

FIGS. 14 to 17 are diagrams illustrating a resonator 10 that is an example of a plurality of embodiments. FIG. 14 is a schematic diagram of the resonator 10. FIG. 15 is a planar view of the xy plane from the z direction. FIG. 16A is a cross-sectional view taken along line XVIa-XVIa illustrated in FIG. 15. FIG. 16B is a cross-sectional view taken along line XVIb-XVIb illustrated in FIG. 15. FIG. 17 is a cross-sectional view taken along line XVII-XVII illustrated in FIGS. 16A and 16B.

In the resonator 10 illustrated in FIGS. 14 to 17, the first conductive layer 41 includes a slot-type resonator as a first unit resonator 41X. The second conductive layer 42 includes a patch-type resonator as a second unit resonator 42X. The unit resonator 40X includes one first unit resonator 41X and four second divisional resonators 42Y. The unit structure 10X includes a unit resonator 40X as well as a part of the base 20 and a part of the fourth conductor 50 that overlap with the unit resonator 40X as viewed in the z direction.

Figure 18:
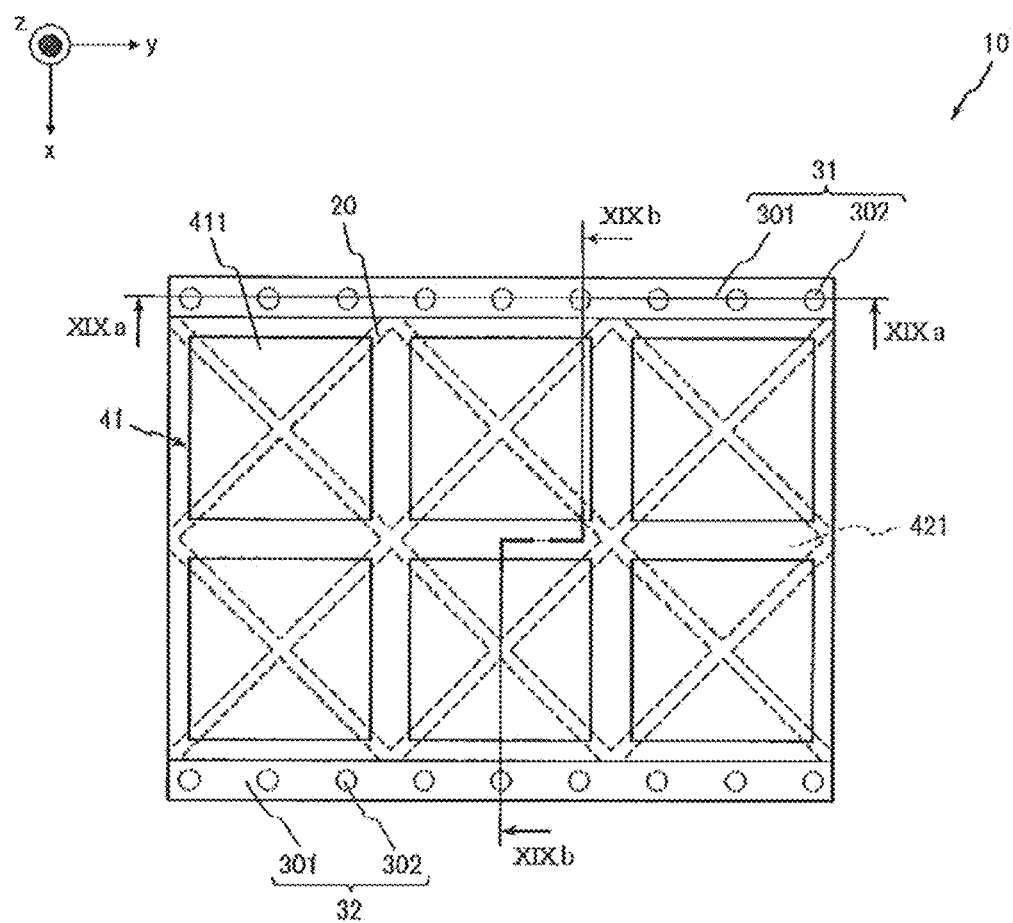
FIG. 18 is a planar view illustrating an embodiment of a resonator.
Figure 19A:
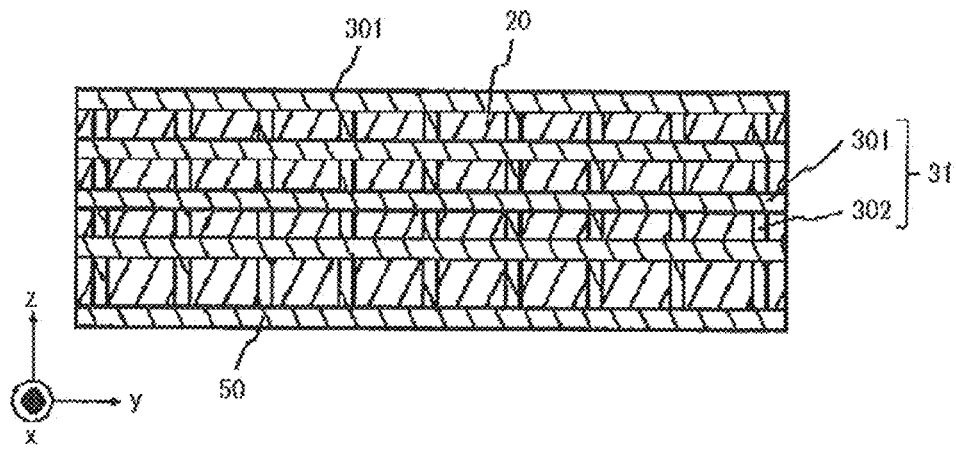
FIG. 19A is a cross-sectional view of the resonator illustrated in FIG. 18.
Figure 19B:
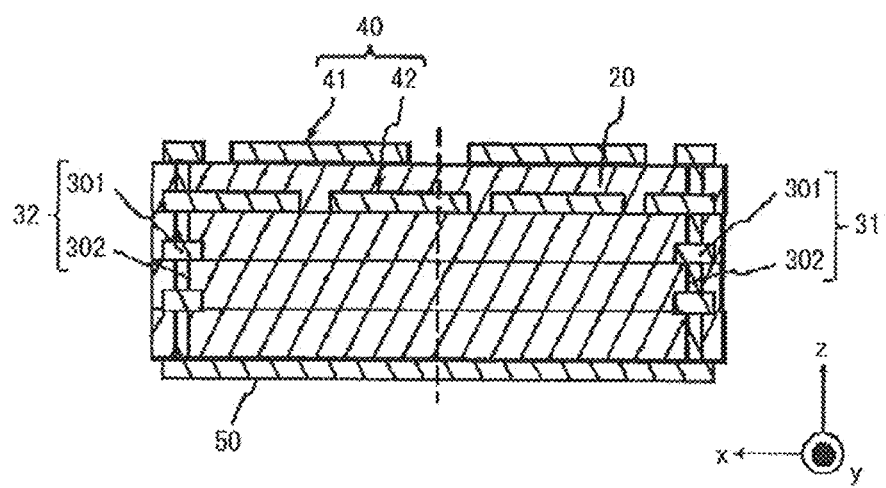
FIG. 19B is a cross-sectional view of the resonator illustrated in FIG. 18.

The resonator 10 in FIGS. 1 to 17 is illustrated by way of example. The configuration of the resonator 10 is not limited to the structures illustrated in FIGS. 1 to 17. FIG. 18 is a diagram illustrating a resonator 10 including pair conductors 30 in another configuration. FIG. 19A is a cross-sectional view taken along line XIXa-XIXa illustrated in FIG. 18. FIG. 19B is a cross-sectional view taken along line XIXb-XIXb illustrated in FIG. 18.

Figure 20:
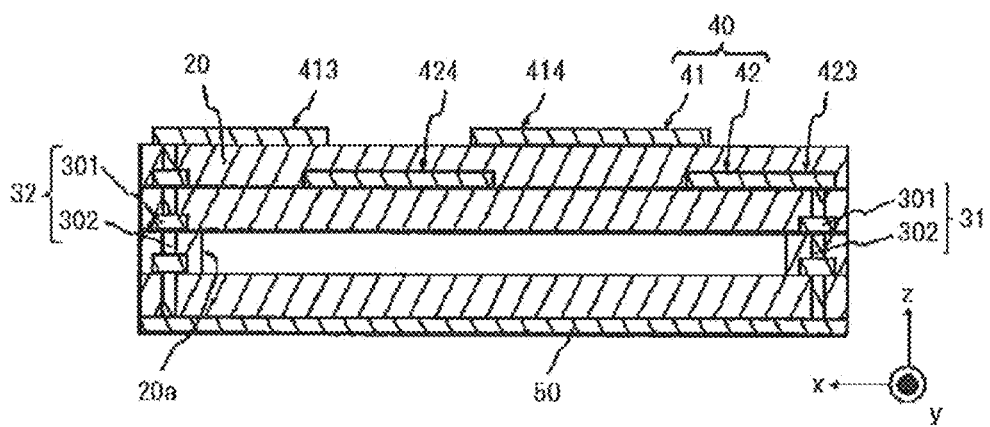
FIG. 20 is a cross-sectional view illustrating an embodiment of a resonator.

The base 20 in FIGS. 1 to 19A and 19B is illustrated by way of example. The configuration of the base 20 is not limited to the configuration illustrated in FIGS. 1 to 19A and 19B. The base 20 may include a cavity 20a in the inside as illustrated in FIG. 20. In the z direction, the cavity 20a is positioned between the third conductor 40 and the fourth conductor 50. The dielectric constant of the cavity 20a is lower than the dielectric constant of the base 20. When the base 20 has the cavity 20a, the electromagnetic distance between the third conductor 40 and the fourth conductor 50 can be reduced.

Figure 21:
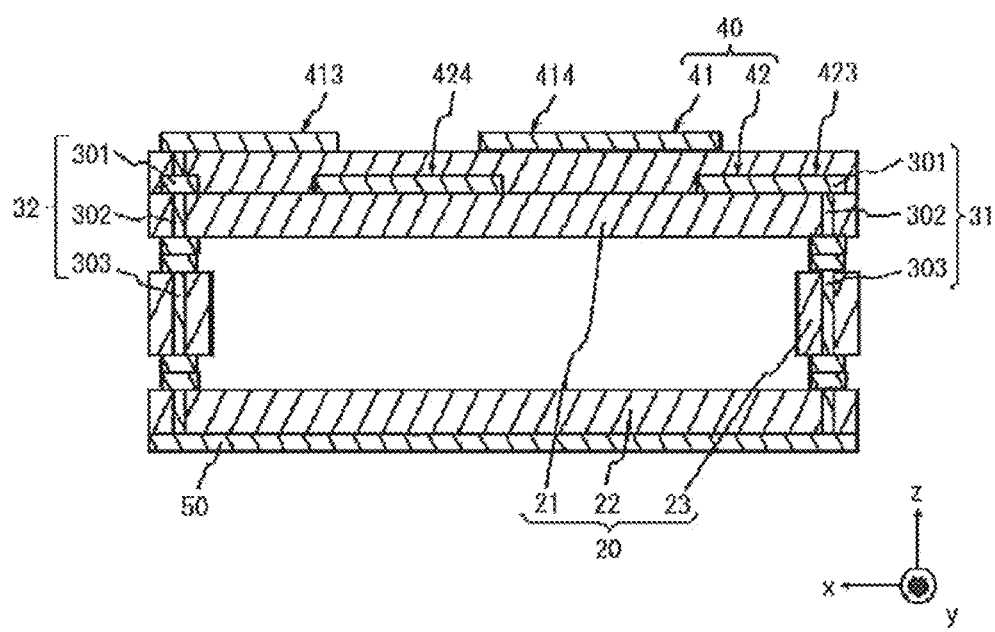
FIG. 21 is a planar view of an embodiment of a resonator.

As illustrated in FIG. 21, the base 20 may include a plurality of members. The base 20 may include a first base 21, a second base 22, and a connector 23. The first base 21 and the second base 22 may be mechanically connected to each other through the connector 23. The connector 23 may include a sixth conductor 303 in the inside. The sixth conductor 303 is electrically connected to the fifth conductive layer 301 or the fifth conductor 302. The sixth conductor 303 is combined with the fifth conductive layer 301 and the fifth conductor 302 into a first conductor 31 or a second conductor 32.

Figure 22A:
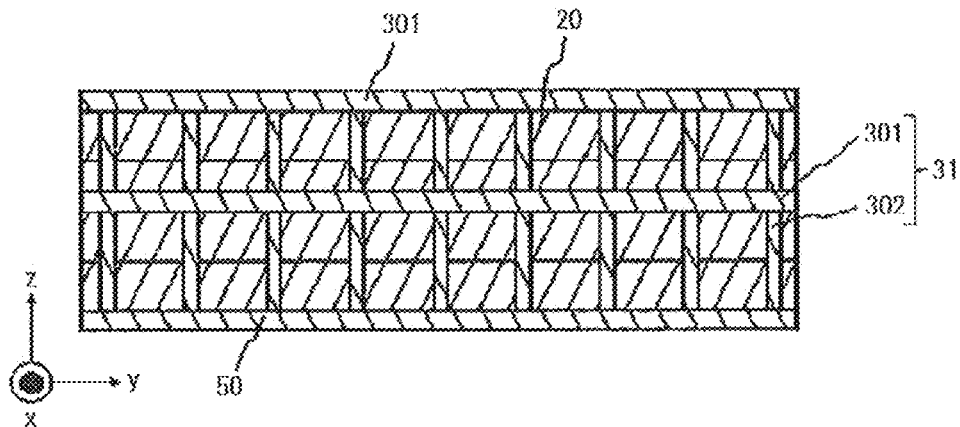
FIG. 22A is a cross-sectional view illustrating an embodiment of a resonator.
Figure 22B:
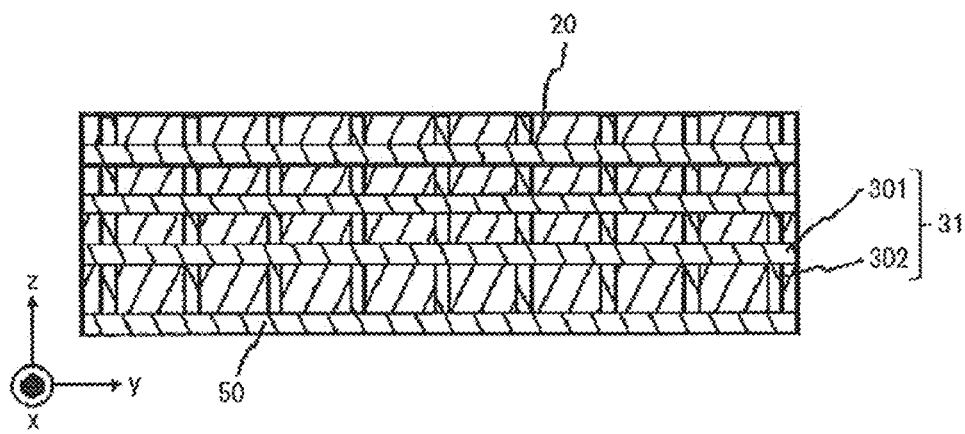
FIG. 22B is a cross-sectional view illustrating an embodiment of a resonator.
Figure 22C:
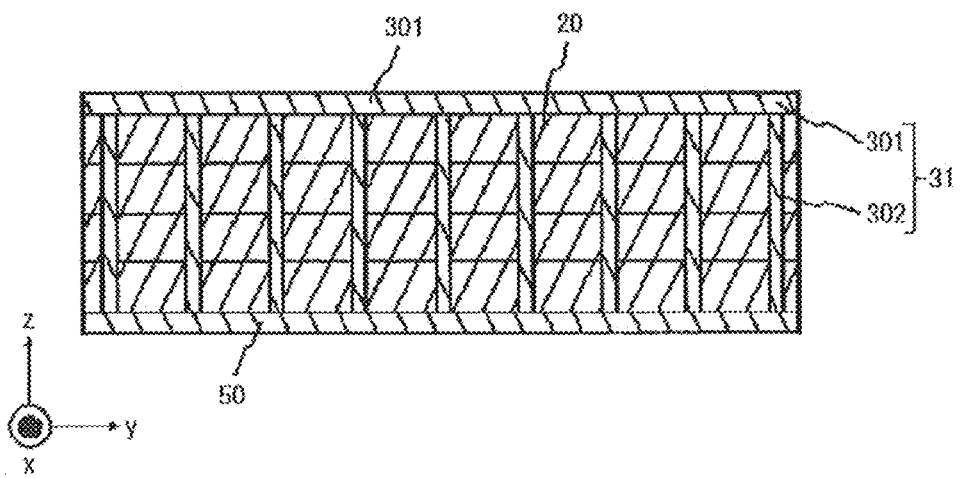
FIG. 22C is a cross-sectional view illustrating an embodiment of a resonator.

The pair conductors 30 in FIGS. 1 to 21 are illustrated by way of example. The configuration of the pair conductors 30 is not limited to the configuration illustrated in FIGS. 1 to 21. FIGS. 22 to 28 are diagrams illustrating a resonator 10 including pair conductors 30 in another configuration. FIGS. 22A, 22B, and 22C are cross-sectional views corresponding to FIG. 19A. As illustrated in FIG. 22A, the number of fifth conductive layers 301 may be changed as appropriate. As illustrated in FIG. 22B, the fifth conductive layer 301 is not necessarily positioned on the base 20. As illustrated in FIG. 22C, the fifth conductive layer 301 is not necessarily positioned in the base 20.

Figure 23:
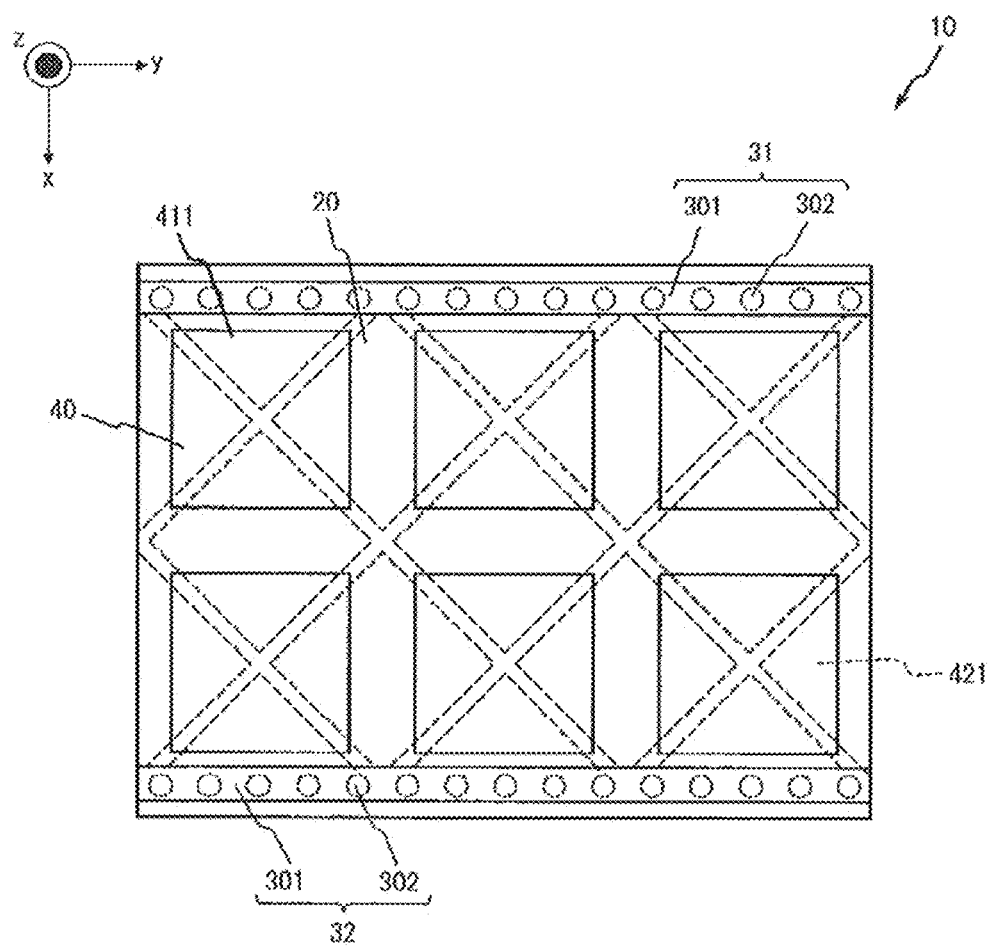
FIG. 23 is a planar view of an embodiment of a resonator.
Figure 24:
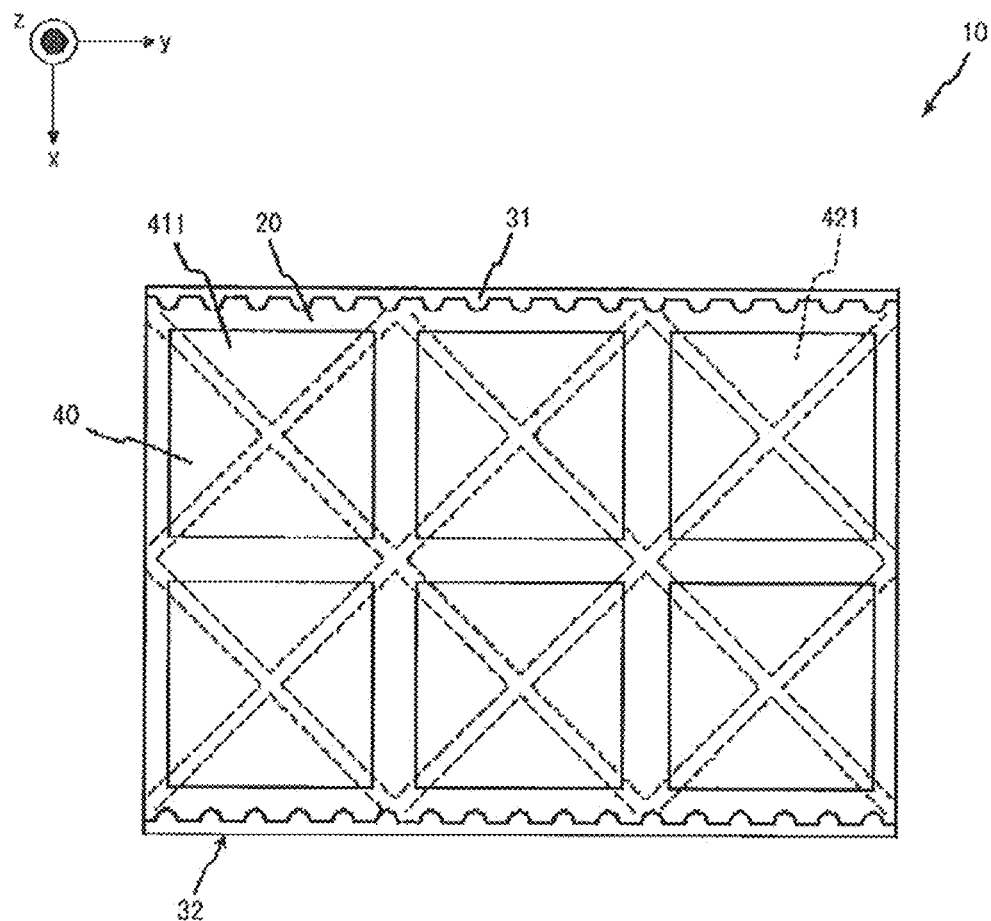
FIG. 24 is a planar view of an embodiment of a resonator.

FIG. 23 is a plan view corresponding to FIG. 18. As illustrated in FIG. 23, the resonator 10 may have the fifth conductor 302 away from the boundary of the unit resonator 40X. FIG. 24 is a plan view corresponding to FIG. 18. As illustrated in FIG. 24, two pair conductors 30 each may have protrusions protruding toward the other pair conductor 30 to be paired. Such a resonator 10 may be formed by, for example, applying metal paste to the base 20 having depressions and hardening the applied metal paste.

Figure 25:
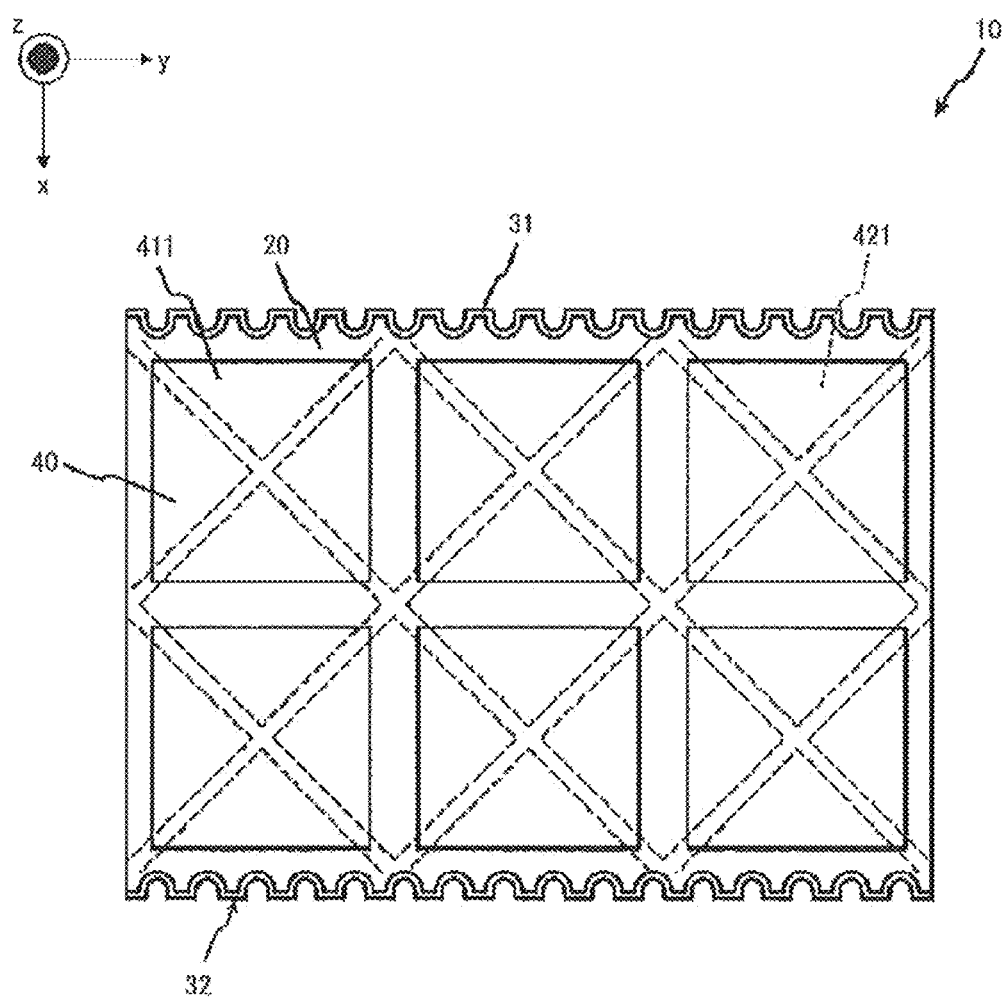
FIG. 25 is a planar view of an embodiment of a resonator.

FIG. 25 is a plan view corresponding to FIG. 18. As illustrated in FIG. 25, the base 20 may have depressions. As illustrated in FIG. 25, the pair conductors 30 have depressions recessed from the outer surface to the inside in the x direction. As illustrated in FIG. 25, the pair conductors 30 extend along the surfaces of the base 20. Such a resonator 10 may be formed by, for example, spraying a fine metal material to the base 20 having depressions.

Figure 26:
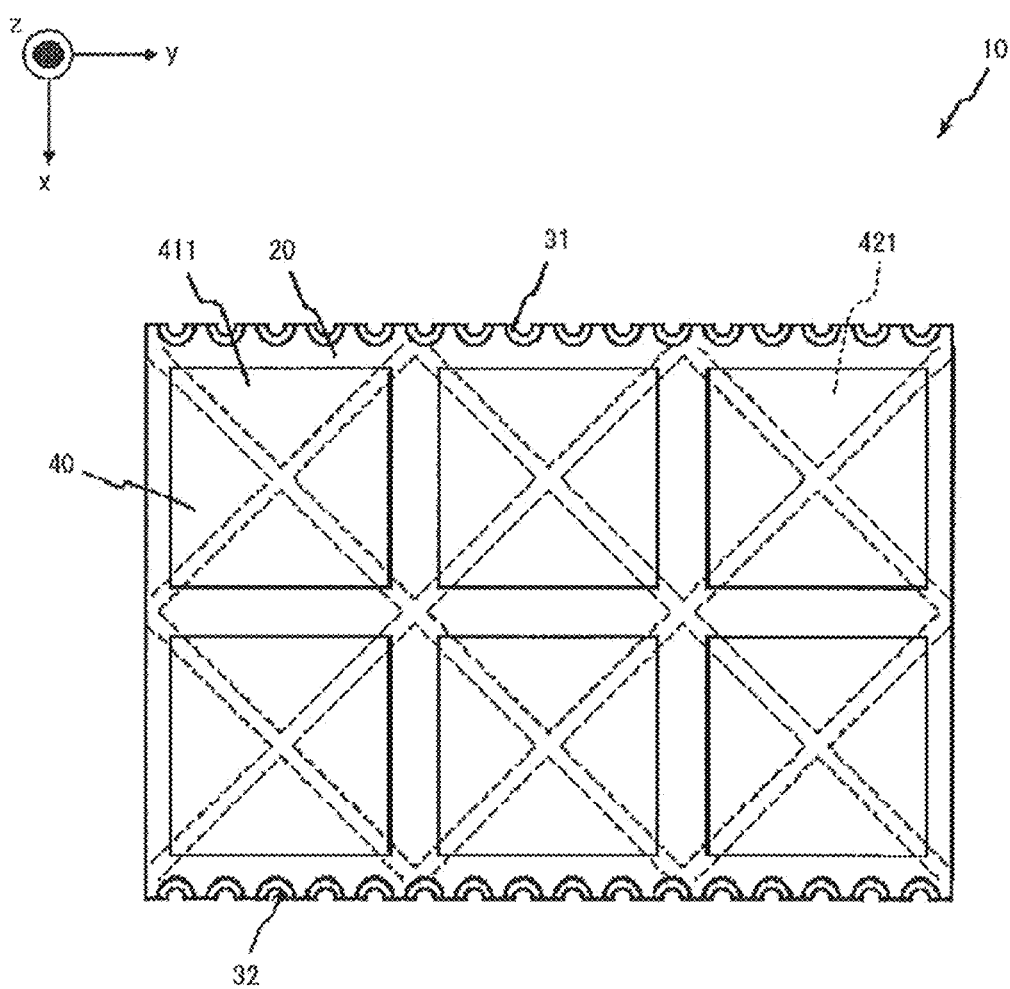
FIG. 26 is a planar view of an embodiment of a resonator.

FIG. 26 is a plan view corresponding to FIG. 18. As illustrated in FIG. 26, the base 20 may have depressions. As illustrated in FIG. 26, the pair conductors 30 have depressions recessed from the outer surface to the inside in the x direction. As illustrated in FIG. 26, the pair conductors 30 extend along the depressions of the base 20. Such a resonator 10 may be produced by, for example, dividing a motherboard along an alignment of through hole conductors. Such pair conductors 30 may be called end-face through holes.

Figure 27:
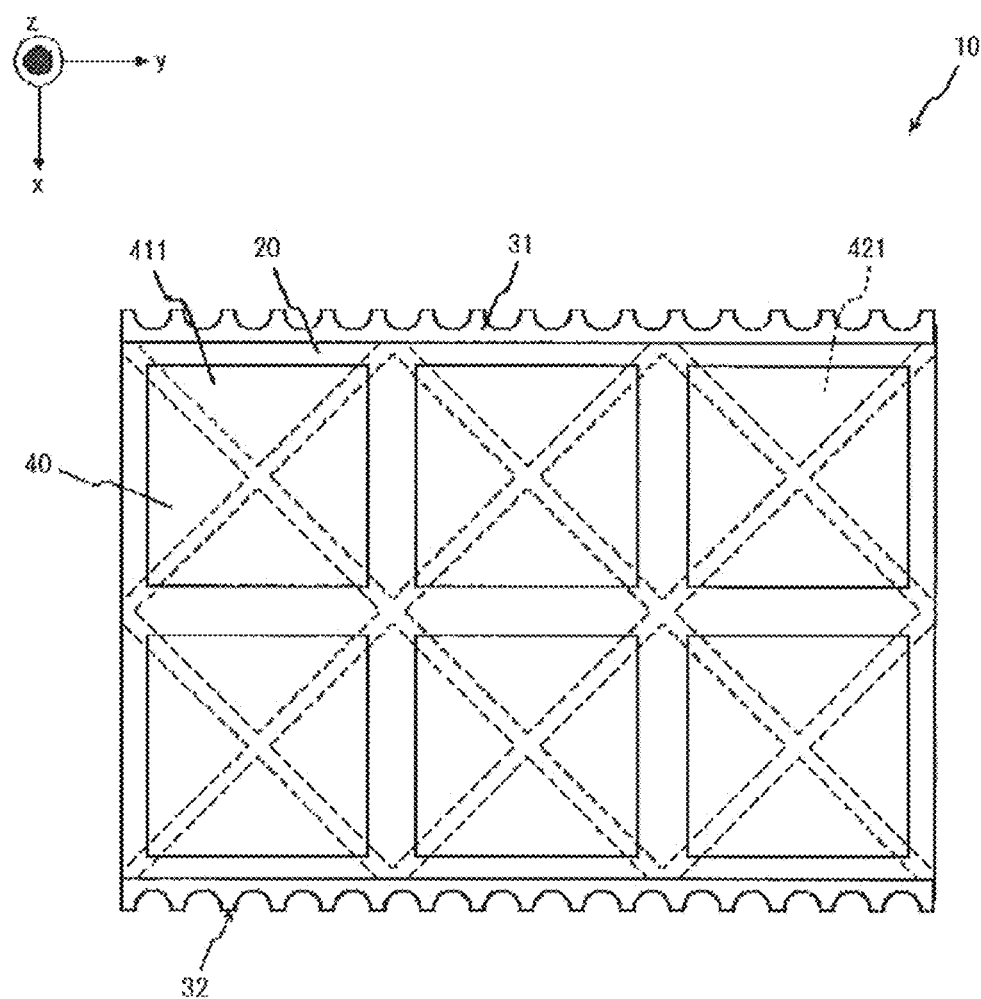
FIG. 27 is a planar view of an embodiment of a resonator.

FIG. 27 is a plan view corresponding to FIG. 18. As illustrated in FIG. 27, the base 20 may have depressions. As illustrated in FIG. 27, the pair conductors 30 have depressions recessed from the outer surface to the inside in the x direction. Such a resonator 10 may be produced by, for example, dividing a motherboard along an alignment of through hole conductors. Such pair conductors 30 may be called end-face through holes.

Figure 28:
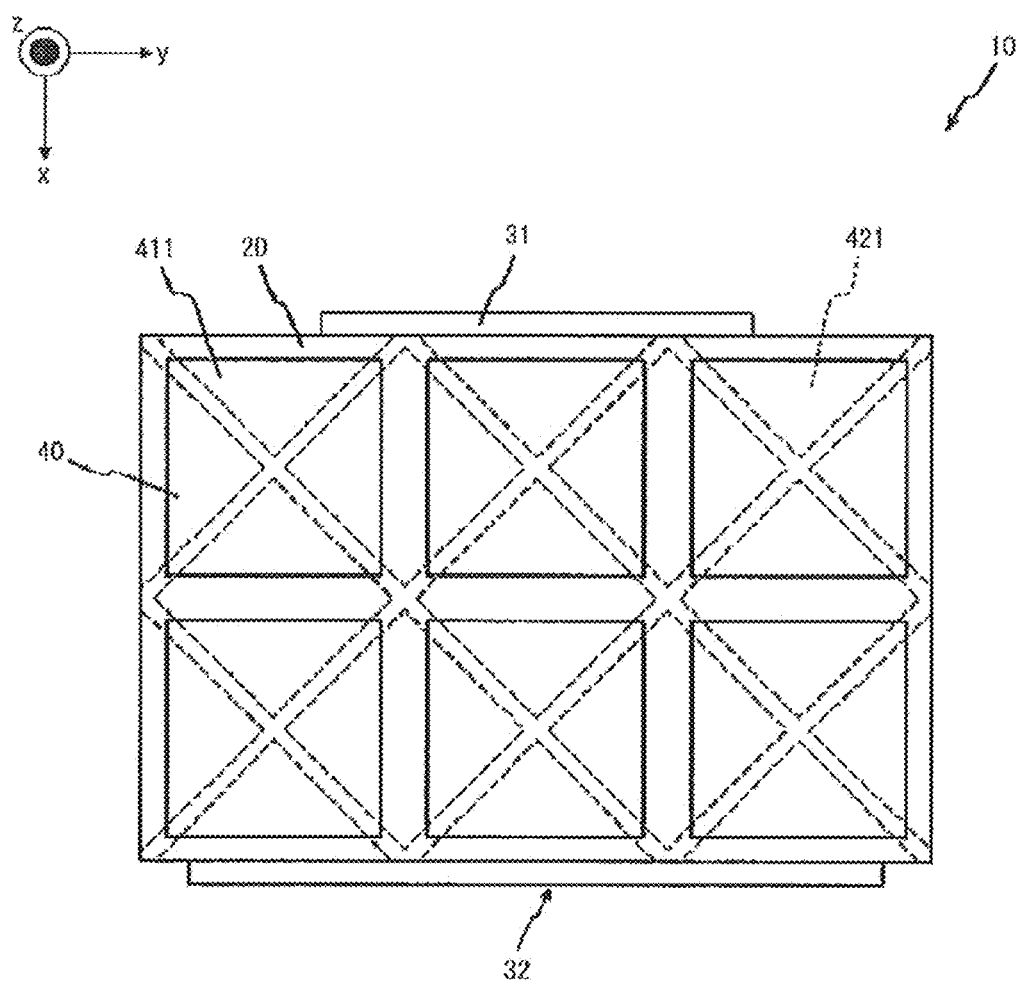
FIG. 28 is a planar view of an embodiment of a resonator.

FIG. 28 is a plan view corresponding to FIG. 18. As illustrated in FIG. 28, the length in the x direction of the pair conductors 30 may be shorter than that of the base 20. The configuration of the pair conductors 30 is not limited to these. Two pair conductors 30 may have configurations different from each other. For example, one pair conductor 30 may include a fifth conductive layer 301 and a fifth conductor 302, and the other pair conductor 30 may be end-face through holes.

Figure 29A:
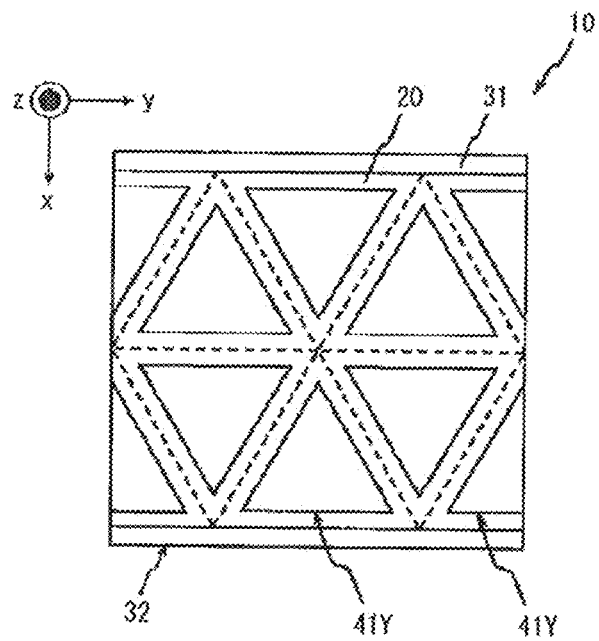
FIG. 29A is a planar view of an embodiment of a resonator.
Figure 29B:
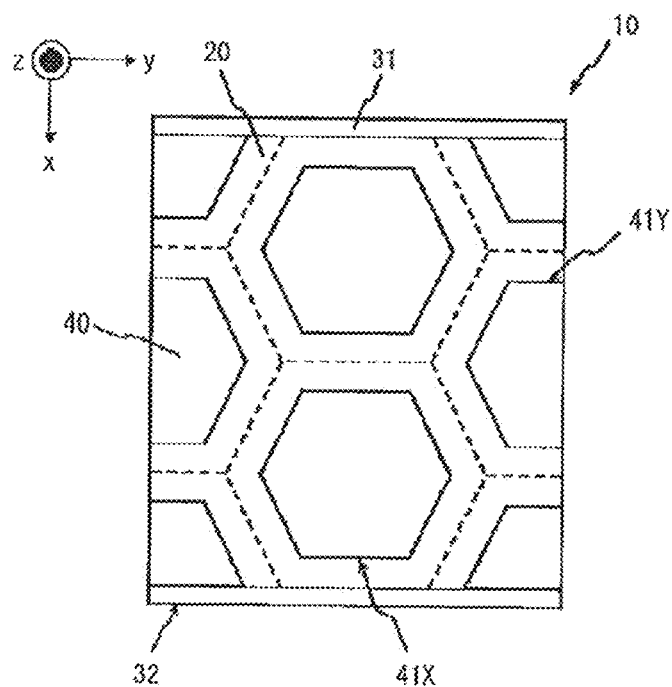
FIG. 29B is a planar view of an embodiment of a resonator.
Figure 30:
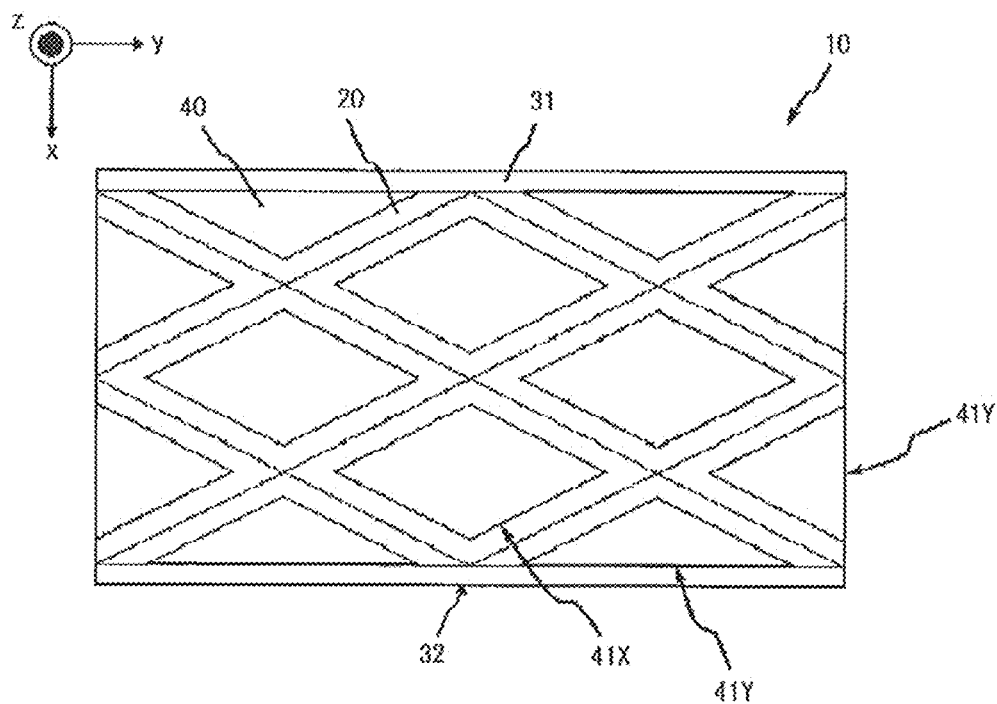
FIG. 30 is a planar view of an embodiment of a resonator.

The third conductor 40 in FIGS. 1 to 28 is illustrated by way of example. The configuration of the third conductor 40 is not limited to the configurations illustrated in FIGS. 1 to 28. The unit resonator 40X, the first unit resonator 41X, and the second unit resonator 42X are not limited to a quadrature shape. The unit resonator 40X, the first unit resonator 41X, and the second unit resonator 42X may be called a unit resonator 40X and the like. For example, the unit resonator 40X and the like may be triangular as illustrated in FIG. 29A or may be hexagonal as illustrated in FIG. 29B. The sides of the unit resonator 40X and the like may extend in directions different from the x direction and the y direction as illustrated in FIG. 30. The third conductor 40 may have the second conductive layer 42 positioned on the base 20 and the first conductive layer 41 positioned in the base 20. In the third conductor 40, the second conductive layer 42 may be positioned farther from the fourth conductor 50 than the first conductive layer 41 is.

Figure 31A:
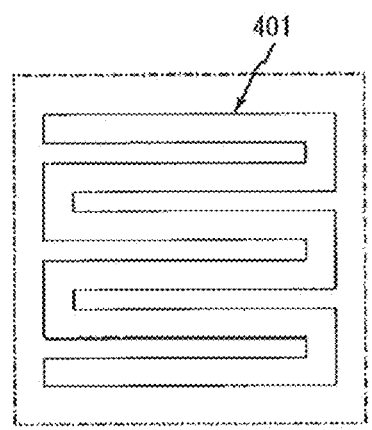
FIG. 31A is a schematic diagram illustrating an example of a resonator.
Figure 31B:
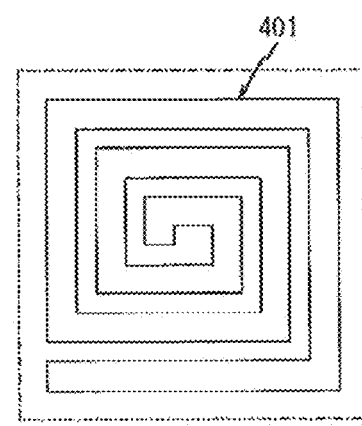
FIG. 31B is a schematic diagram illustrating an example of a resonator.
Figure 31C:
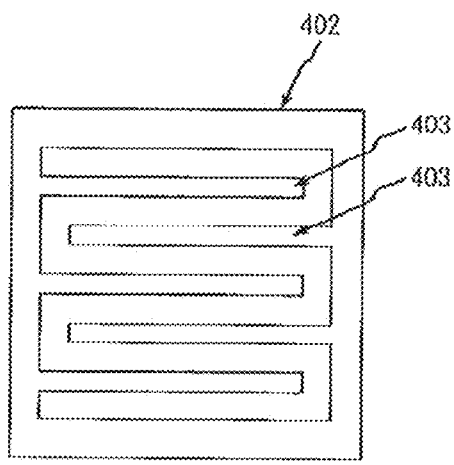
FIG. 31C is a schematic diagram illustrating an example of a resonator.
Figure 31D:
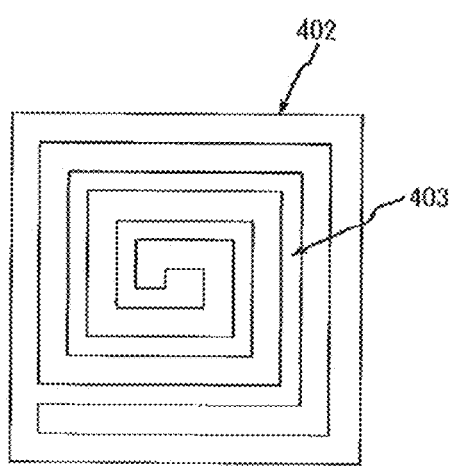
FIG. 31D is a schematic diagram illustrating an example of a resonator.
Figure 32A:
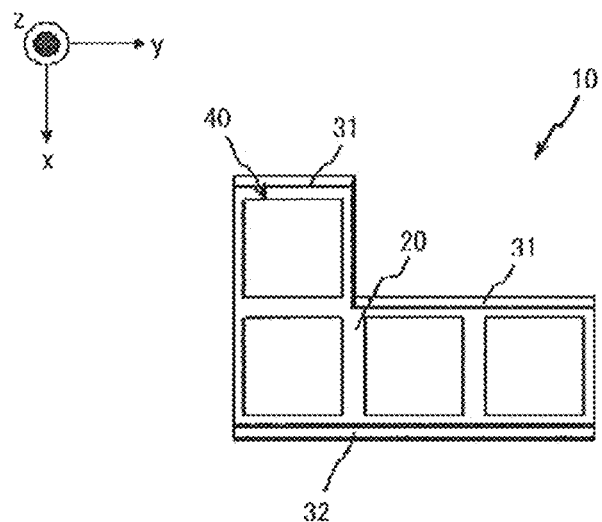
FIG. 32A is a planar view of an embodiment of a resonator.
Figure 32B:
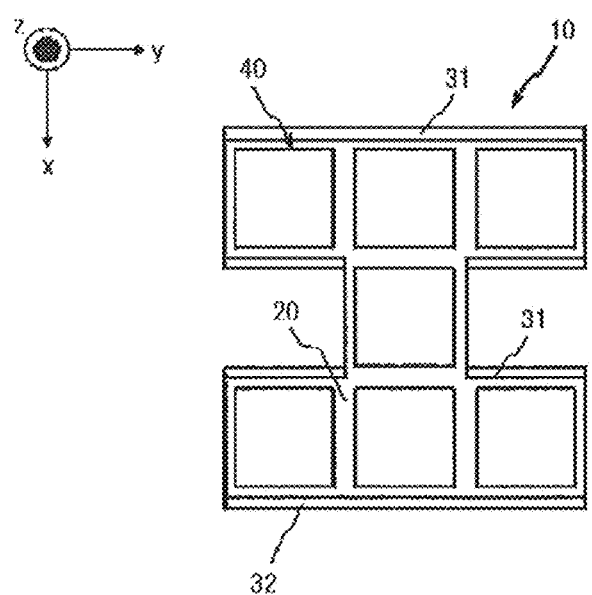
FIG. 32B is a planar view of an embodiment of a resonator.
Figure 32C:
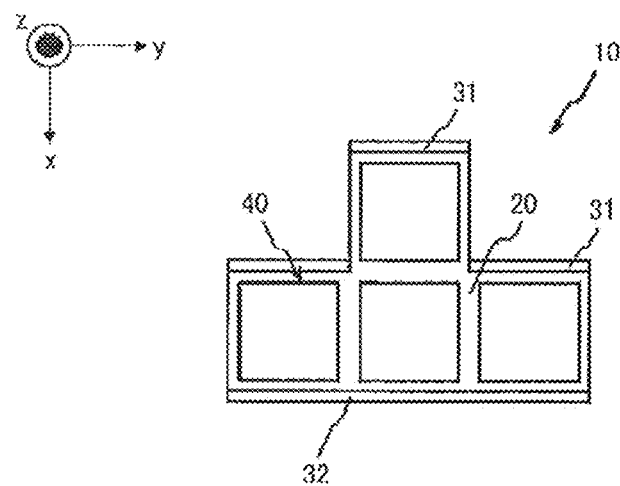
FIG. 32C is a planar view of an embodiment of a resonator.
Figure 32D:
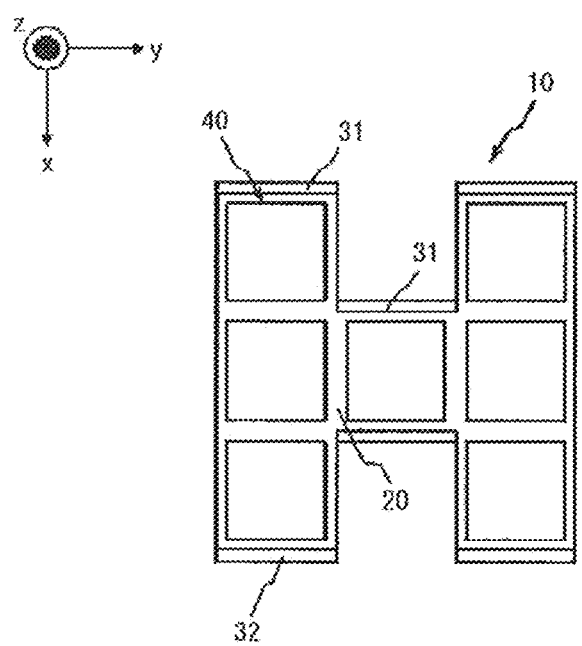
FIG. 32D is a planar view of an embodiment of a resonator.
Figure 33A:
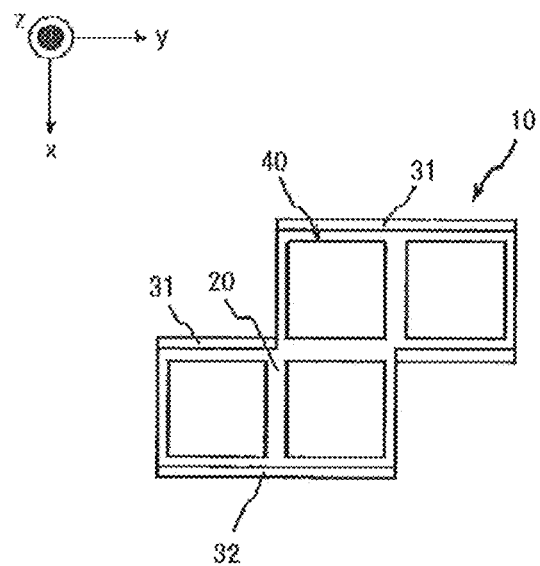
FIG. 33A is a planar view of an embodiment of a resonator.
Figure 33B:
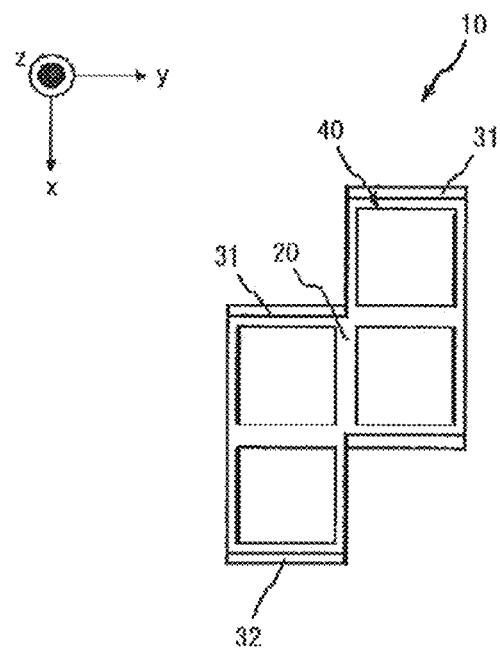
FIG. 33B is a planar view of an embodiment of a resonator.
Figure 33C:
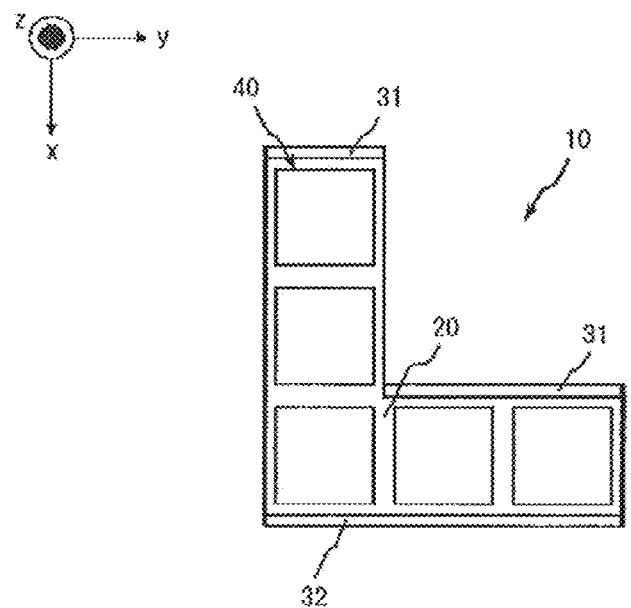
FIG. 33C is a planar view of an embodiment of a resonator.
Figure 33D:
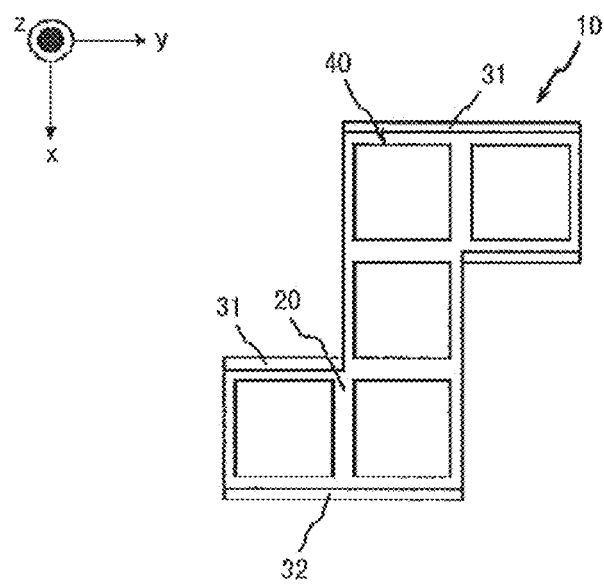
FIG. 33D is a planar view of an embodiment of a resonator.
Figure 34A:
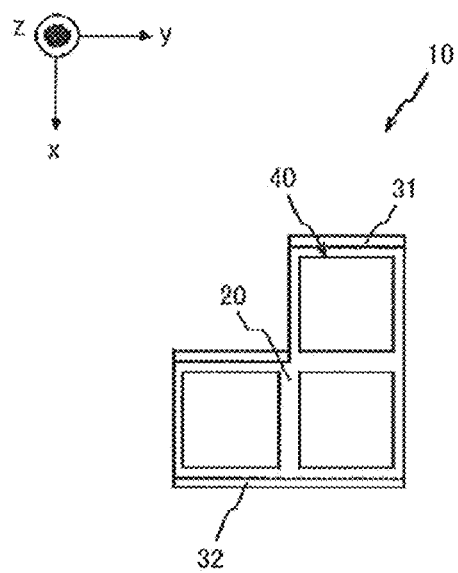
FIG. 34A is a planar view of an embodiment of a resonator.
Figure 34B:
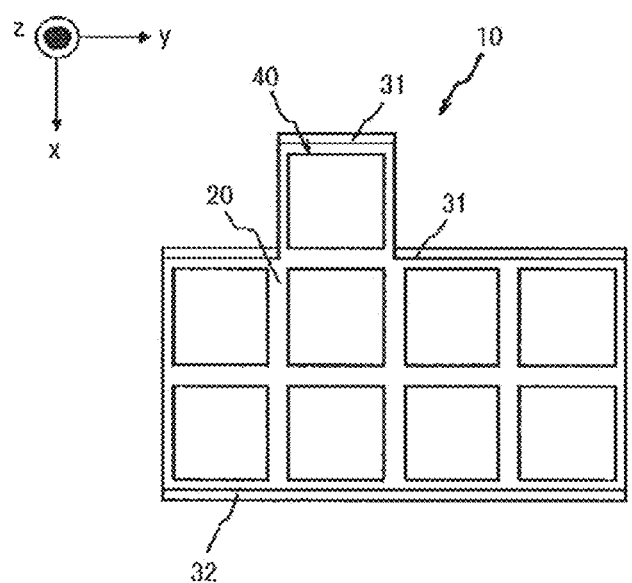
FIG. 34B is a planar view of an embodiment of a resonator.
Figure 34C:
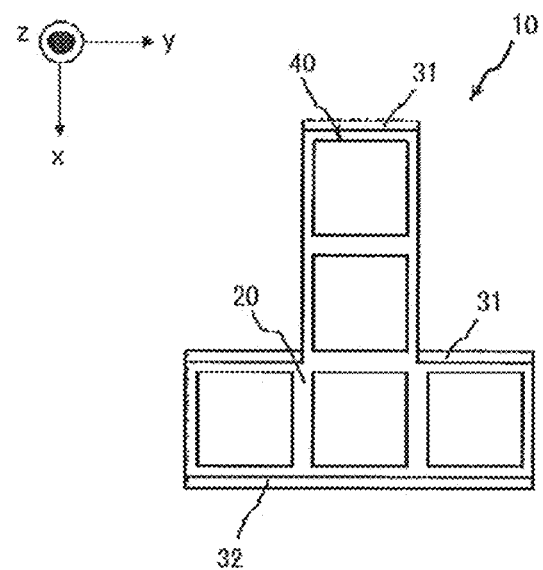
FIG. 34C is a planar view of an embodiment of a resonator.
Figure 34D:
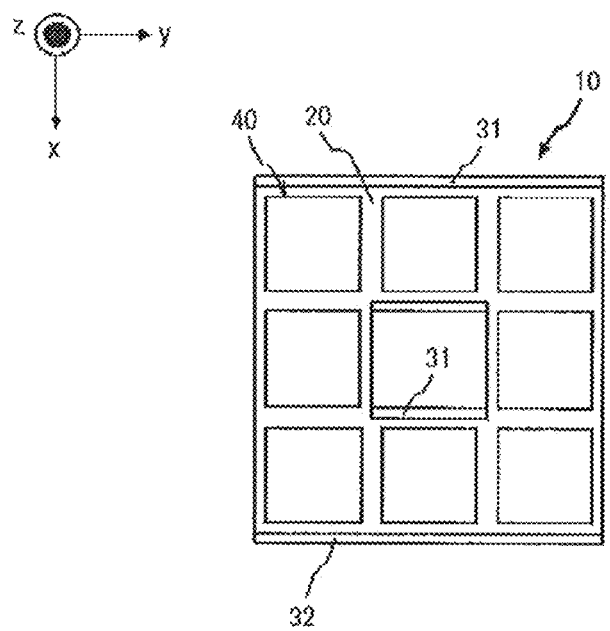
FIG. 34D is a planar view of an embodiment of a resonator.

The third conductor 40 in FIGS. 1 to 30 is illustrated by way of example. The configuration of the third conductor 40 is not limited to the configurations illustrated in FIGS. 1 to 30. The resonator including the third conductor 40 may be a line-type resonator 401. Illustrated in FIG. 31A is a meander line-type resonator 401. Illustrated in FIG. 31B is a spiral-type resonator 401. The resonator of the third conductor 40 may be a slot-type resonator 402. The slot-type resonator 402 may have one or more seventh conductors 403 in an opening. The seventh conductor 403 in an opening has one end opened and the other end electrically connected to a conductor that defines the opening. The unit slot illustrated in FIG. 31C has five seventh conductors 403 positioned in the opening. The unit slot has a shape corresponding to a meander line with the seventh conductors 403. The unit slot illustrated in FIG. 31D has one seventh conductor 403 positioned in an opening. The unit slot has a shape corresponding to a spiral with the seventh conductor 403.

The configurations of the resonator 10 in FIGS. 1 to 31A, 31B, 31C, and 31D are illustrated by way of example. The configuration of the resonator 10 is not limited to the configurations illustrated in FIGS. 1 to 31A, 31B, 31C, and 31D. For example, the resonator 10 may include three or more pair conductors 30. For example, one pair conductor 30 may be opposed to two pair conductors 30 in the x direction. The two pair conductors 30 differ in distance from the one pair conductor 30. For example, the resonator 10 may include two pairs of pair conductors 30. Two pairs of pair conductors 30 may differ in distance of each pair and length of each pair. The resonator 10 may include five or more first conductors. A unit structure 10X of the resonator 10 may be aligned with another unit structure 10X in the y direction. The unit structure 10X of the resonator 10 may be aligned with another unit structure 10X in the x direction without the pair conductors 30 interposed therebetween. FIGS. 32A to 34A, 32B to 34B, 32C to 34C, and 32D to 34D are diagrams illustrating examples of the resonator 10. In the resonator 10 illustrated in FIGS. 32A to 34A, 32B to 34B, 32C to 34C, and 32D to 34D, the unit resonator 40X of the unit structure 10X is a square, but the embodiments are not limited thereto.

Figure 35:
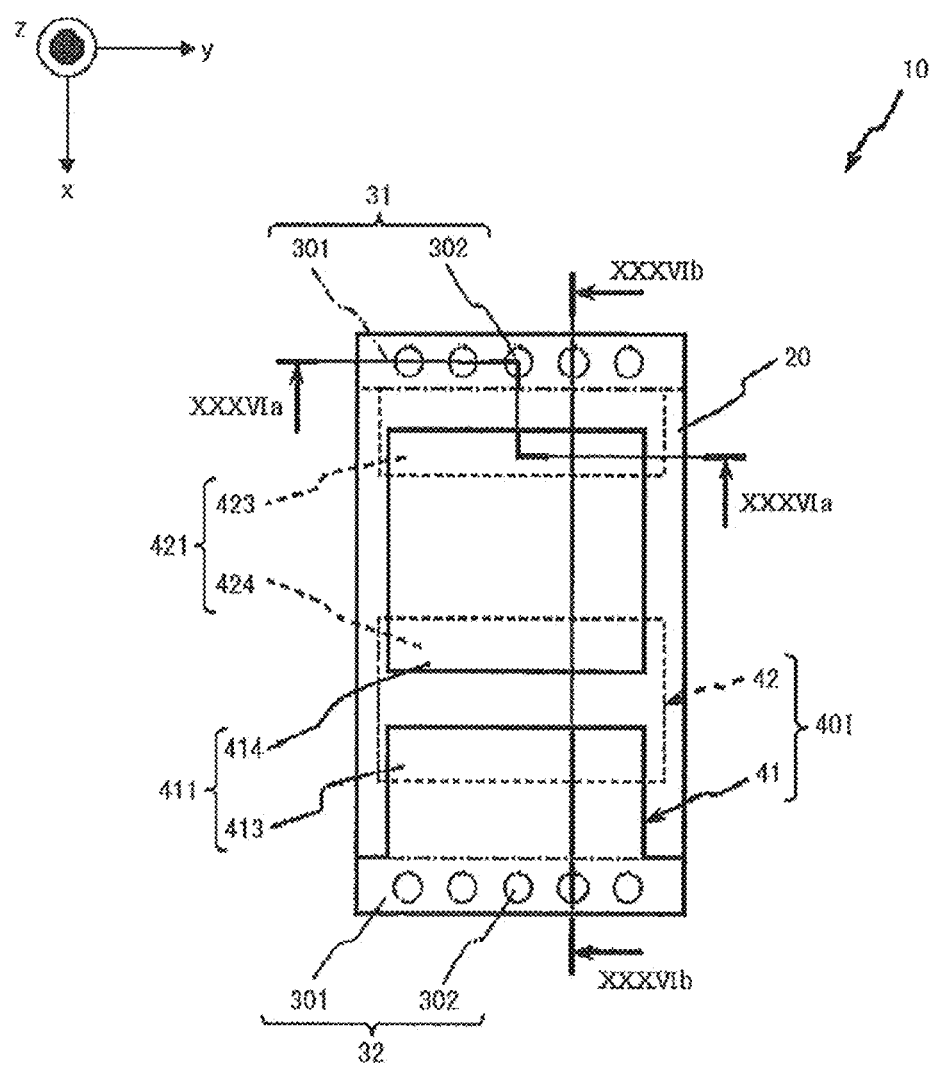
FIG. 35 is a planar view of an embodiment of a resonator.
Figure 36A:
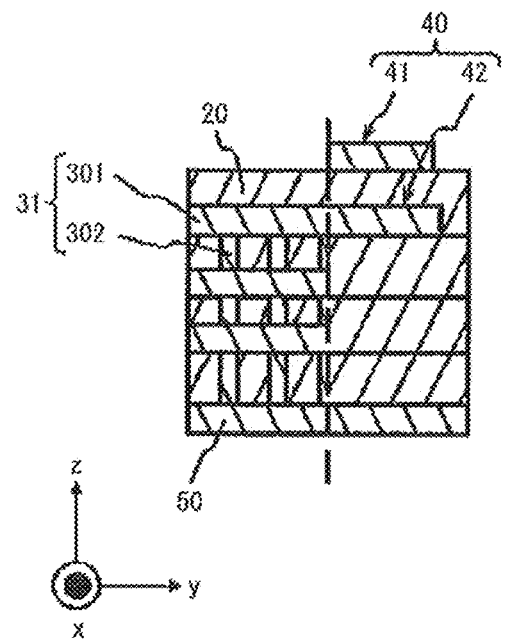
FIG. 36A is a cross-sectional view illustrating an embodiment of a resonator.
Figure 36B:
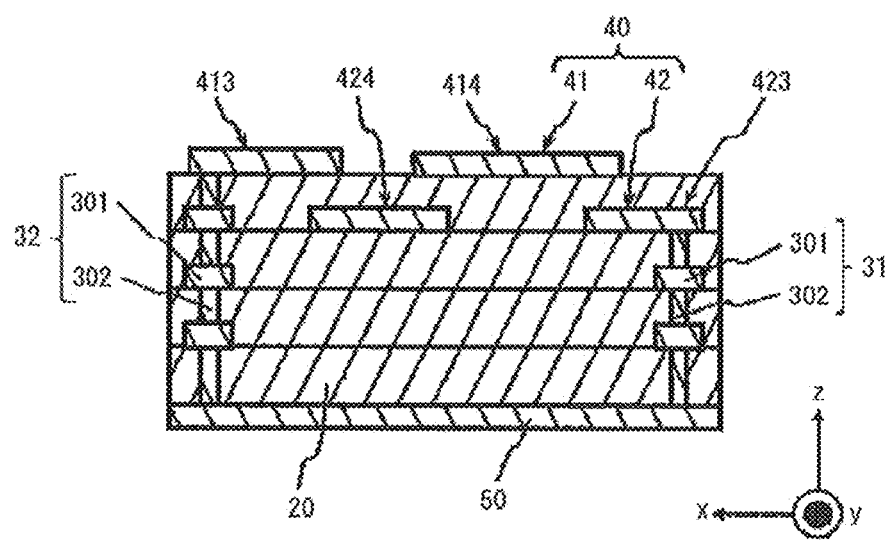
FIG. 36B is a cross-sectional view illustrating an embodiment of a resonator.

The configurations of the resonator 10 in FIGS. 1 to 34A, 34B, 34C, and 34D are illustrated by way of example. The configuration of the resonator 10 is not limited to the configurations illustrated in FIGS. 1 to 34A, 34B, 34C, and 34D. FIG. 35 is a planar view of the xy plane from the z direction. FIG. 36A is a cross-sectional view taken along line XXXVIa-XXXVIa illustrated in FIG. 35. FIG. 36B is a cross-sectional view taken along line XXXVIb-XXXVIb illustrated in FIG. 35.

In the resonator 10 illustrated in FIGS. 35, 36A, and 36B, the first conductive layer 41 includes a half of a patch-type resonator as the first unit resonator 41X. The second conductive layer 42 includes a half of a patch-type resonator as the second unit resonator 42X. The unit resonator 40X includes one first divisional resonator 41Y and one second divisional resonator 42Y. The unit structure 10X includes a unit resonator 40X as well as a part of the base 20 and a part of the fourth conductor 50 that overlap with the unit resonator 40X as viewed in the Z direction. The resonator 10 illustrated in FIG. 35 has three unit resonators 40X arranged in the x direction. The first unit conductor 411 and the second unit conductor 421 included in three unit resonators 40X form one current path 40I.

Figure 37:
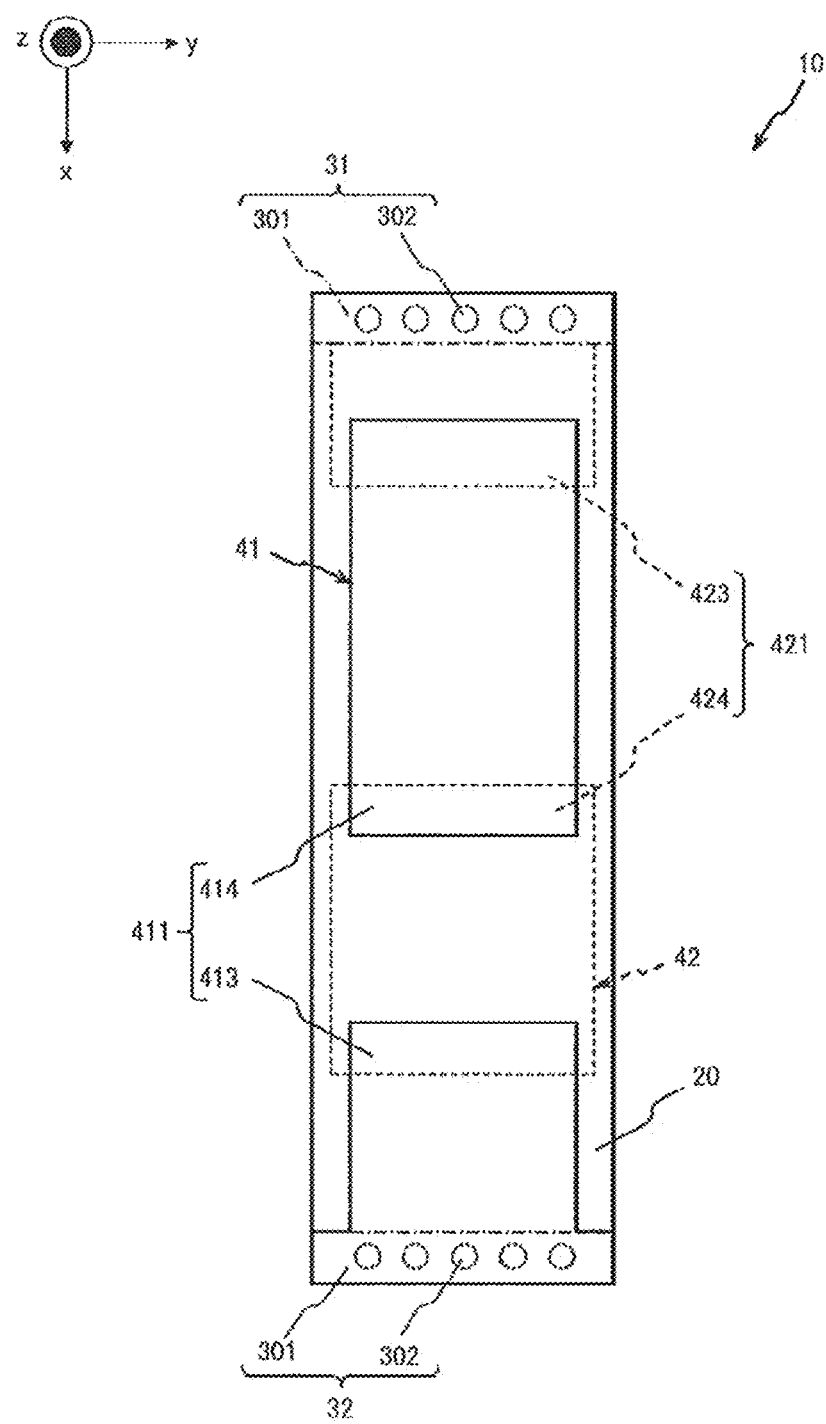
FIG. 37 is a planar view of an embodiment of a resonator.
Figure 38:
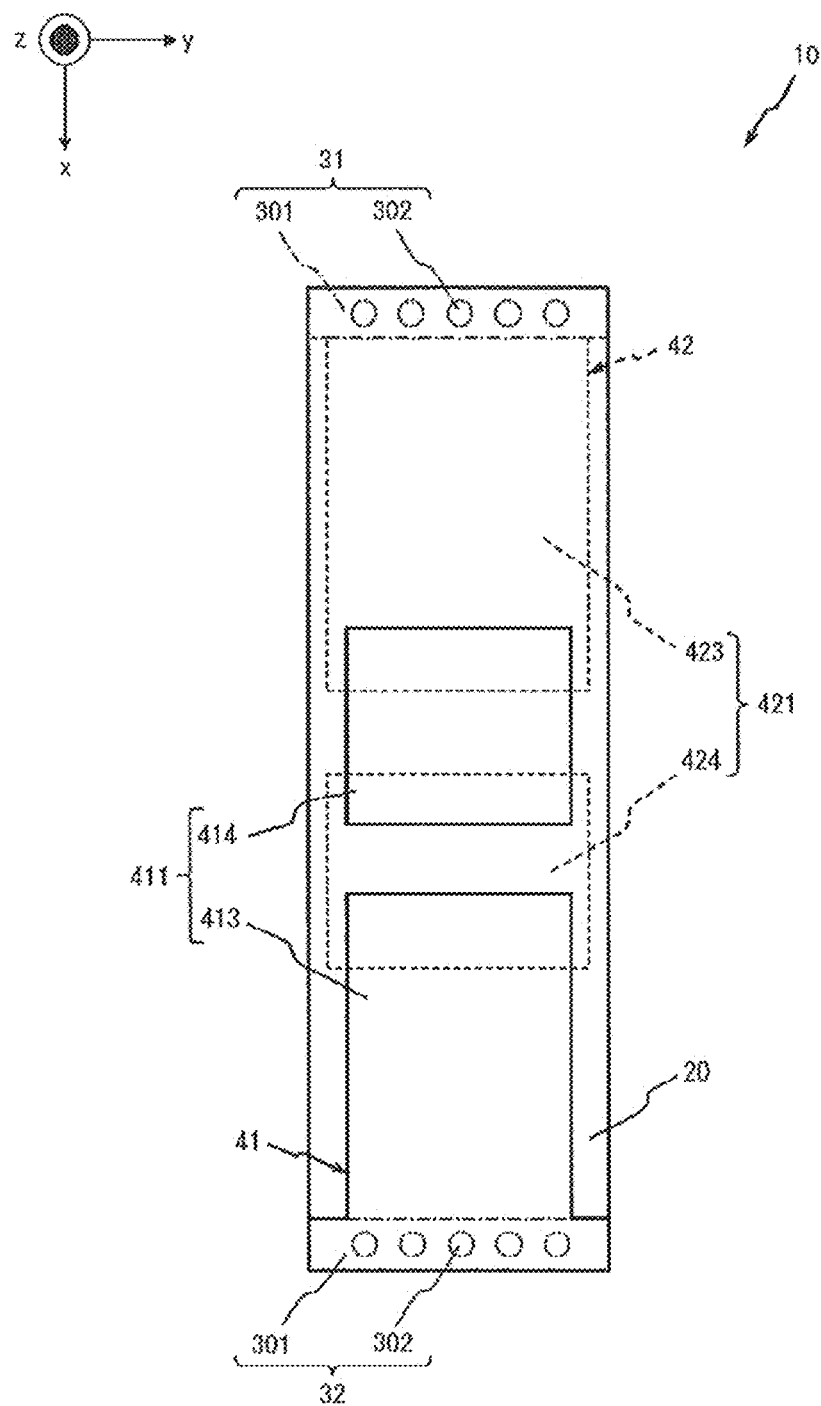
FIG. 38 is a planar view of an embodiment of a resonator.

FIG. 37 illustrates another example of the resonator 10 illustrated in FIG. 35. The resonator 10 illustrated in FIG. 37 is longer in the x direction than the resonator 10 illustrated in FIG. 35. The dimensions of the resonator 10 are not limited to the resonator 10 illustrated in FIG. 37 and may be changed as appropriate. In the resonator 10 in FIG. 37, the first connecting conductor 413 differs from the first floating conductor 414 in length in the x direction. In the resonator 10 in FIG. 37, the length in the x direction of the first connecting conductor 413 is shorter than that of the first floating conductor 414. FIG. 38 illustrates another example of the resonator 10 illustrated in FIG. 35. In the resonator 10 illustrated in FIG. 38, the third conductor 40 differs in length in the x direction. In the resonator 10 in FIG. 38, the length in the x direction of the first connecting conductor 413 is longer than that of the first floating conductor 414.

Figure 39:
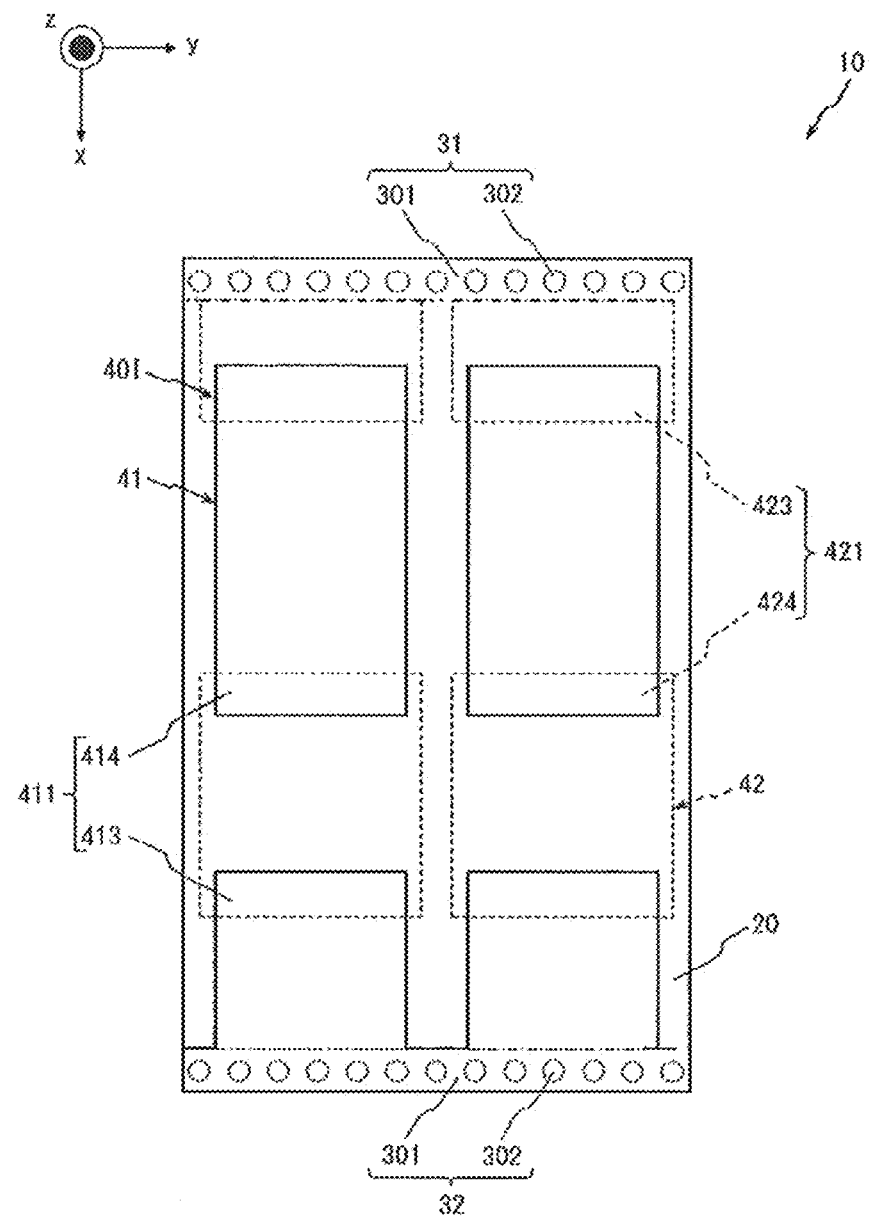
FIG. 39 is a planar view of an embodiment of a resonator.

FIG. 39 illustrates another example of the resonator 10. FIG. 39 illustrates another example of the resonator 10 illustrated in FIG. 37. In a plurality of embodiments, in the resonator 10, a plurality of first unit conductors 411 and second unit conductors 421 arranged in the x direction are capacitively coupled. In the resonator 10, two current paths 40I may be arranged in the y direction, in which current does not flow from one to the other.

Figure 40:
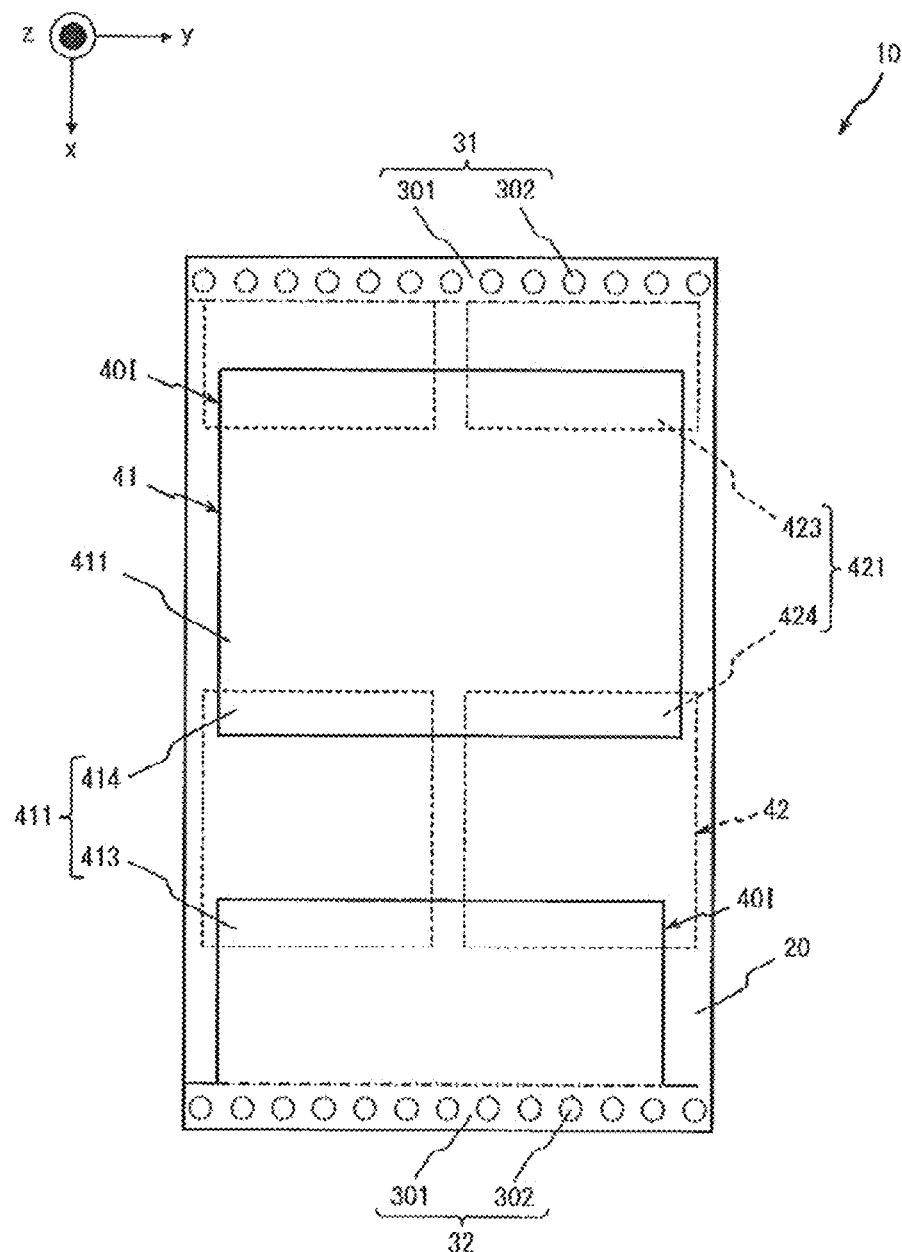
FIG. 40 is a planar view of an embodiment of a resonator.

FIG. 40 illustrates another example of the resonator 10. FIG. 40 illustrates another example of the resonator 10 illustrated in FIG. 39. In a plurality of embodiments, in the resonator 10, the number of conductive bodies connected to the first conductor 31 may differ from the number of conductive bodies connected to the second conductor 32. In the resonator 10 in FIG. 40, one first connecting conductor 413 are capacitively coupled to two second floating conductors 424. In the resonator 10 in FIG. 40, two second connecting conductors 423 are capacitively coupled to one first floating conductor 414. In a plurality of embodiments, the number of first unit conductors 411 may differ from the number of second unit conductors 421 capacitively coupled to the first unit conductors 411.

Figure 41:
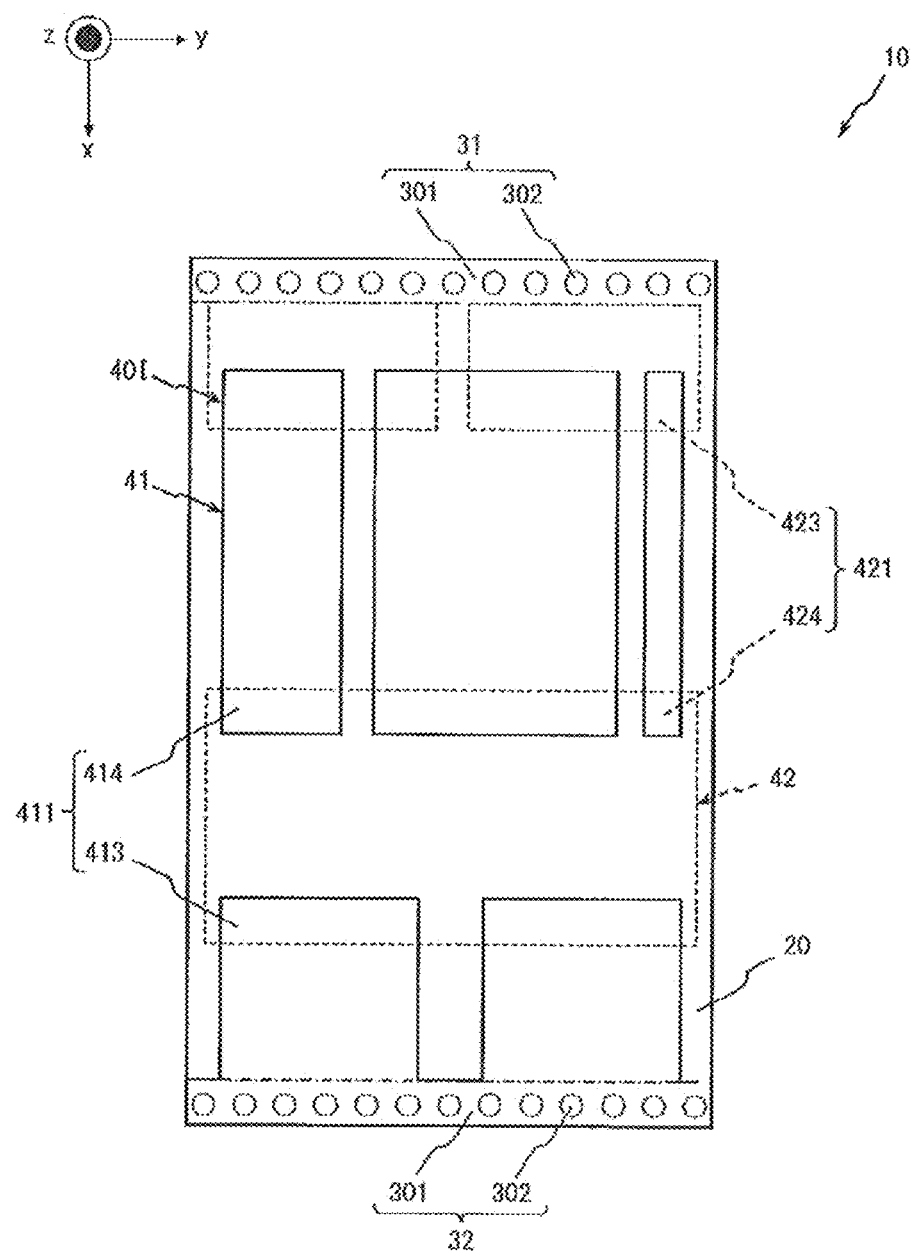
FIG. 41 is a planar view of an embodiment of a resonator.

FIG. 41 illustrates another example of the resonator 10 illustrated in FIG. 39. In a plurality of embodiments, the number of second unit conductors 421 capacitively coupled at a first end portion in the x direction of the first unit conductor 411 may differ from the number of second unit conductors 421 capacitively coupled at a second end portion in the x direction. In the resonator 10 in FIG. 41, two first connecting conductors 413 are capacitively coupled to a first end portion in the x direction of one second floating conductor 424, and three first floating conductors 414 are capacitively coupled to a second end portion thereof. In a plurality of embodiments, a plurality of conductive bodies arranged in the y direction may differ in length in the y direction. In the resonator 10 in FIG. 41, three first floating conductors 414 arranged in the y direction differ in length in the y direction.

Figure 42:
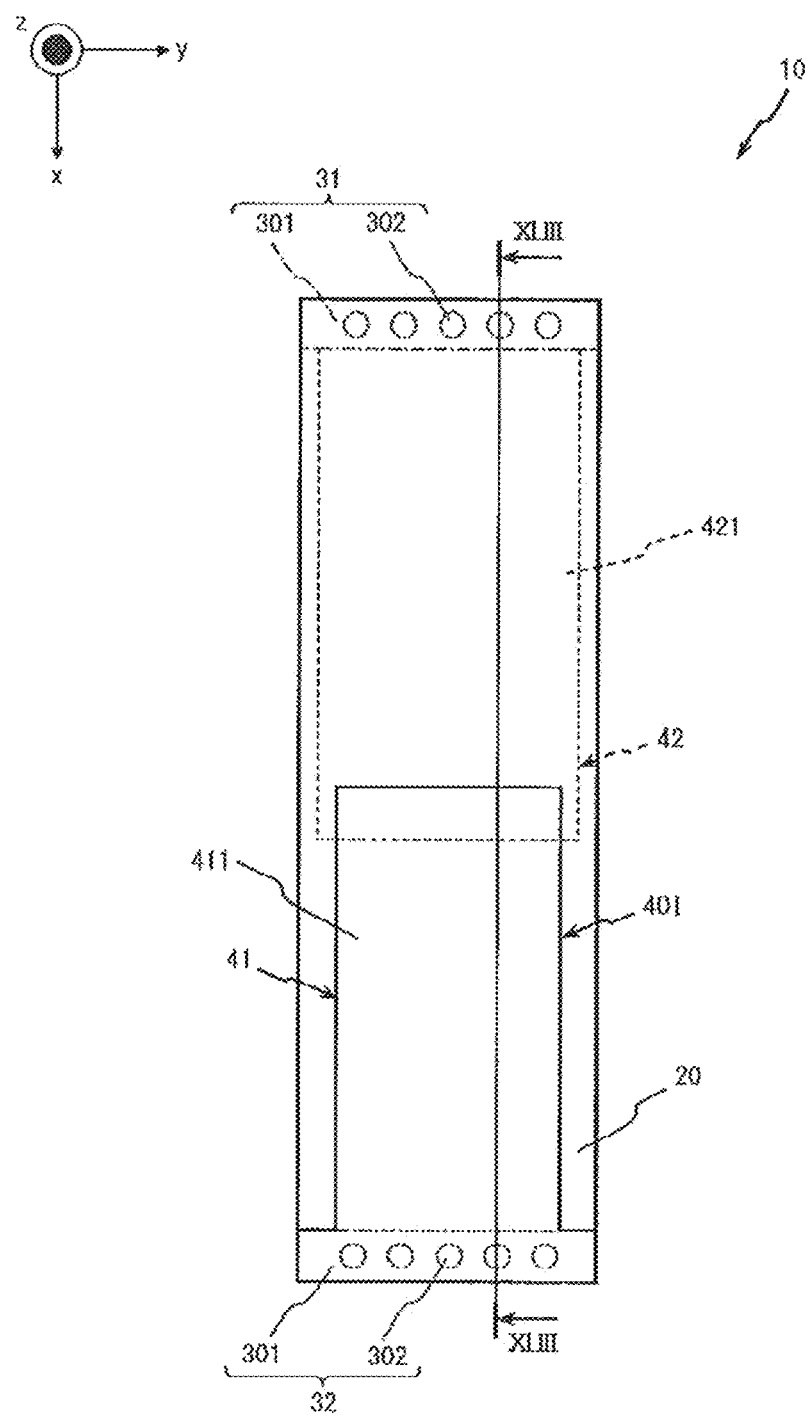
FIG. 42 is a planar view of an embodiment of a resonator.
Figure 43:
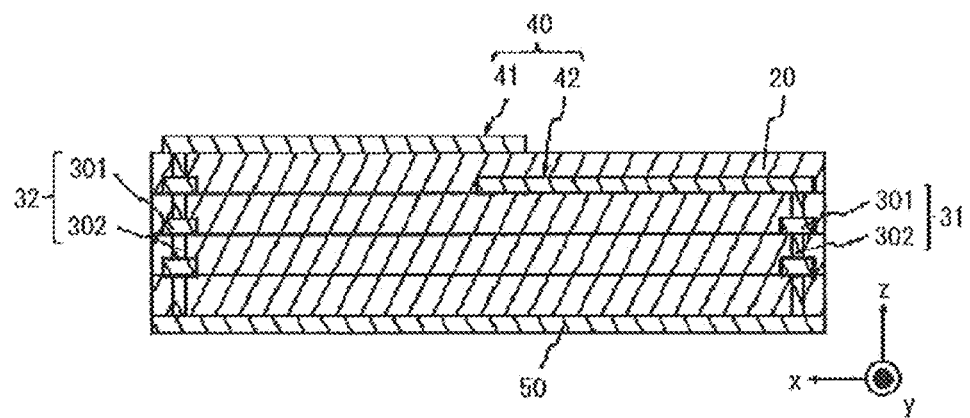
FIG. 43 is a cross-sectional view illustrating an embodiment of a resonator.

FIG. 42 illustrates another example of the resonator 10. FIG. 43 is a cross-sectional view taken along line XLIII-XLIII illustrated in FIG. 42. In the resonator 10 illustrated in FIGS. 42 and 43, the first conductive layer 41 includes a half of a patch-type resonator as a first unit resonator 41X. The second conductive layer 42 includes a half of a patch-type resonator as a second unit resonator 42X. The unit resonator 40X includes one first divisional resonator 41Y and one second divisional resonator 42Y. The unit structure 10X includes a unit resonator 40X as well as a part of the base 20 and a part of the fourth conductor 50 that overlap with the unit resonator 40X as viewed in the z direction. In the resonator 10 illustrated in FIG. 42, one unit resonator 40X extends in the x direction.

Figure 44:
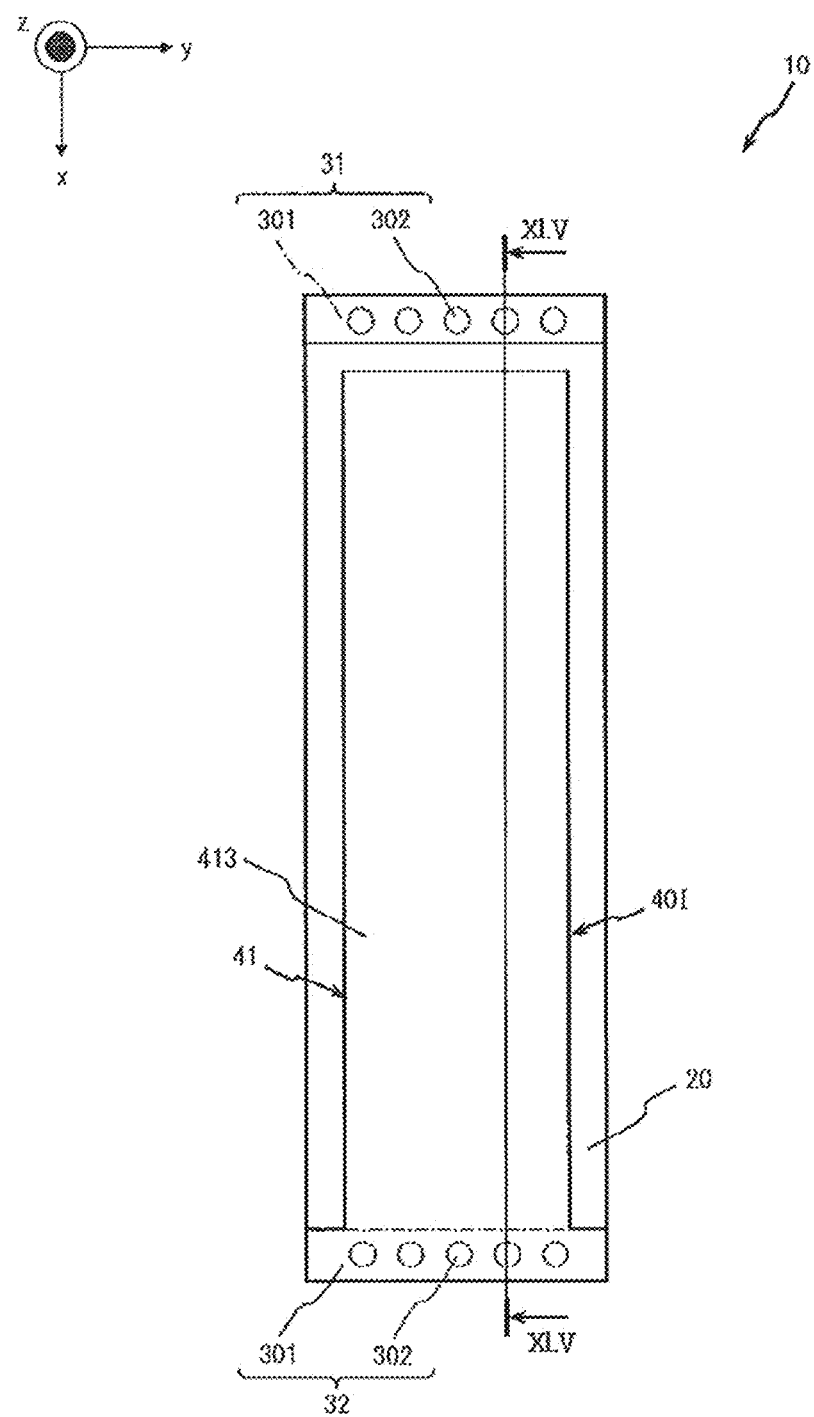
FIG. 44 is a planar view of an embodiment of a resonator.
Figure 45:
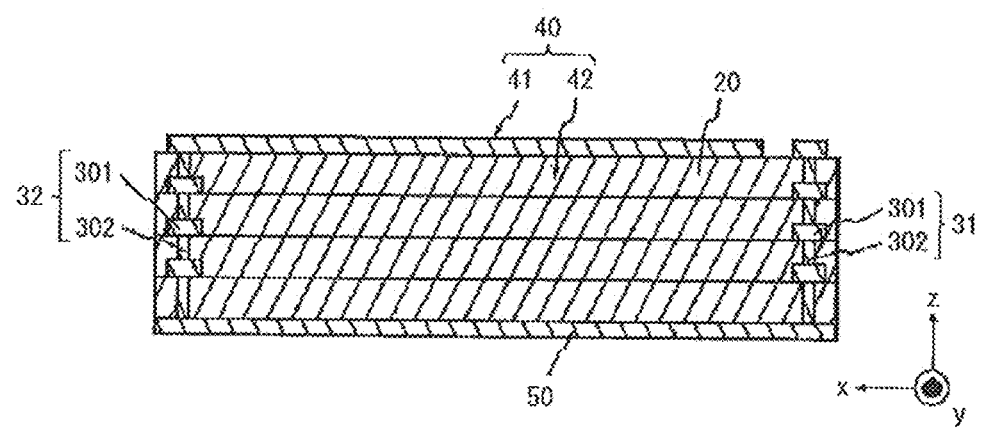
FIG. 45 is a cross-sectional view illustrating an embodiment of a resonator.

FIG. 44 illustrates another example of the resonator 10. FIG. 45 is a cross-sectional view taken along line XLV-XLV illustrated in FIG. 44. In the resonator 10 illustrated in FIGS. 44 and 45, the third conductor 40 includes only the first connecting conductor 413. The first connecting conductor 413 is opposed to the first conductor 31 in the xy plane. The first connecting conductor 413 is capacitively coupled to the first conductor 31.

Figure 46:
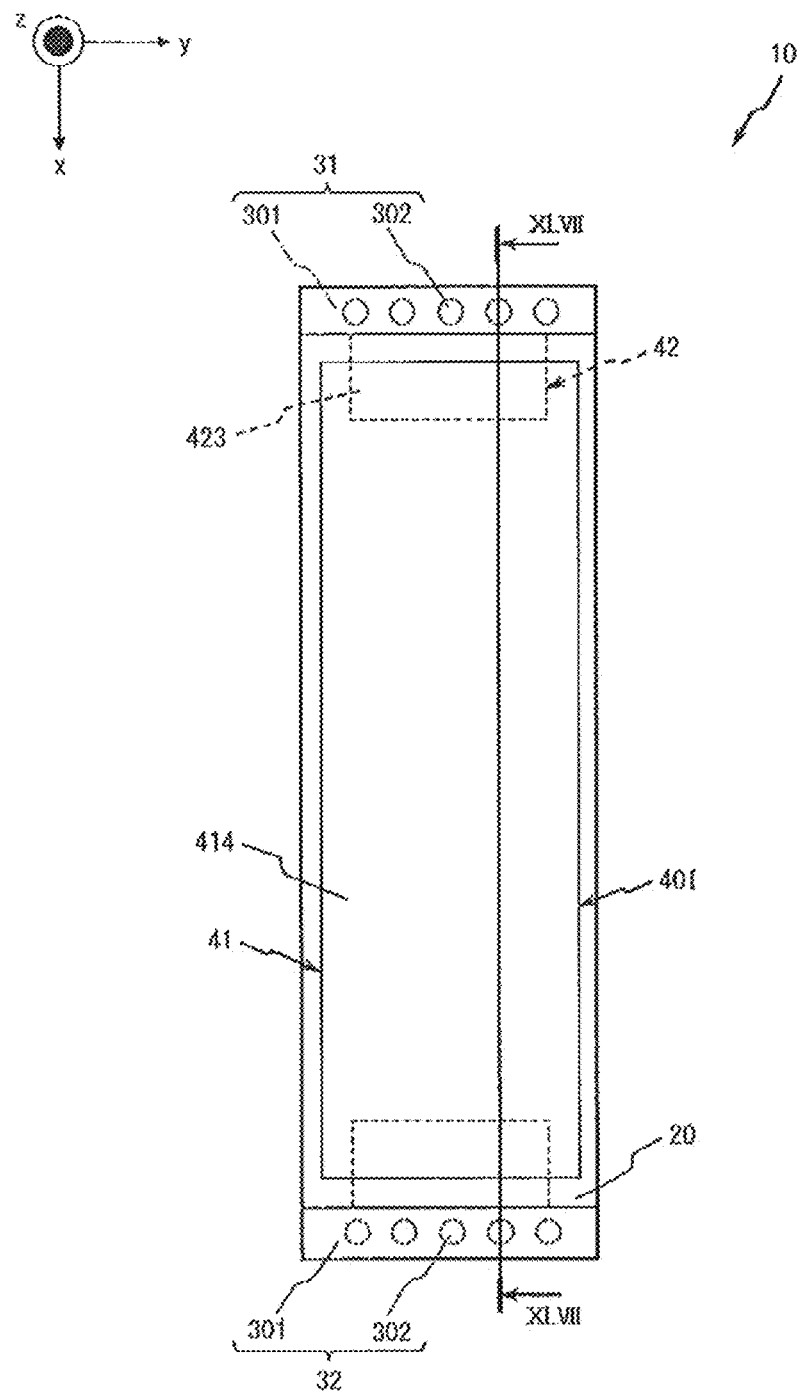
FIG. 46 is a planar view of an embodiment of a resonator.
Figure 47:
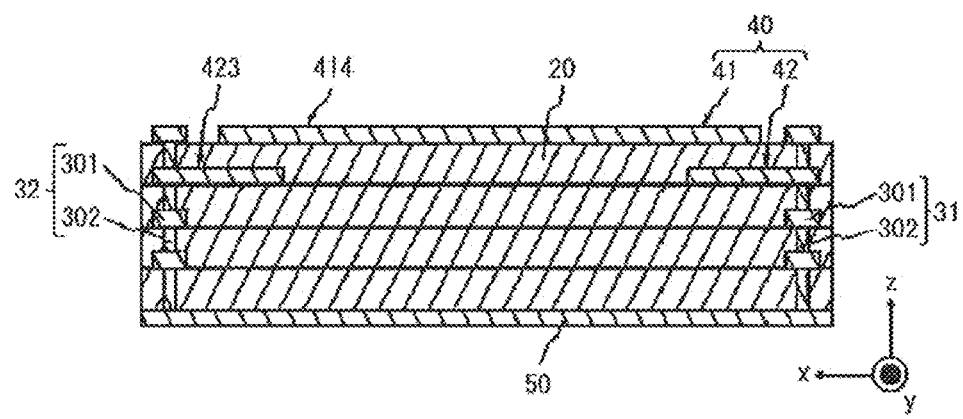
FIG. 47 is a cross-sectional view illustrating an embodiment of a resonator.

FIG. 46 illustrates another example of the resonator 10. FIG. 47 is a cross-sectional view taken along line XLVII-XLVII illustrated in FIG. 46. In the resonator 10 illustrated in FIGS. 46 and 47, the third conductor 40 has a first conductive layer 41 and a second conductive layer 42. The first conductive layer 41 has one first floating conductor 414. The second conductive layer 42 has two second connecting conductors 423. The first conductive layer 41 is opposed to the pair conductors 30 in the xy plane. Two second connecting conductors 423 overlap with one first floating conductor 414 as viewed in the z direction. One first floating conductor 414 is capacitively coupled to two second connecting conductors 423.

Figure 48:
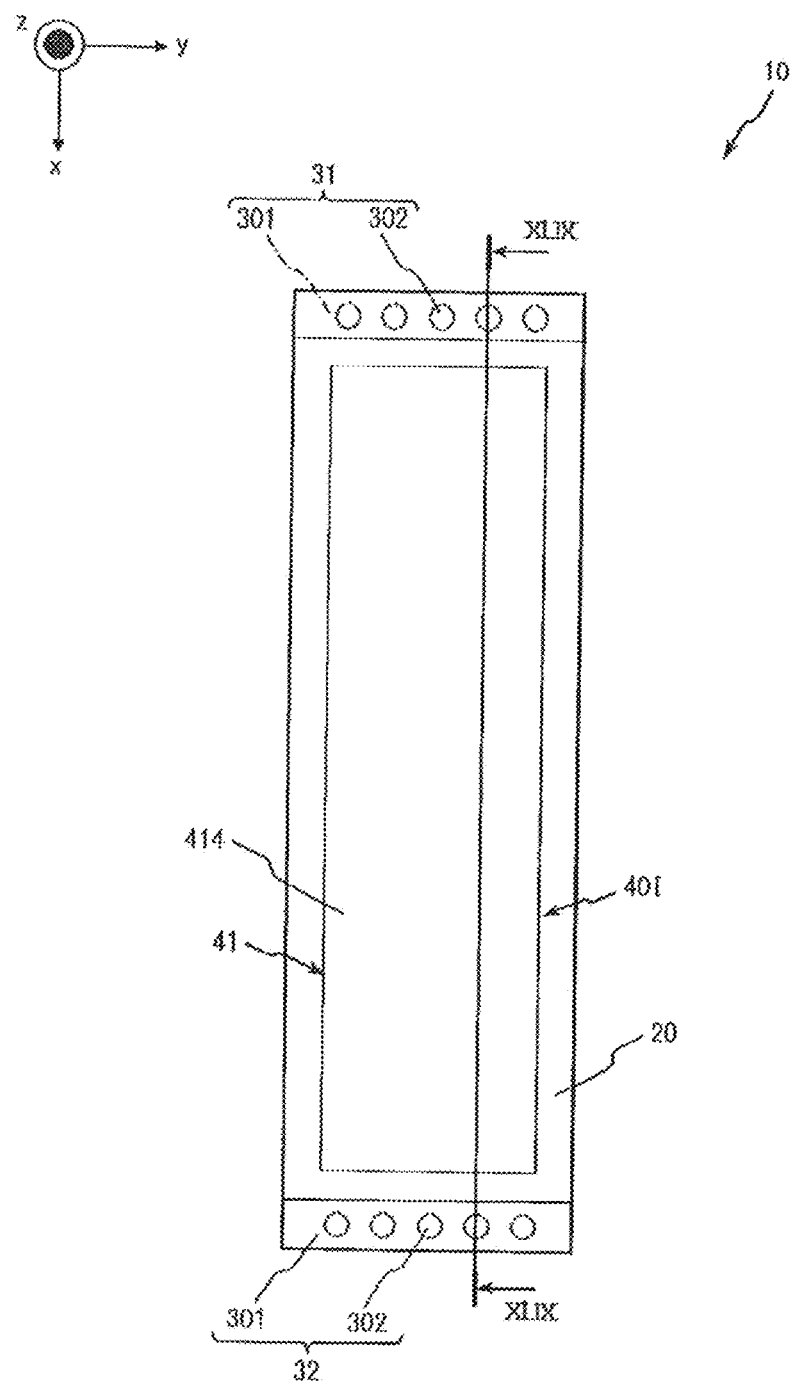
FIG. 48 is a planar view of an embodiment of a resonator.
Figure 49:
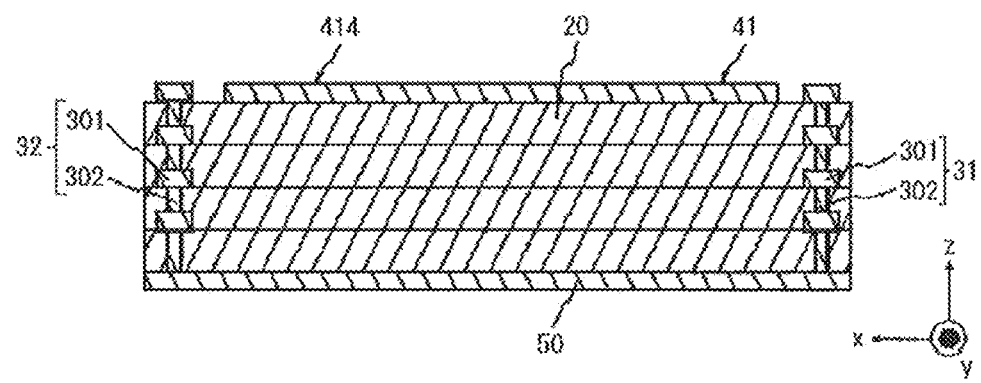
FIG. 49 is a cross-sectional view illustrating an embodiment of a resonator.

FIG. 48 illustrates another example of the resonator 10. FIG. 49 is a cross-sectional view taken along line XLIX-XLIX illustrated in FIG. 48. In the resonator 10 illustrated in FIGS. 48 and 49, the third conductor 40 includes only the first floating conductor 414. The first floating conductor 414 is opposed to the pair conductors 30 in the xy plane. The first connecting conductor 413 is capacitively coupled to the pair conductors 30.

Figure 50:
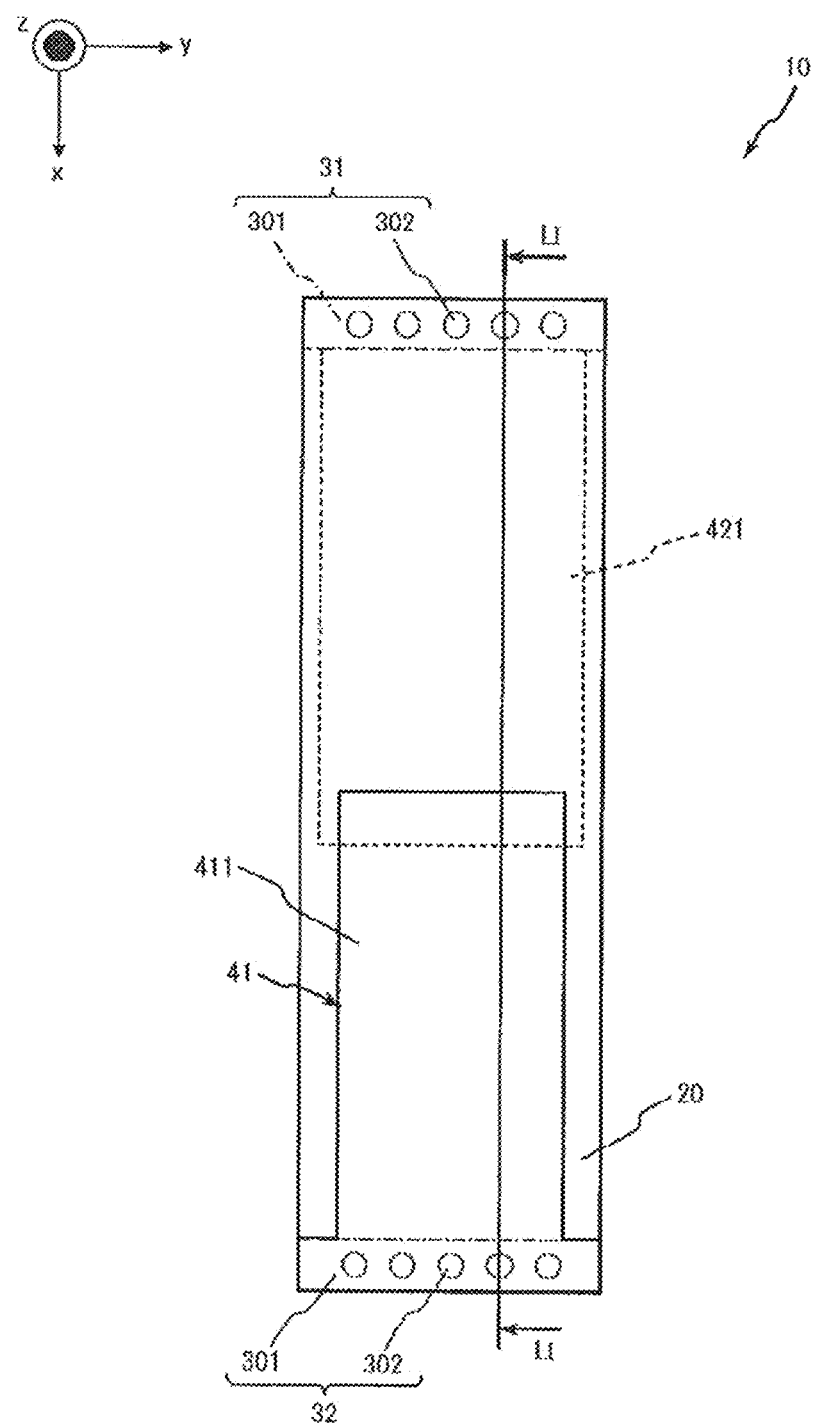
FIG. 50 is a planar view of an embodiment of a resonator.
Figure 51:
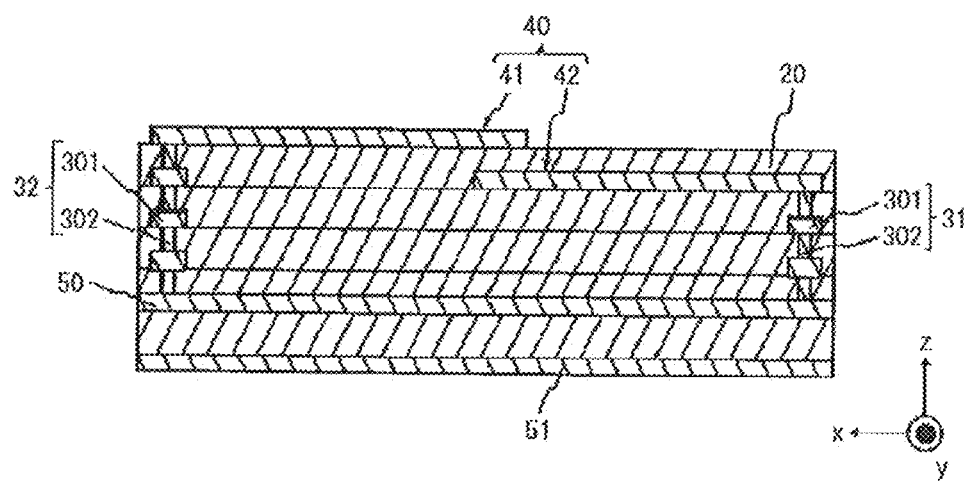
FIG. 51 is a cross-sectional view illustrating an embodiment of a resonator.

FIG. 50 illustrates another example of the resonator 10. FIG. 51 is a cross-sectional view taken along line LI-LI illustrated in FIG. 50. The resonator 10 illustrated in FIGS. 50 and 51 differs from the resonator 10 illustrated in FIGS. 42 and 43 in configuration of the fourth conductor 50. The resonator 10 illustrated in FIGS. 50 and 51 includes a fourth conductor 50 and a reference potential layer 51. The reference potential layer 51 is electrically connected to the ground of a device having the resonator 10. The reference potential layer 51 is opposed to the third conductor 40 with the fourth conductor 50 interposed therebetween. The fourth conductor 50 is positioned between the third conductor 40 and the reference potential layer 51. The spacing between the reference potential layer 51 and the fourth conductor 50 is narrower than the spacing between the third conductor 40 and the fourth conductor 50.

Figure 52:
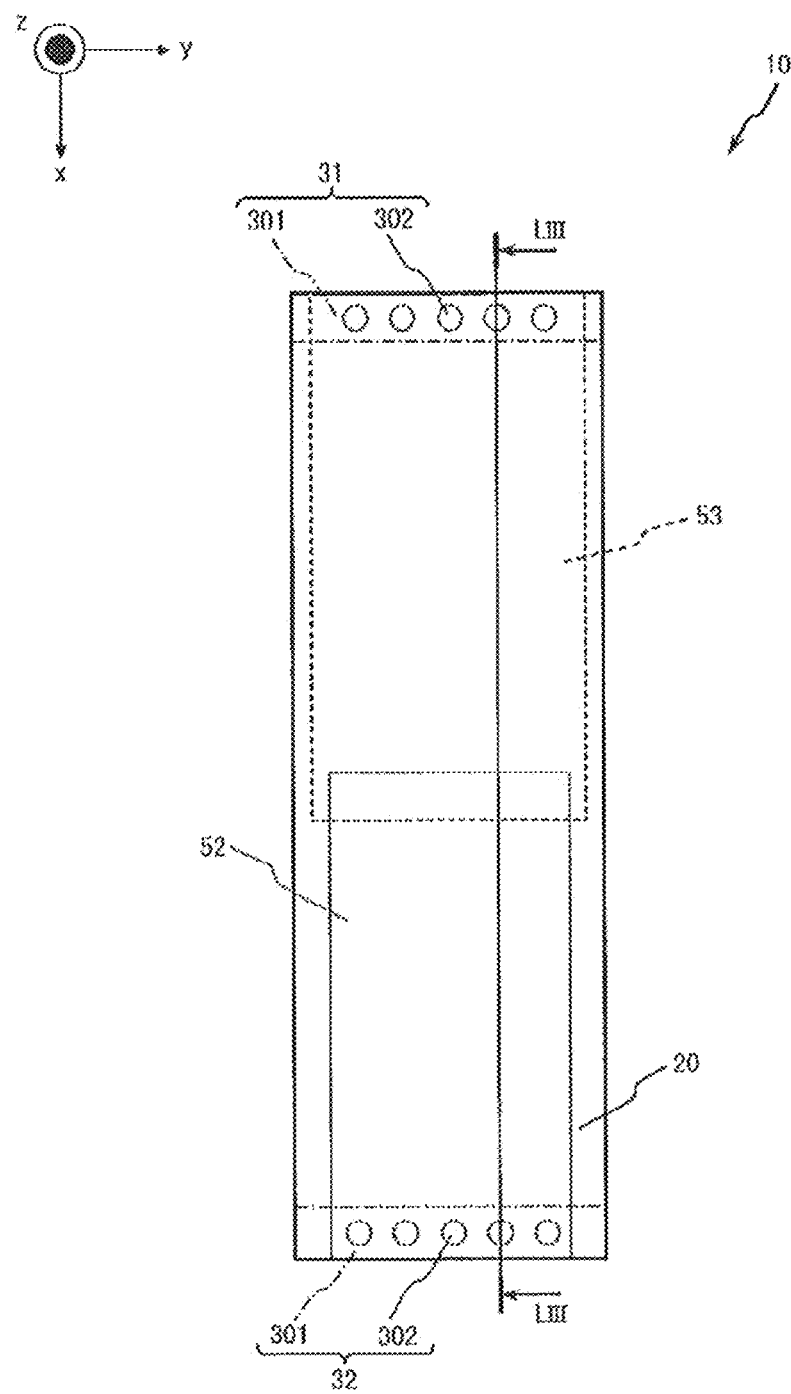
FIG. 52 is a planar view of an embodiment of a resonator.
Figure 53:
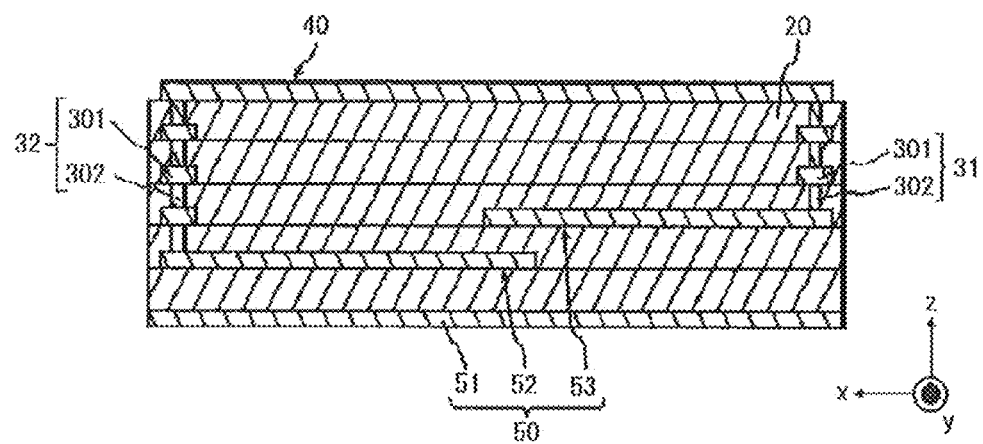
FIG. 53 is a cross-sectional view illustrating an embodiment of a resonator.

FIG. 52 illustrates another example of the resonator 10. FIG. 53 is a cross-sectional view taken along line LIII-LIII illustrated in FIG. 52. The resonator 10 includes a fourth conductor 50 and a reference potential layer 51. The reference potential layer 51 is electrically connected to the ground of a device having the resonator 10. The fourth conductor 50 includes a resonator. The fourth conductor 50 includes a third conductive layer 52 and a fourth conductive layer 53. The third conductive layer 52 and the fourth conductive layer 53 are capacitively coupled. The third conductive layer 52 and the fourth conductive layer 53 are opposed to each other in the z direction. The distance between the third conductive layer 52 and the fourth conductive layer 53 is shorter than the distance between the fourth conductive layer 53 and the reference potential layer 51. The distance between the third conductive layer 52 and the fourth conductive layer 53 is shorter than the distance between the fourth conductor 50 and the reference potential layer 51. The third conductor 40 is one conductive layer.

Figure 54:
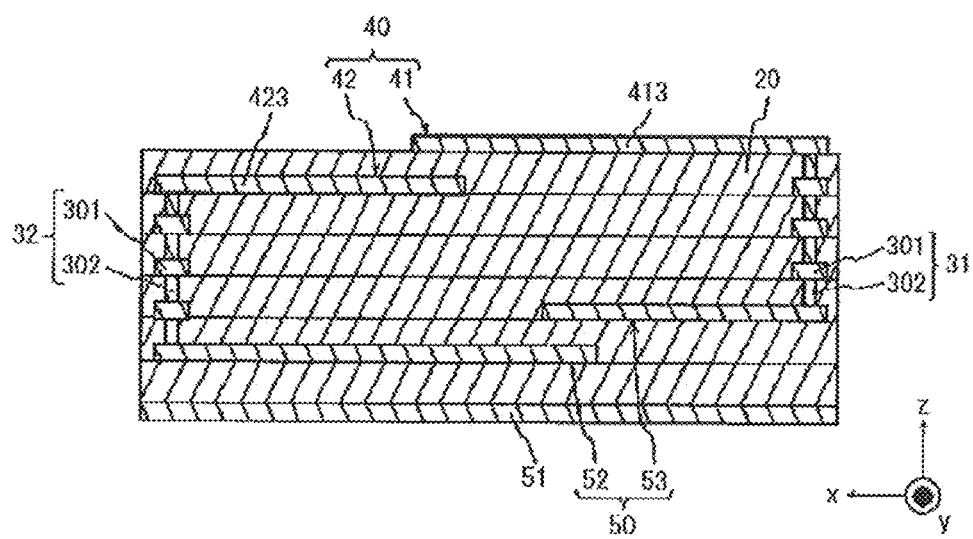
FIG. 54 is a cross-sectional view illustrating an embodiment of a resonator.

FIG. 54 illustrates another example of the resonator 10 illustrated in FIG. 53. The resonator 10 includes a third conductor 40, a fourth conductor 50, and a reference potential layer 51. The third conductor 40 includes a first conductive layer 41 and a second conductive layer 42. The first conductive layer 41 includes a first connecting conductor 413. The second conductive layer 42 includes a second connecting conductor 423. The first connecting conductor 413 is capacitively coupled to the second connecting conductor 423. The reference potential layer 51 is electrically connected to the ground of a device having the resonator 10. The fourth conductor 50 includes a third conductive layer 52 and a fourth conductive layer 53. The third conductive layer 52 and the fourth conductive layer 53 are capacitively coupled. The third conductive layer 52 and the fourth conductive layer 53 are opposed to each other in the z direction. The distance between the third conductive layer 52 and the fourth conductive layer 53 is shorter than the distance between the fourth conductive layer 53 and the reference potential layer 51. The distance between the third conductive layer 52 and the fourth conductive layer 53 is shorter than the distance between the fourth conductor 50 and the reference potential layer 51.

Figure 55:
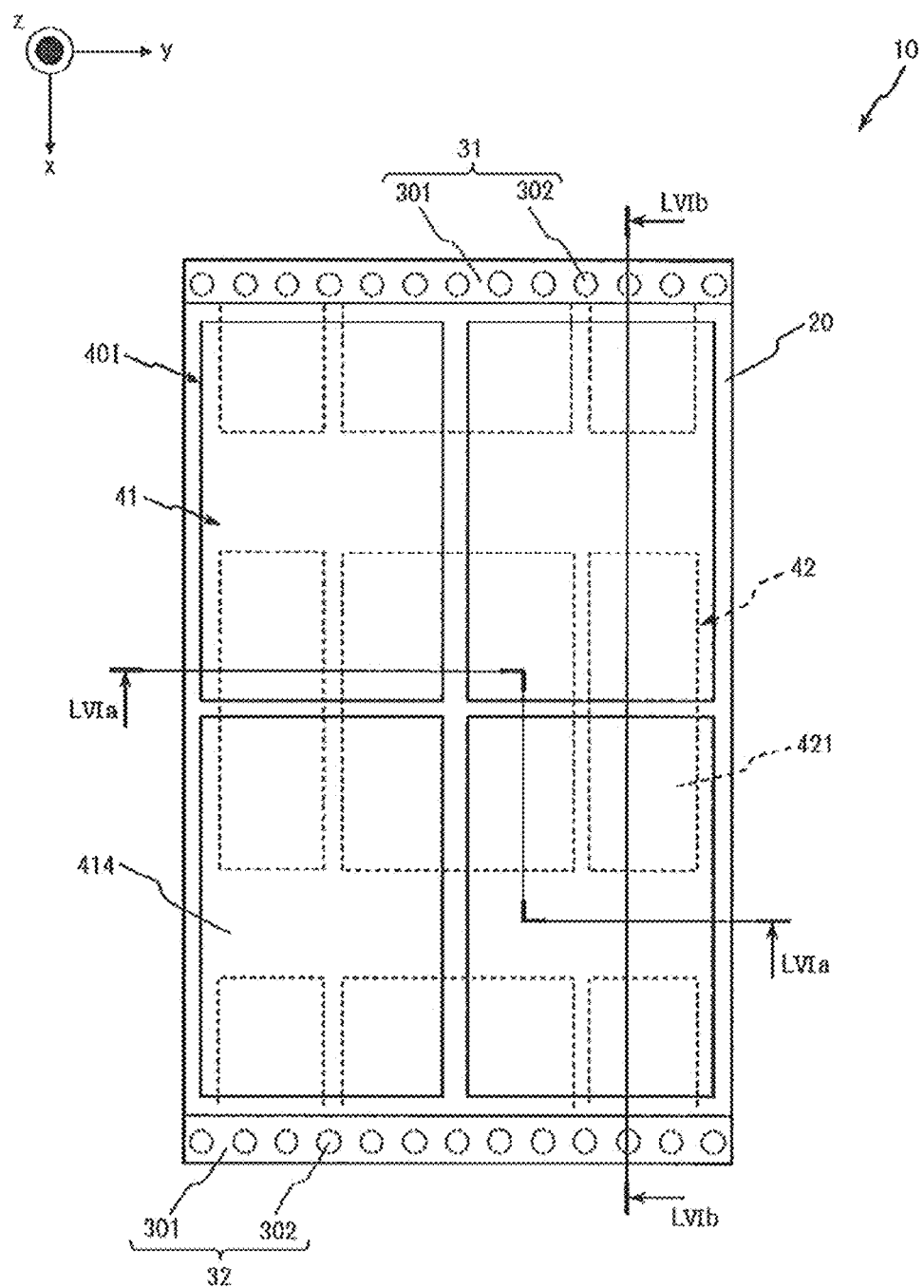
FIG. 55 is a planar view of an embodiment of a resonator.
Figure 56A:
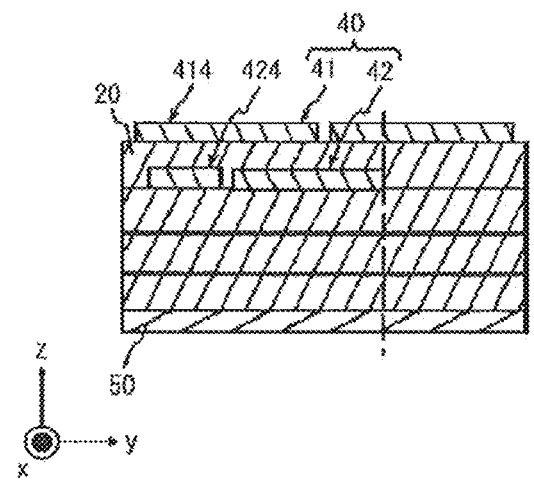
FIG. 56A is a cross-sectional view illustrating an embodiment of a resonator.
Figure 56B:
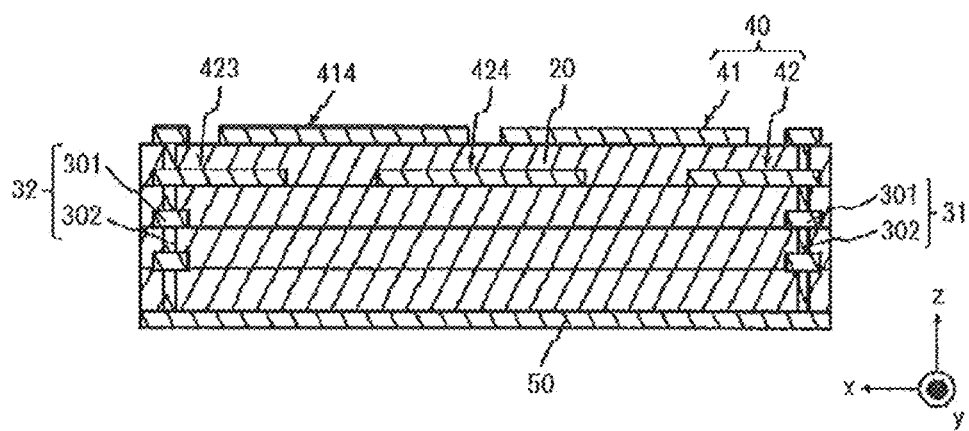
FIG. 56B is a cross-sectional view illustrating an embodiment of a resonator.

FIG. 55 illustrates another example of the resonator 10. FIG. 56A is a cross-sectional view taken along line LVIa-LVIa illustrated in FIG. 55. FIG. 56B is a cross-sectional view taken along line LVIb-LVIb illustrated in FIG. 55. In the resonator 10 illustrated in FIG. 55, the first conductive layer 41 has four first floating conductors 414. The first conductive layer 41 illustrated in FIG. 55 does not have a first connecting conductor 413. In the resonator 10 illustrated in FIG. 55, the second conductive layer 42 has six second connecting conductors 423 and three second floating conductors 424. Each of two second connecting conductors 423 is capacitively coupled to two first floating conductors 414. One second floating conductor 424 is capacitively coupled to four first floating conductors 414. Two second floating conductors 424 are capacitively coupled to two first floating conductors 414.

Figure 57:
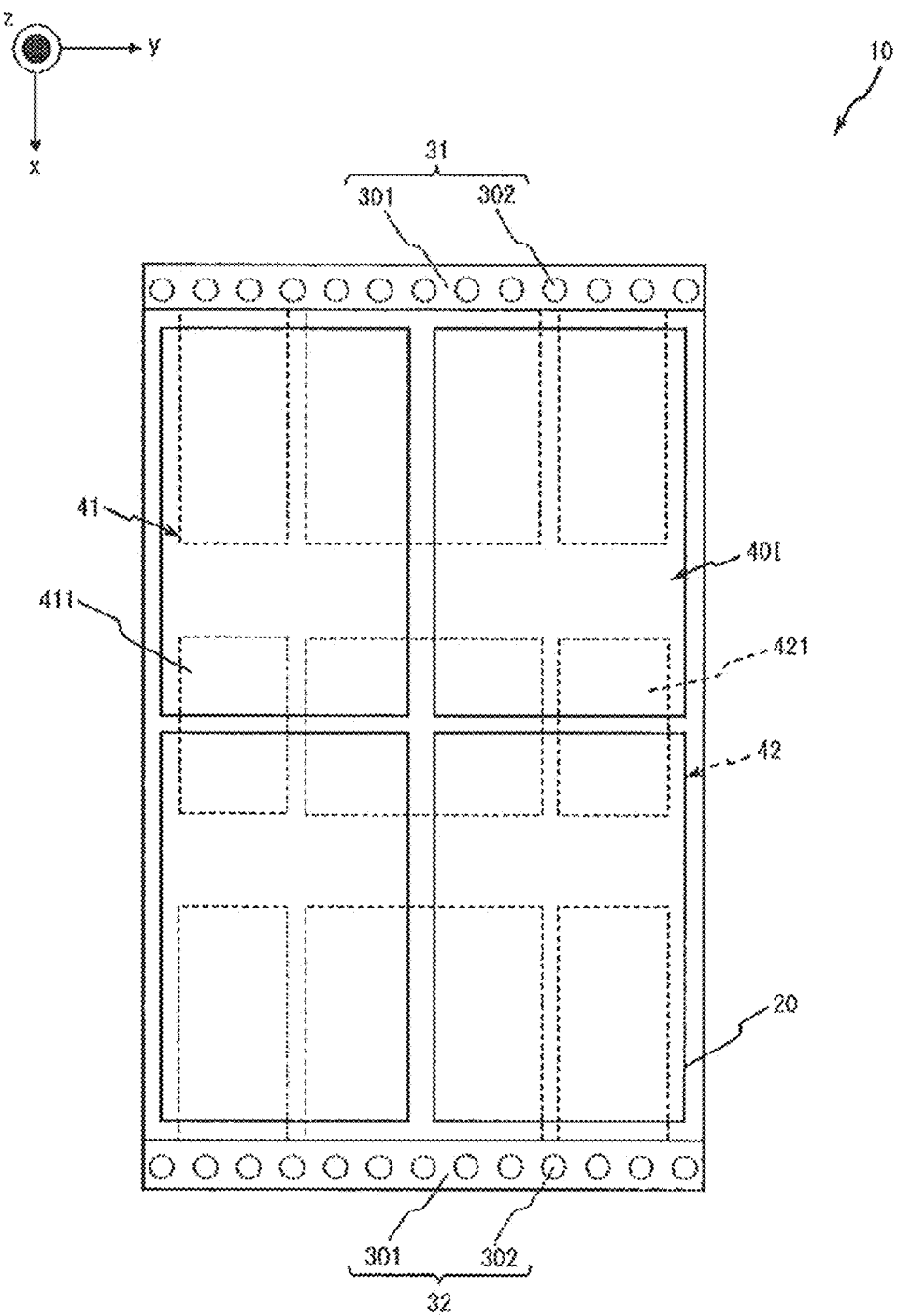
FIG. 57 is a planar view of an embodiment of a resonator.

FIG. 57 illustrates another example of the resonator illustrated in FIG. 55. The resonator 10 in FIG. 57 differs from the resonator 10 illustrated in FIG. 55 in size of the second conductive layer 42. In the resonator 10 illustrated in FIG. 57, the length along the x direction of the second floating conductor 424 is shorter than the length along the x direction of the second connecting conductor 423.

Figure 58:
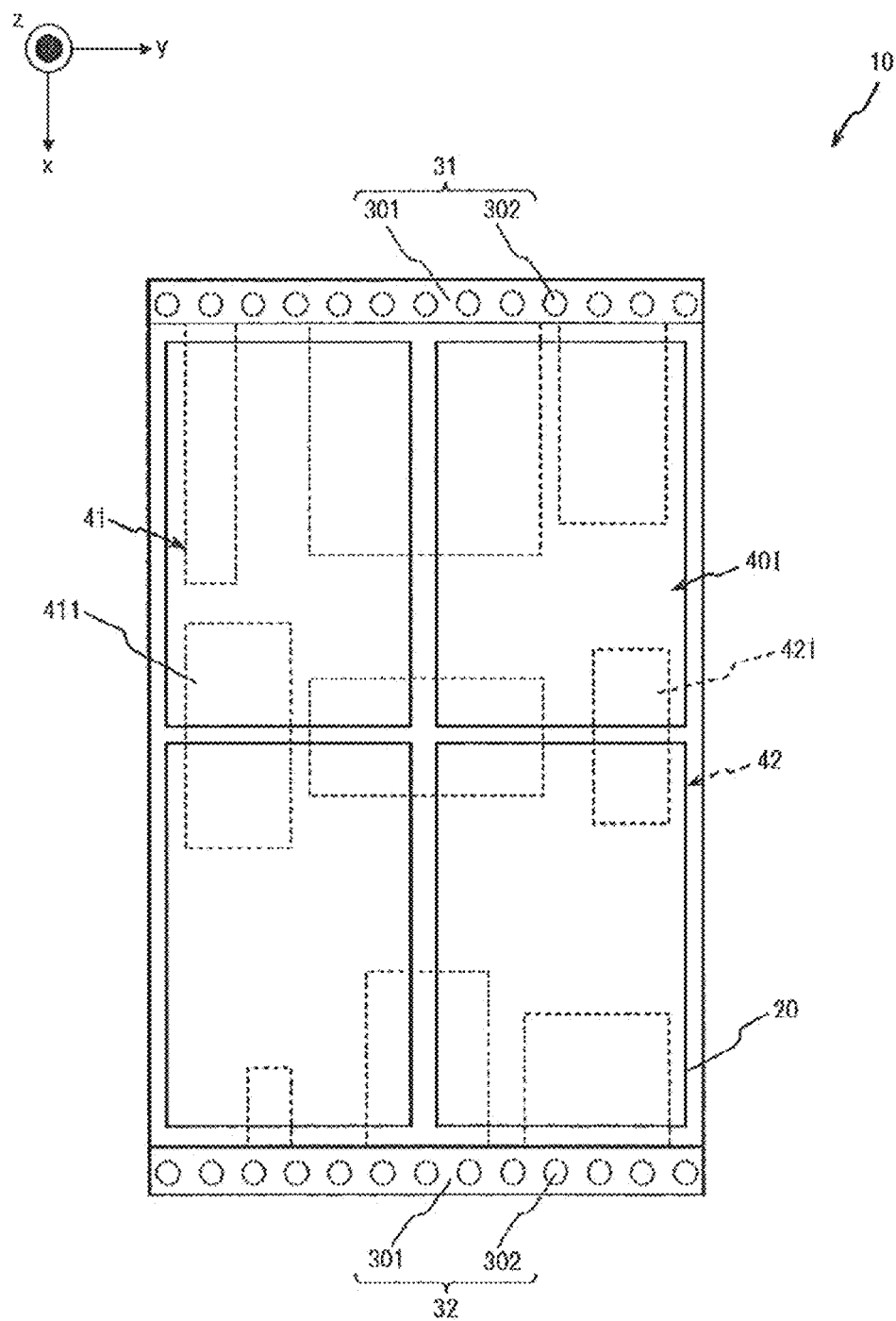
FIG. 58 is a planar view of an embodiment of a resonator.

FIG. 58 illustrates another example of the resonator illustrated in FIG. 55. The resonator 10 in FIG. 58 differs from the resonator 10 illustrated in FIG. 55 in size of the second conductive layer 42. In the resonator 10 illustrated in FIG. 58, a plurality of second unit conductors 421 differ in first surface integral. In the resonator 10 illustrated in FIG. 58, a plurality of second unit conductors 421 differ in length in the x direction. In the resonator 10 illustrated in FIG. 58, a plurality of second unit conductors 421 differ in length in the y direction. In FIG. 58, a plurality of second unit conductors 421 differ from each other in first surface integral, length, and width, but the embodiments are not limited thereto. In FIG. 58, a plurality of second unit conductors 421 may differ from each other in part of first surface integral, length, and width. A plurality of second unit conductor 421 may be equal to each other in some or all of first surface integral, length, and width. A plurality of second unit conductor 421 may differ from each other in some or all of first surface integral, length, and width. A plurality of second unit conductors 421 may be equal to each other in some or all of first surface integral, length, and width. Some of a plurality of second unit conductors 421 may be equal to each other in some or all of first surface integral, length, and width.

In the resonator 10 illustrated in FIG. 58, a plurality of second connecting conductors 423 arranged in the y direction differ from each other in first surface integral. In the resonator 10 illustrated in FIG. 58, a plurality of second connecting conductors 423 arranged in the y direction differ from each other in length in the x direction. In the resonator 10 illustrated in FIG. 58, a plurality of second connecting conductors 423 arranged in the y direction differ from each other in length in the y direction. In FIG. 58, a plurality of second connecting conductors 423 differ from each other in first surface integral, length, and width, but the embodiments are not limited thereto. In FIG. 58, a plurality of second connecting conductors 423 may differ from each other partially in first surface integral, length, and width. A plurality of second connecting conductors 423 may be equal to each other in some or all of first surface integral, length, and width. A plurality of second connecting conductors 423 may differ from each other in some or all of first surface integral, length, and width. A plurality of second connecting conductors 423 may be equal to each other in some or all of first surface integral, length, and width. Some of a plurality of second connecting conductors 423 may be equal to each other in some or all of first surface integral, length, and width.

In the resonator 10 illustrated in FIG. 58, a plurality of second floating conductors 424 arranged in the y direction differ from each other in first surface integral. In the resonator 10 illustrated in FIG. 58, a plurality of second floating conductors 424 arranged in the y direction differ from each other in length in the x direction. In the resonator 10 illustrated in FIG. 58, a plurality of second floating conductors 424 arranged in the y direction differ from each other in length in the y direction. In FIG. 58, a plurality of second floating conductors 424 differ from each other in first surface integral, length, and width, but the embodiments are not limited thereto. In FIG. 58, a plurality of second floating conductors 424 may differ from each other partially in first surface integral, length, and width. A plurality of second floating conductors 424 may be equal to each other in some or all of first surface integral, length, and width. A plurality of second floating conductors 424 may differ from each other in some or all of first surface integral, length, and width. A plurality of second floating conductors 424 may be equal to each other in some or all of first surface integral, length, and width. Some of a plurality of second floating conductors 424 may be equal to each other in some or all of first surface integral, length, and width.

Figure 59:
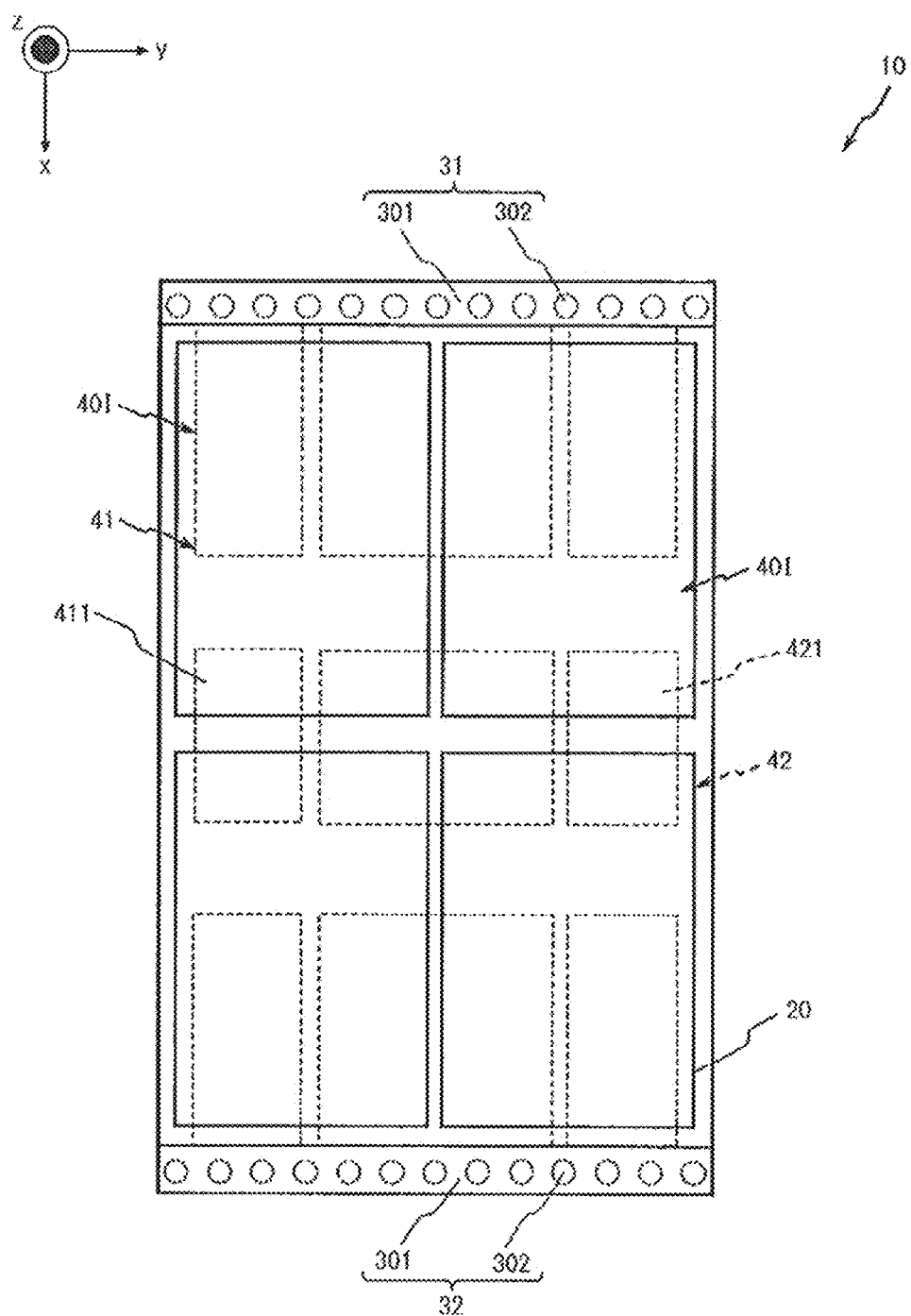
FIG. 59 is a planar view of an embodiment of a resonator.

FIG. 59 illustrates another example of the resonator 10 illustrated in FIG. 57. In the resonator 10 in FIG. 59, the spacing between the first unit conductors 411 in the y direction differs from that of the resonator 10 illustrated in FIG. 57. In the resonator 10 in FIG. 59, the spacing between the first unit conductors 411 in the y direction is smaller than the spacing between the first unit conductors 411 in the x direction. In the resonator 10, current flows in the x direction since the pair conductors 30 can function as electric conductors. In this resonator 10, current flowing through the third conductor 40 in the y direction can be ignored. The spacing between the first unit conductors 411 in the y direction may be shorter than the spacing between the first unit conductors 411 in the x direction. Shortening the spacing between the first unit conductors 411 in the y direction can increase the surface integral of the first unit conductors 411.

Figure 60:
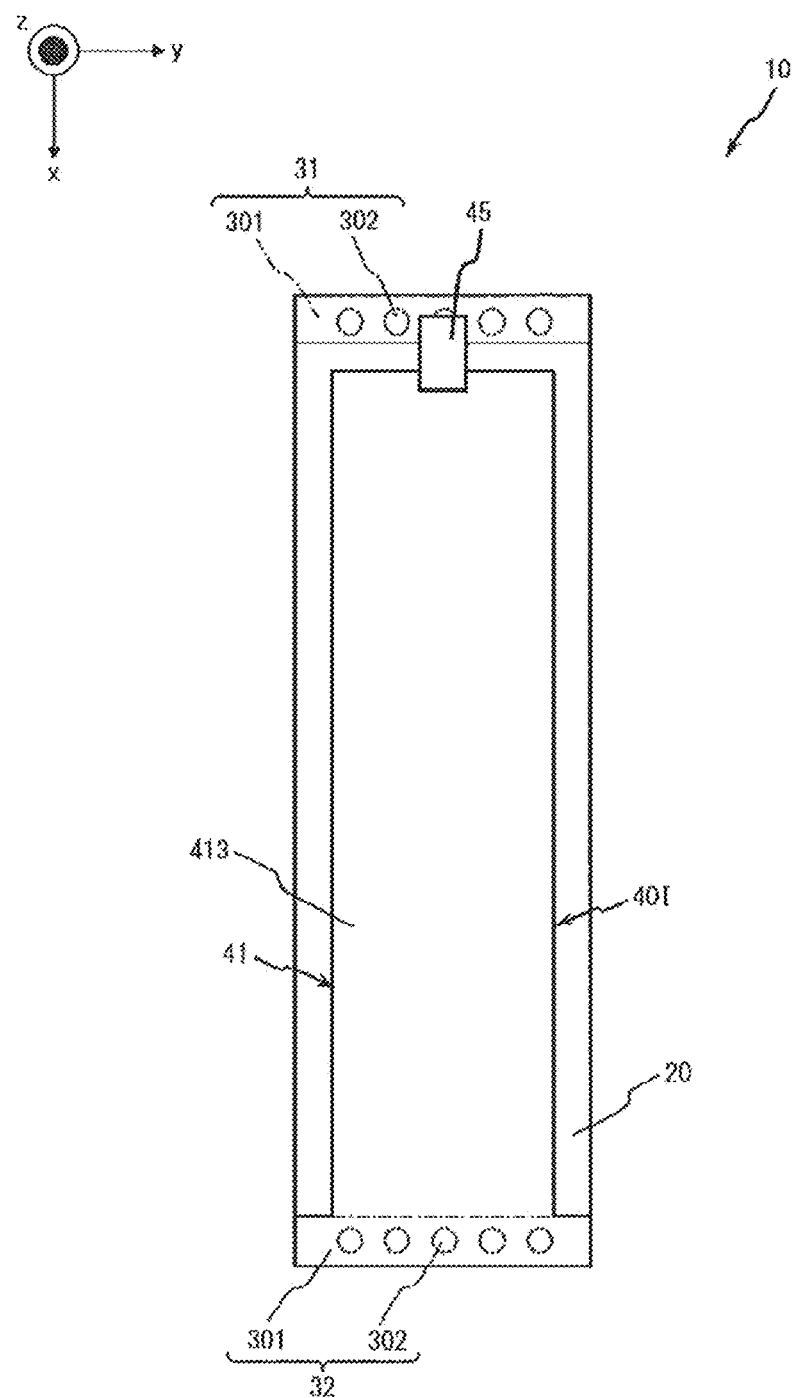
FIG. 60 is a planar view of an embodiment of a resonator.
Figure 61:
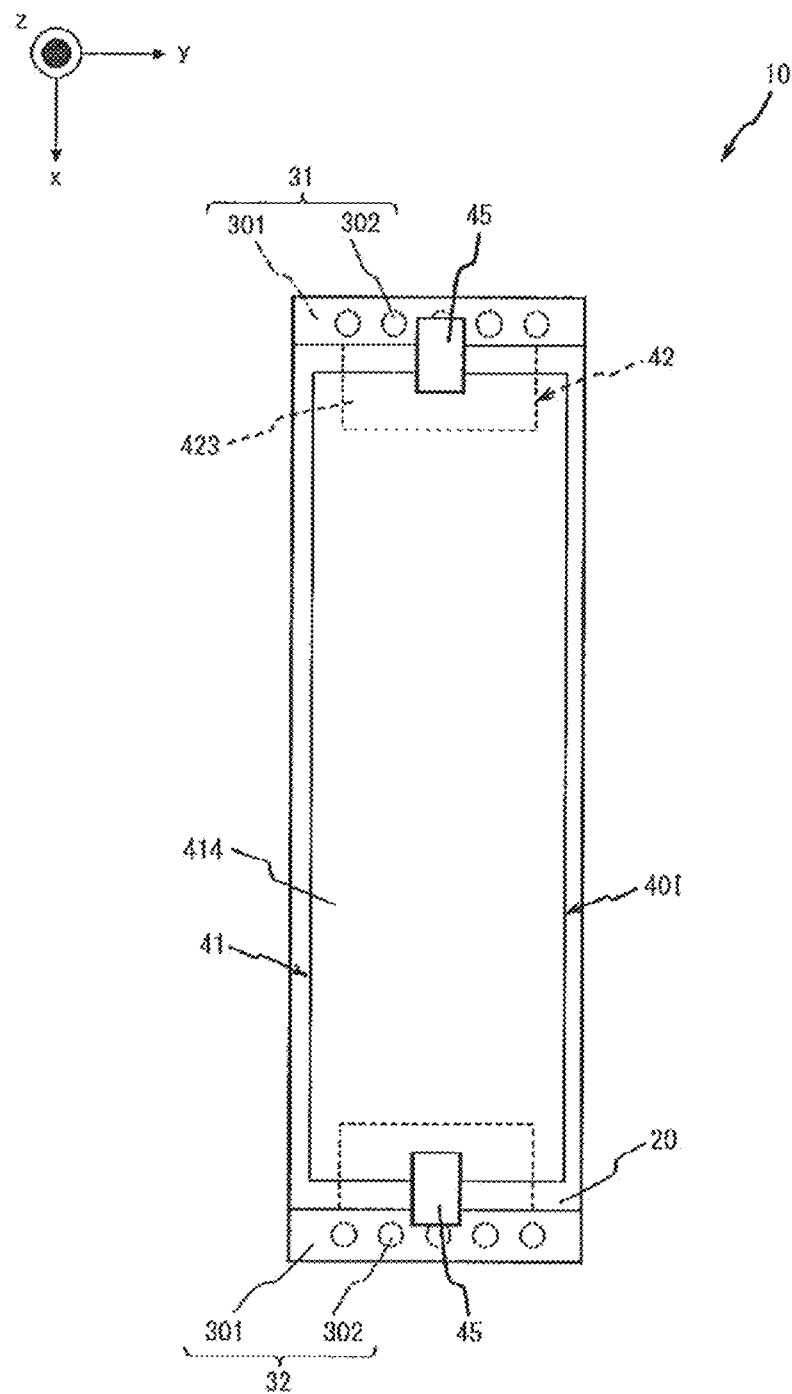
FIG. 61 is a planar view of an embodiment of a resonator.
Figure 62:
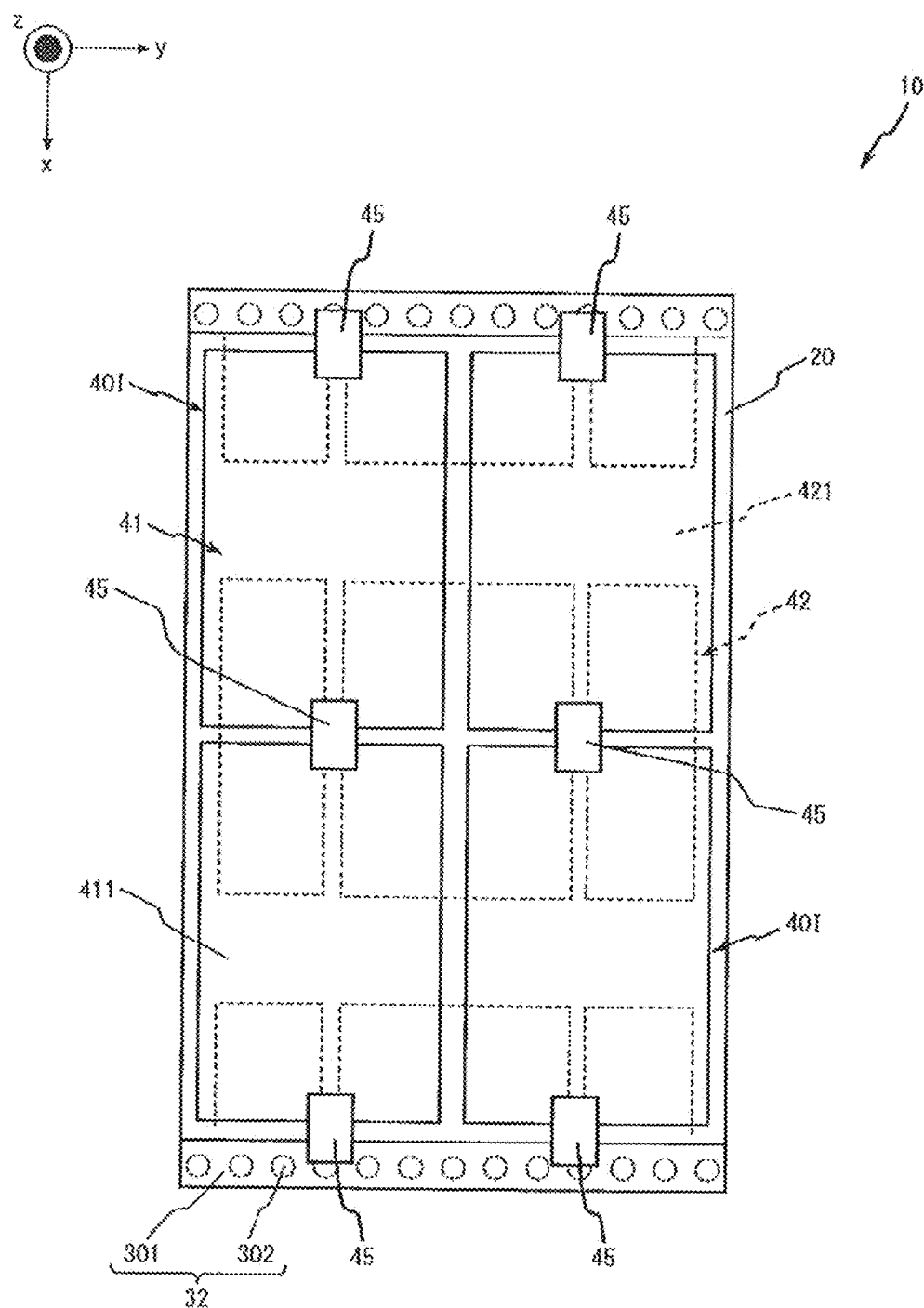
FIG. 62 is a planar view of an embodiment of a resonator.

FIGS. 60 to 62 are diagrams illustrating other examples of the resonator 10. These resonators 10 have an impedance element 45. A unit conductor connected to the impedance element 45 is not limited to the example illustrated in FIGS. 60 to 62. The impedance elements 45 illustrated in FIGS. 60 to 62 can be partially omitted. The impedance element 45 may have a capacitance character. The impedance element 45 may have an inductance character. The impedance element 45 may be a mechanical or electrical variable element. The impedance element 45 may connect two different conductors in one layer.

An antenna has at least one of a function of emitting electromagnetic waves and a function of receiving electromagnetic waves. The antenna in the present disclosure includes a first antenna 60 and a second antenna 70, but the embodiments are not limited thereto.

The first antenna 60 includes a base 20, pair conductors 30, a third conductor 40, a fourth conductor 50, and a first feeding line 61. In an example, the first antenna 60 has a third base 24 on the base 20. The third base 24 may have a composition different from the base 20. The third base 24 may be positioned on the third conductor 40. FIGS. 63 to 76 are diagrams illustrating the first antenna 60 that is an example of a plurality of embodiments.

The first feeding line 61 feeds power to at least one of resonators arranged periodically as artificial magnetic conductors. When power is fed to a plurality of resonators, the first antenna 60 may have a plurality of first feeding lines. The first feeding line 61 may be electromagnetically connected to any one of the resonators arranged periodically as artificial magnetic conductors. The first feeding line 61 may be electromagnetically connected to any one of a pair of conductors viewed as electric conductors from the resonators arranged periodically as artificial magnetic conductors.

The first feeding line 61 feeds power to at least one of the first conductor 31, the second conductor 32, and the third conductor 40. When power is fed to a plurality of portions of the first conductor 31, the second conductor 32, and the third conductor 40, the first antenna 60 may have a plurality of first feeding lines. The first feeding line 61 may be electromagnetically connected to any of the first conductor 31, the second conductor 32, and the third conductor 40. When the first antenna 60 includes a reference potential layer 51 in addition to the fourth conductor 50, the first feeding line 61 may be electromagnetically connected to any one of the first conductor 31, the second conductor 32, the third conductor 40, and the fourth conductor 50. The first feeding line 61 is electrically connected to one of the fifth conductive layer 301 and the fifth conductor 302 of the pair conductor 30. A part of the first feeding line 61 may be integrated with the fifth conductive layer 301.

The first feeding line 61 may be electromagnetically connected to the third conductor 40. For example, the first feeding line 61 is electromagnetically connected to one of the first unit resonators 41X. For example, the first feeding line 61 is electromagnetically connected to one of the second unit resonators 42X. The first feeding line 61 is electromagnetically connected to a unit conductor of the third conductor 40 at a point different from the center in the x direction. In an embodiment, the first feeding line 61 supplies power to at least one resonator included in the third conductor 40. In an embodiment, the first feeding line 61 feeds power from at least one resonator included in the third conductor 40 to the outside. At least a part of the first feeding line 61 may be positioned in the base 20. The first feeding line 61 may face the outside from two zx planes, two yz planes, or two xy planes of the base 20.

The first feeding line 61 may be in contact with the third conductor 40 from the forward direction and the reverse direction of the z direction. The fourth conductor 50 may be omitted on the periphery of the first feeding line 61. The first feeding line 61 may be electromagnetically connected to the third conductor 40 through an opening of the fourth conductor 50. The first conductive layer 41 may be omitted on the periphery of the first feeding line 61. The first feeding line 61 may be connected to the second conductive layer 42 through an opening of the first conductive layer 41. The first feeding line 61 may be in contact with the third conductor 40 along the xy plane. The pair conductor 30 may be omitted on the periphery of the first feeding line 61. The first feeding line 61 may be connected to the third conductor 40 through an opening of the pair conductor 30. The first feeding line 61 is connected to a unit conductor of the third conductor 40 at a distance from the central portion of the unit conductor.

Figure 63:
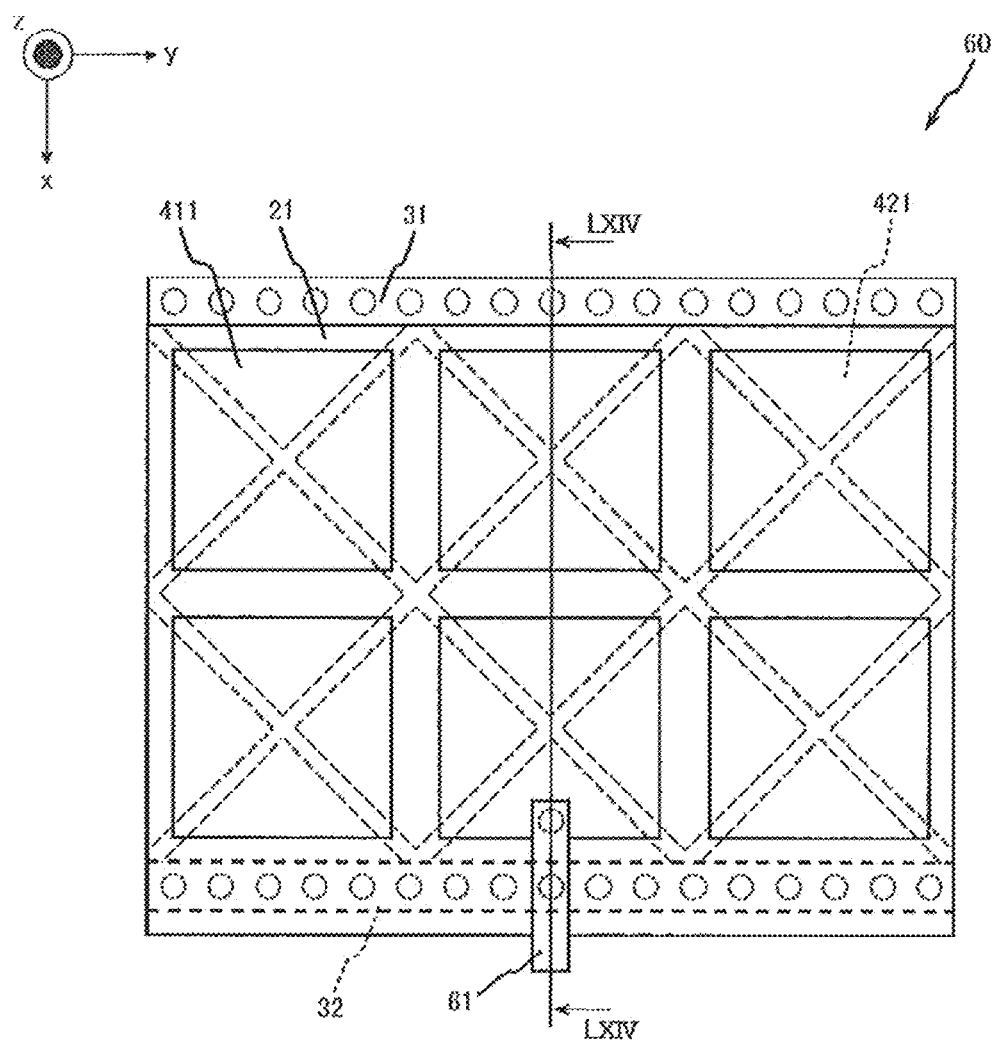
FIG. 63 is a planar view of an embodiment of an antenna.
Figure 64:
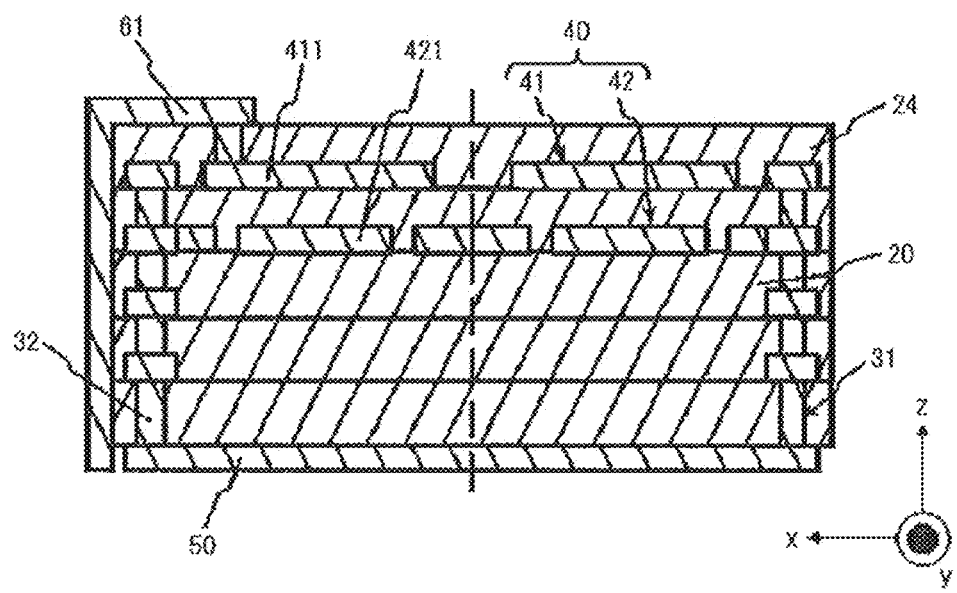
FIG. 64 is a cross-sectional view illustrating an embodiment of an antenna.

FIG. 63 is a planar view of the first antenna 60 on the xy plane from the z direction. FIG. 64 is a cross-sectional view taken along line LXIV-LXIV illustrated in FIG. 63. The first antenna 60 illustrated in FIGS. 63 and 64 has the third base 24 on the third conductor 40. The third base 24 has an opening on the first conductive layer 41. The first feeding line 61 is electrically connected to the first conductive layer 41 through the opening of the third base 24.

Figure 65:
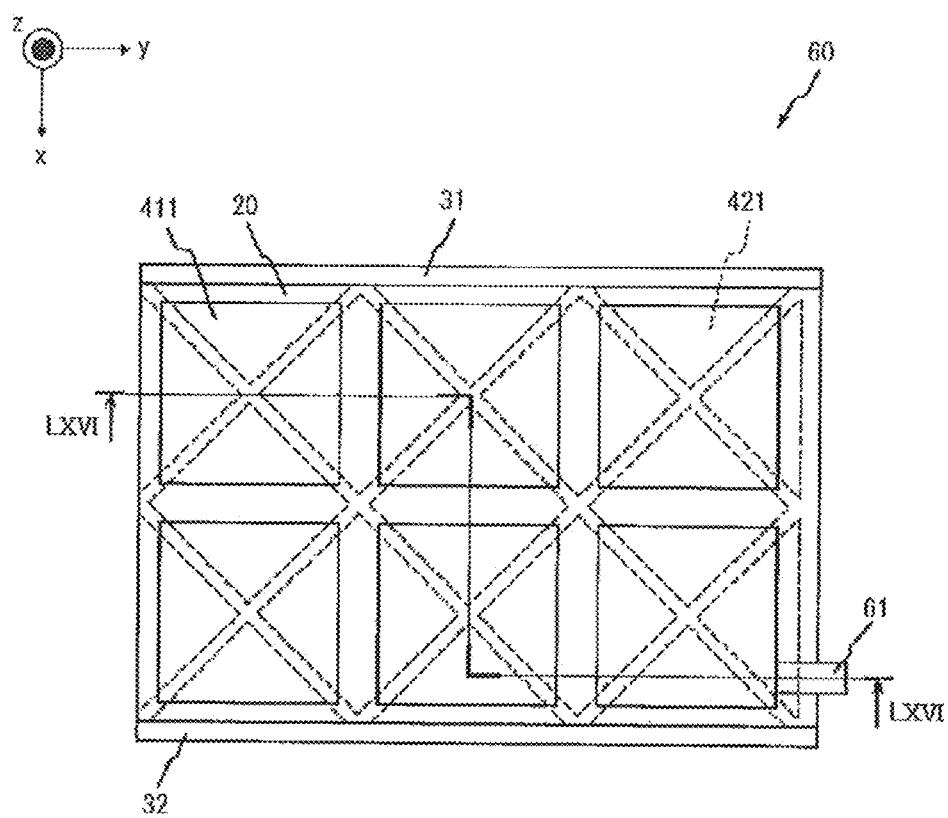
FIG. 65 is a planar view of an embodiment of an antenna.
Figure 66:
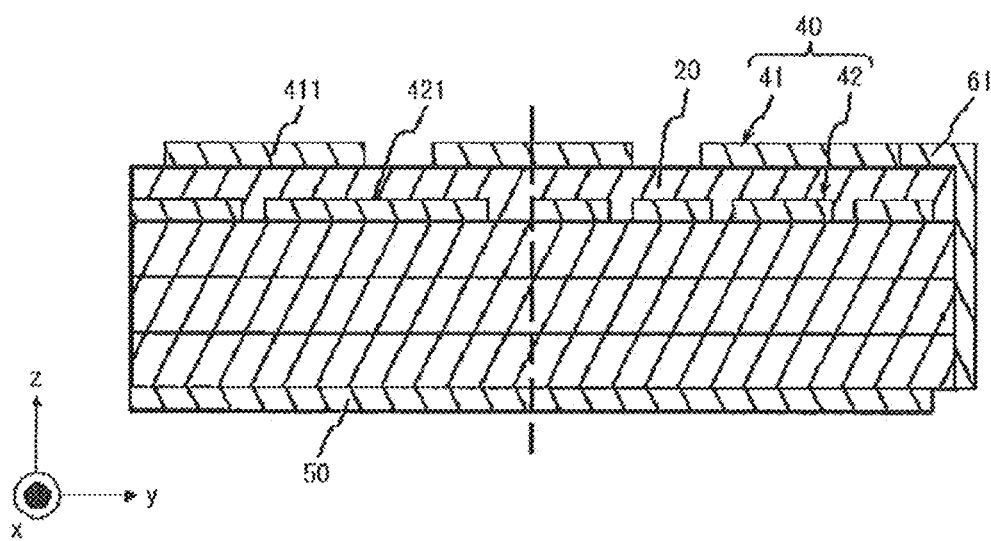
FIG. 66 is a cross-sectional view illustrating an embodiment of an antenna.

FIG. 65 is a planar view of the first antenna 60 on the xy plane from the z direction. FIG. 66 is a cross-sectional view taken along line LXVI-LXVI illustrated in FIG. 65. In the first antenna 60 illustrated in FIGS. 65 and 66, a part of the first feeding line 61 is positioned on the base 20. The first feeding line 61 may be connected to the third conductor 40 in the xy plane. The first feeding line 61 may be connected to the first conductive layer 41 in the xy plane. In an embodiment, the first feeding line 61 may be connected to the second conductive layer 42 in the xy plane.

Figure 67:
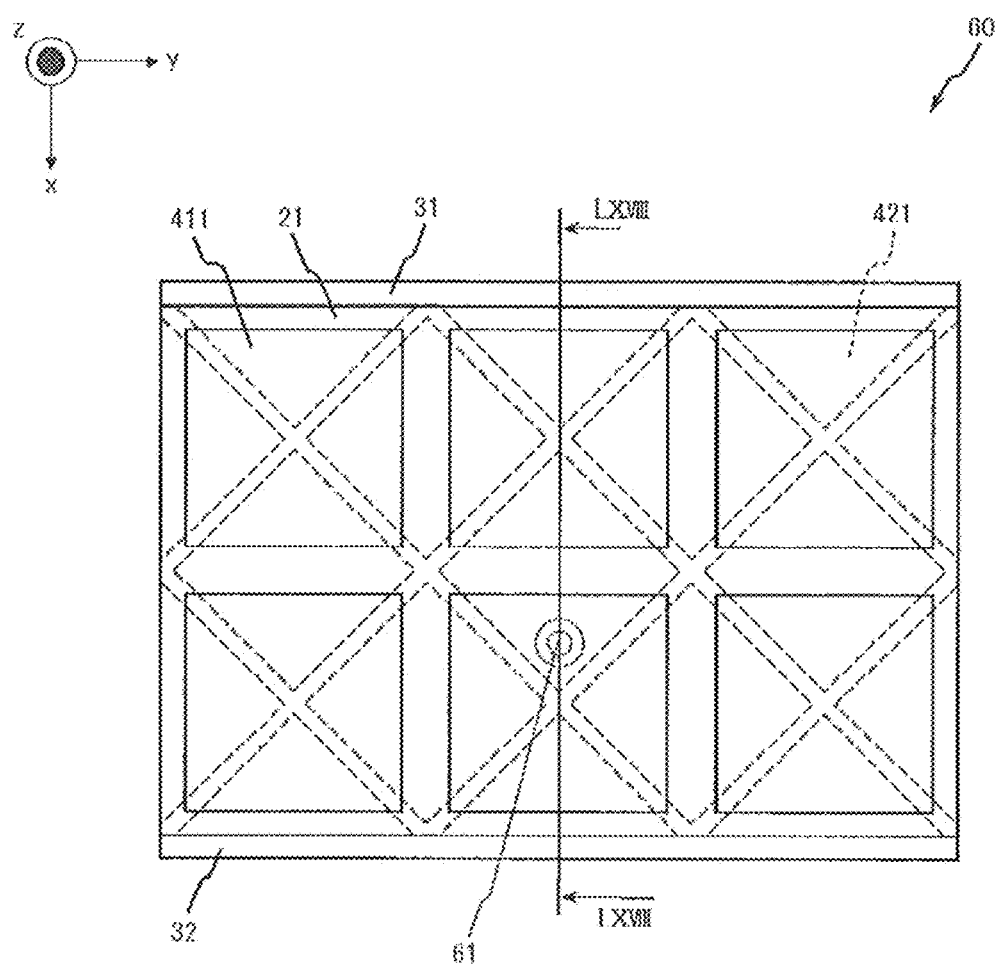
FIG. 67 is a planar view of an embodiment of an antenna.
Figure 68:
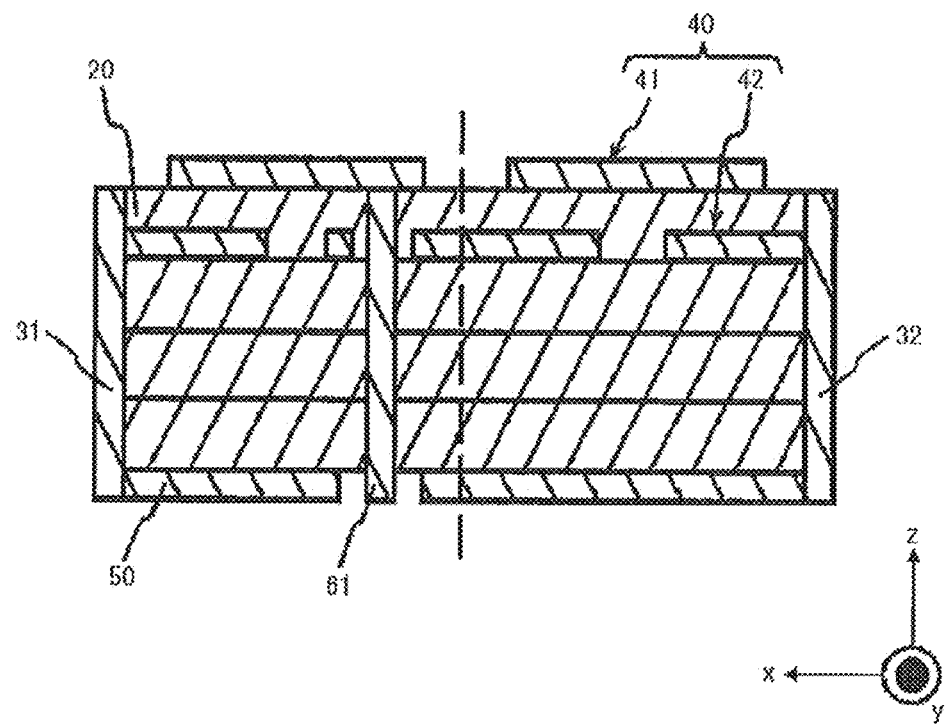
FIG. 68 is a cross-sectional view illustrating an embodiment of an antenna.

FIG. 67 is a planar view of the first antenna 60 on the xy plane from the z direction. FIG. 68 is a cross-sectional view taken along line LXVIII-LXVIII illustrated in FIG. 67. In the first antenna 60 illustrated in FIGS. 67 and 68, the first feeding line 61 is positioned in the base 20. The first feeding line 61 may be connected to the third conductor 40 from the reverse direction of the z direction. The fourth conductor 50 may have an opening. The fourth conductor 50 may have an opening at a position where it overlaps with the third conductor 40 as viewed in the z direction. The first feeding line 61 may face the outside of the base 20 through the opening.

Figure 69:
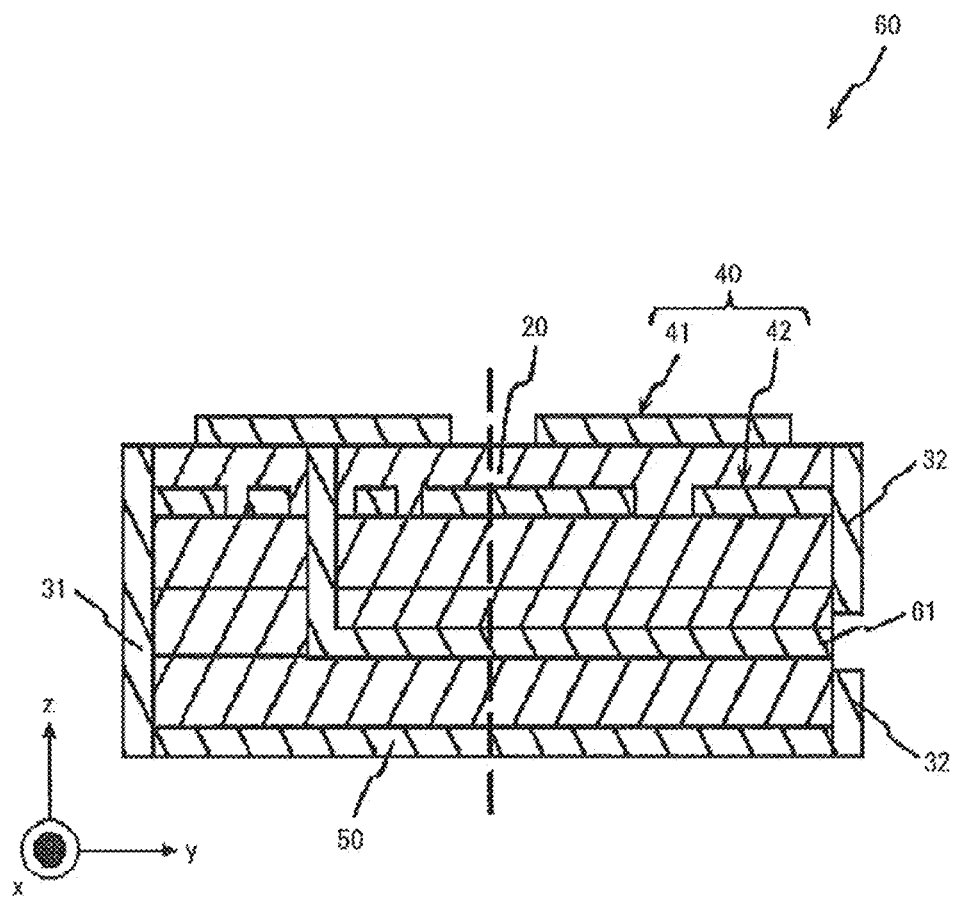
FIG. 69 is a cross-sectional view illustrating an embodiment of an antenna.

FIG. 69 is a cross-sectional view of the first antenna 60 when the yz plane is viewed from the x direction. The pair conductor 30 may have an opening. The first feeding line 61 may face the outside of the base 20 through the opening.

The electromagnetic wave emitted by the first antenna 60 has a polarization component in the x direction larger than a polarization component in the y direction in the first plane. The polarization component in the x direction attenuates less than a horizontal polarization component when a metal plate comes closer to the fourth conductor 50 from the z direction. The first antenna 60 may keep the radiation efficiency when a metal plate comes closer from the outside.

Figure 70:
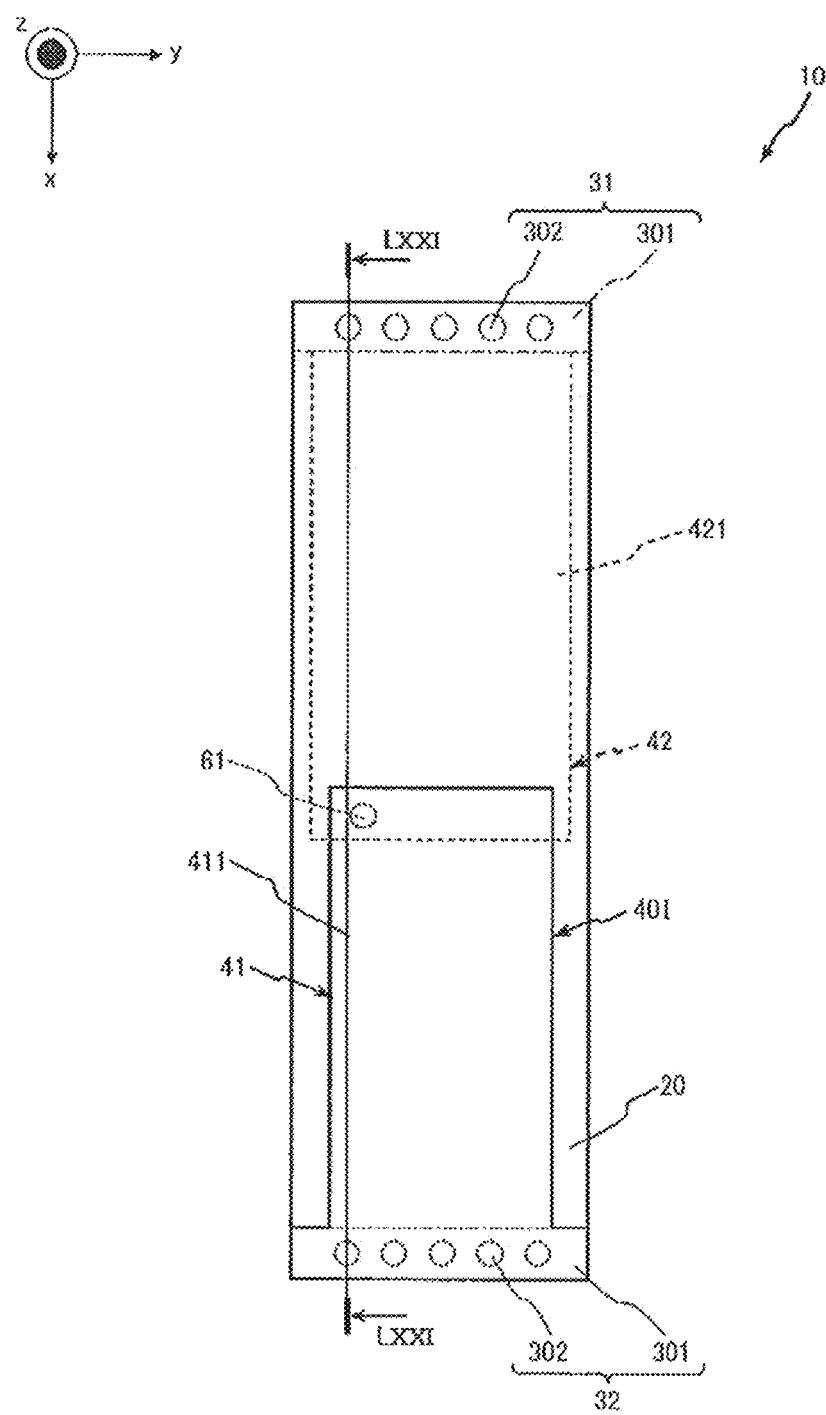
FIG. 70 is a planar view of an embodiment of an antenna.
Figure 71:
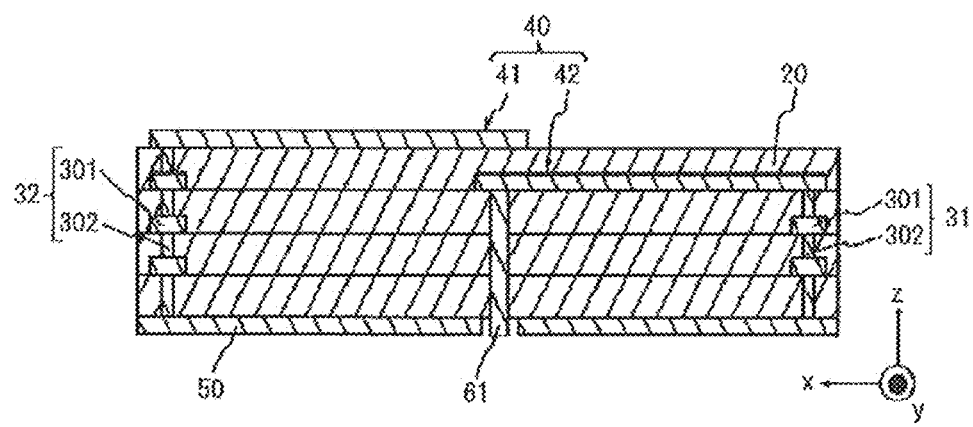
FIG. 71 is a cross-sectional view illustrating an embodiment of an antenna.
Figure 72:
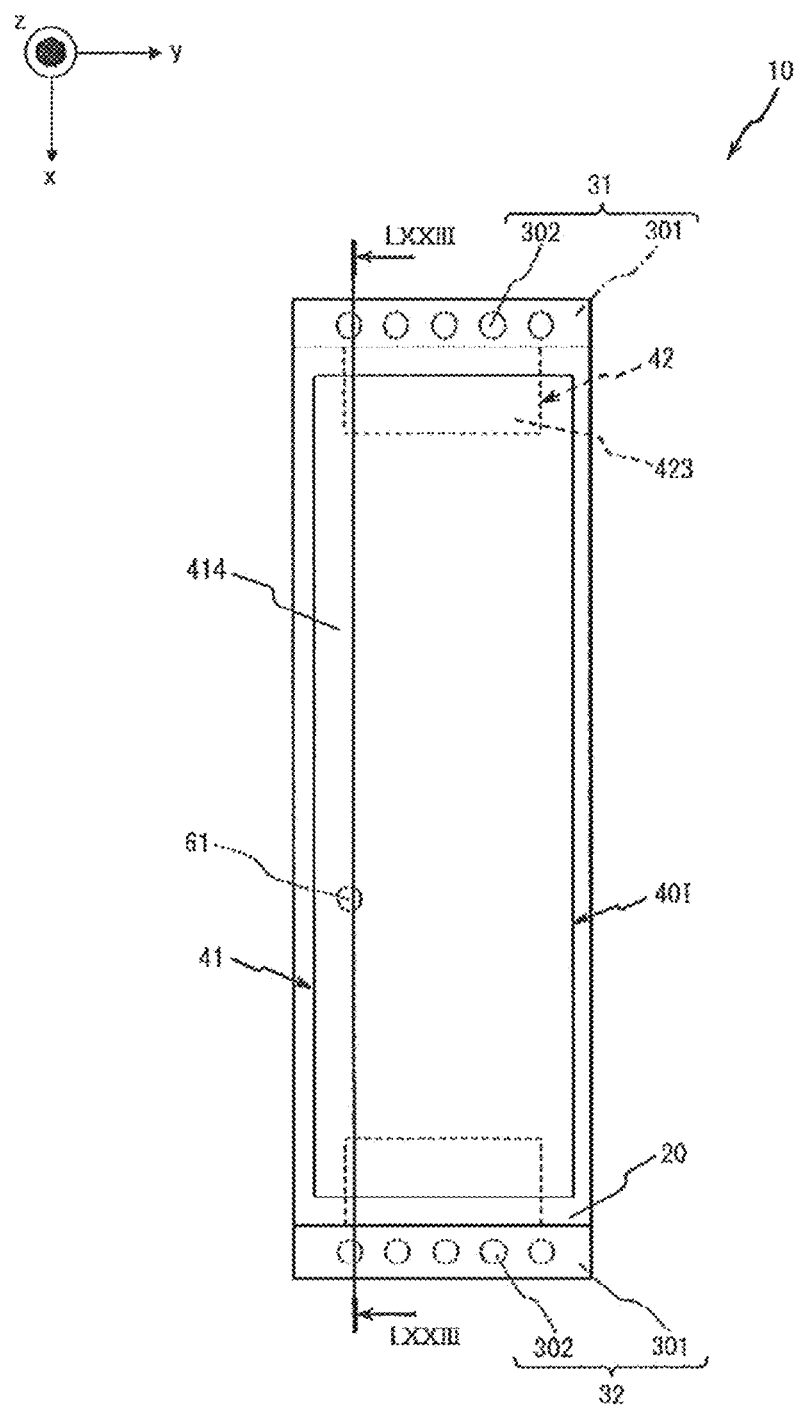
FIG. 72 is a planar view of an embodiment of an antenna.
Figure 73:
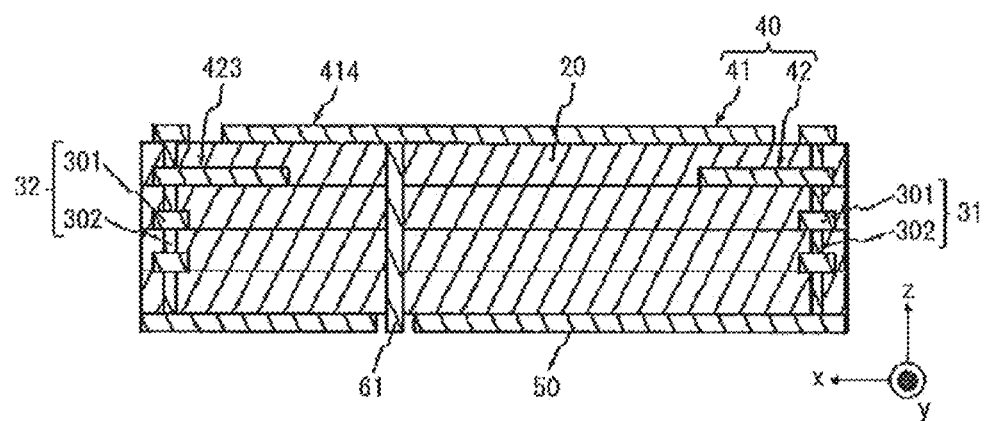
FIG. 73 is a cross-sectional view illustrating an embodiment of an antenna.
Figure 74:
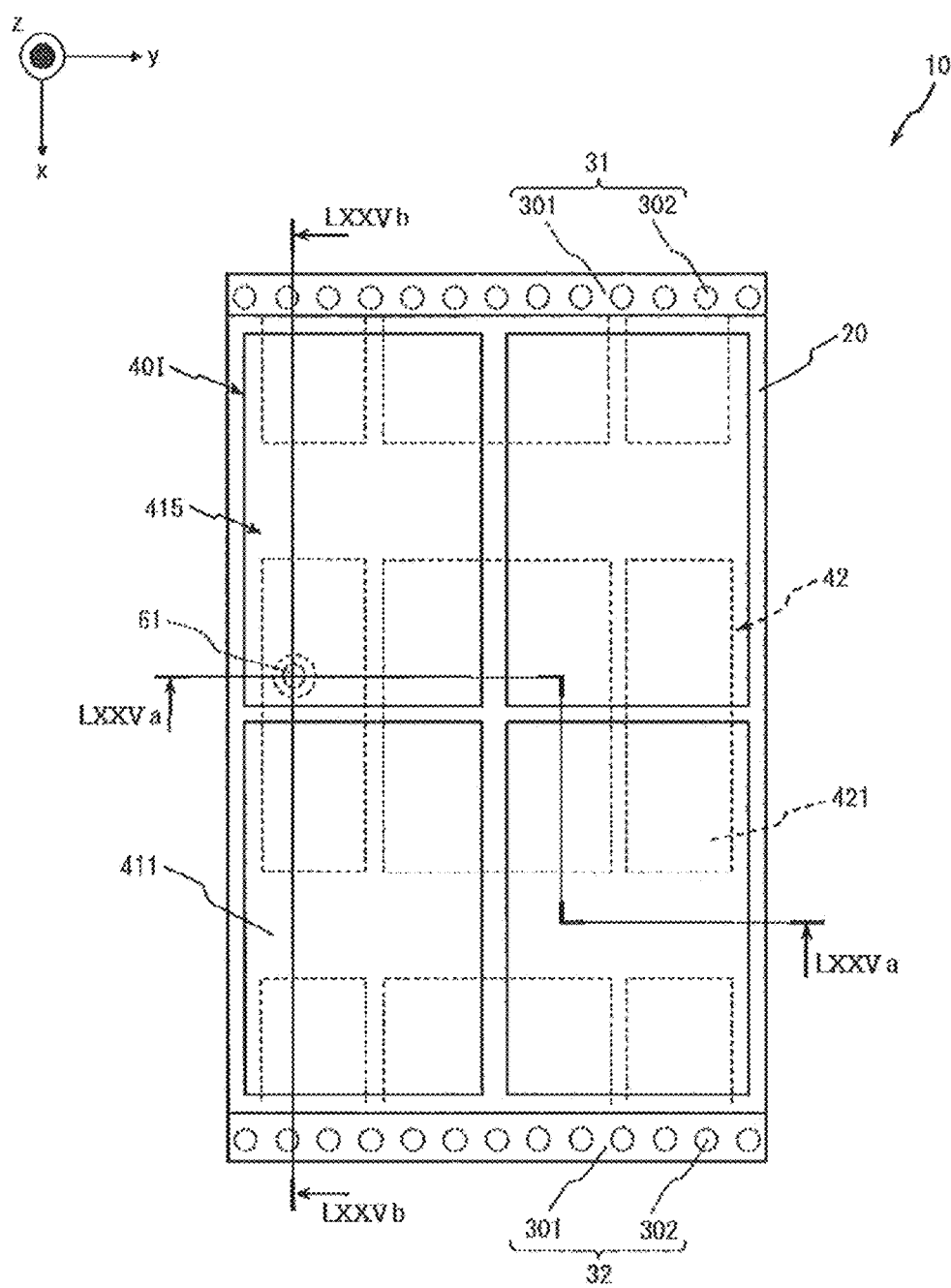
FIG. 74 is a planar view of an embodiment of an antenna.
Figure 75A:
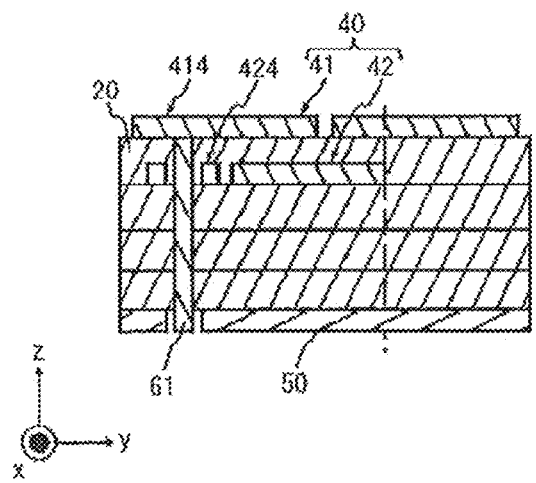
FIG. 75A is a cross-sectional view illustrating an embodiment of an antenna.
Figure 75B:
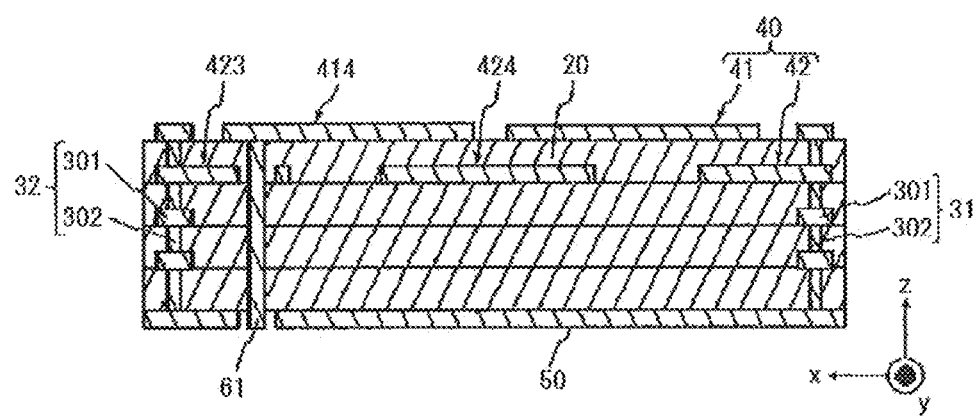
FIG. 75B is a cross-sectional view illustrating an embodiment of an antenna.
Figure 76:
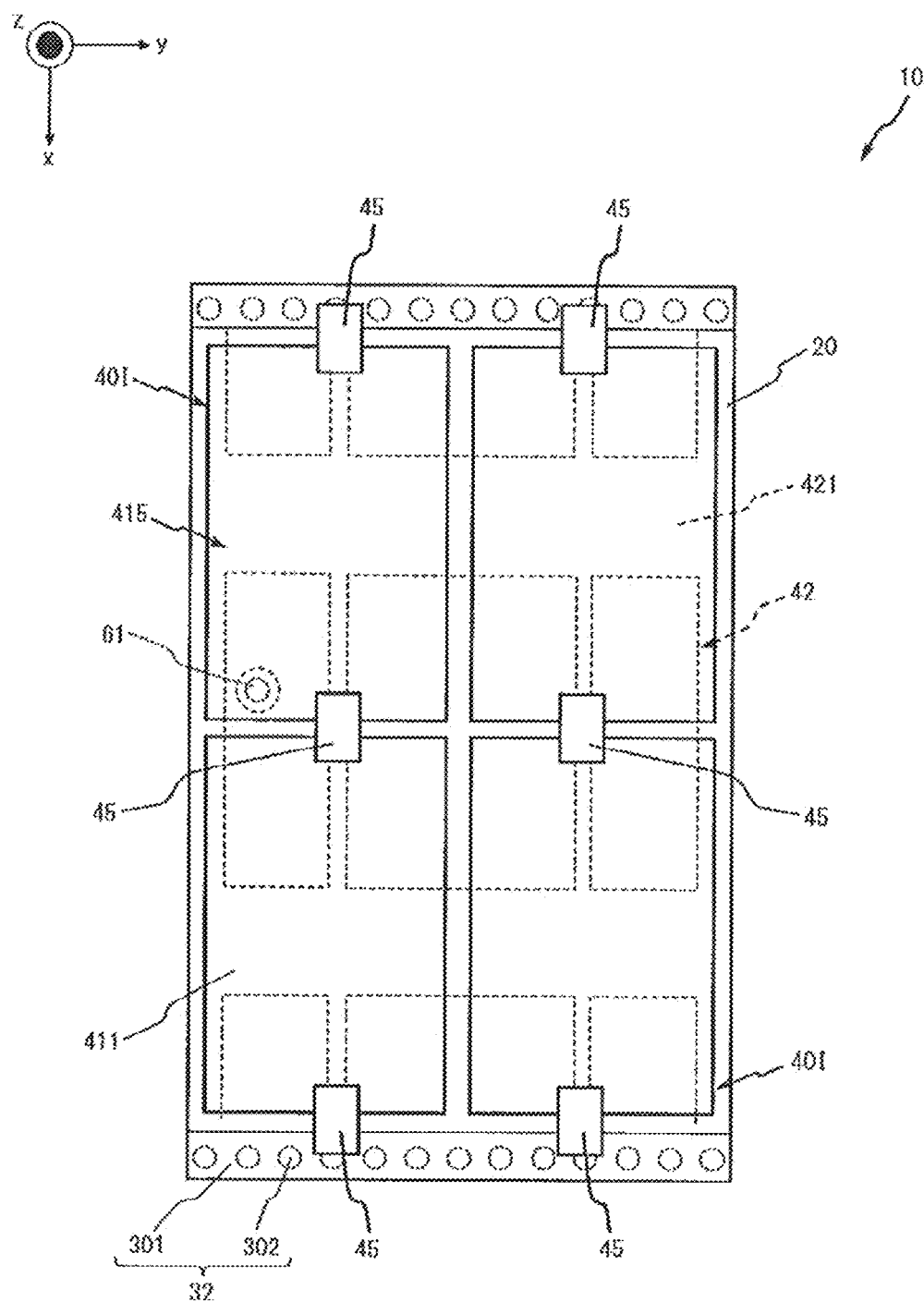
FIG. 76 is a planar view of an embodiment of an antenna.

FIG. 70 illustrates another example of the first antenna 60. FIG. 71 is a cross-sectional view taken along line LXXI-LXXI illustrated in FIG. 70. FIG. 72 illustrates another example of the first antenna 60. FIG. 73 is a cross-sectional view taken along line LXXIII-LXXIII illustrated in FIG. 72. FIG. 74 illustrates another example of the first antenna 60. FIG. 75A is a cross-sectional view taken along line LXXVa-LXXVa illustrated in FIG. 74. FIG. 75B is a cross-sectional view taken along line LXXVb-LXXVb illustrated in FIG. 74. FIG. 76 illustrates another example of the first antenna 60. The first antenna 60 illustrated in FIG. 76 has an impedance element 45.

The first antenna 60 can change the operating frequency by the impedance element 45. The first antenna 60 includes a first feeding conductor 415 connected to the first feeding line 61 and a first unit conductor 411 not connected to the first feeding line 61. Impedance match changes when the impedance element 45 is connected to the first feeding conductor 415 and another conductive body. In the first antenna 60, impedance matching can be adjusted by connecting the first feeding conductor 415 and another conductive body by the impedance element 45. In the first antenna 60, the impedance element 45 may be inserted between the first feeding conductor 415 and another conductive body in order to adjust impedance match. In the first antenna 60, the impedance element 45 may be inserted between two first unit conductors 411 not connected to the first feeding line 61 in order to adjust the operating frequency. In the first antenna 60, the impedance element 45 may be inserted between the first unit conductor 411 not connected to the first feeding line 61 and any one of the pair conductors 30 in order to adjust the operating frequency.

The second antenna 70 includes a base 20, pair conductors 30, a third conductor 40, a fourth conductor 50, a second feeding layer 71, and a second feeding line 72. In an example, the third conductor 40 is positioned in the base 20. In an example, the second antenna 70 has a third base 24 on the base 20. The third base 24 may have a composition different from the base 20. The third base 24 may be positioned on the third conductor 40. The third base 24 may be positioned on the second feeding layer 71.

The second feeding layer 71 is positioned above the third conductor 40 with a space. The base 20 or the third base 24 may be positioned between the second feeding layer 71 and the third conductor 40. The second feeding layer 71 includes line-type, patch-type, and slot-type resonators. The second feeding layer 71 may be referred to as an antenna element. In an example, the second feeding layer 71 may be electromagnetically coupled to the third conductor 40. The resonance frequency of the second feeding layer 71 changes from an independent resonance frequency by electromagnetic coupling with the third conductor 40. In an example, the second feeding layer 71 receives transmission of power from the second feeding line 72 and resonates together with the third conductor 40. In an example, the second feeding layer 71 receives transmission of power from the second feeding line 72 and resonates together with the third conductor 40 and the third conductor.

The second feeding line 72 is electrically connected to the second feeding layer 71. In an embodiment, the second feeding line 72 transmits power to the second feeding layer 71. In an embodiment, the second feeding line 72 transmits power from the second feeding layer 71 to the outside.

Figure 77:
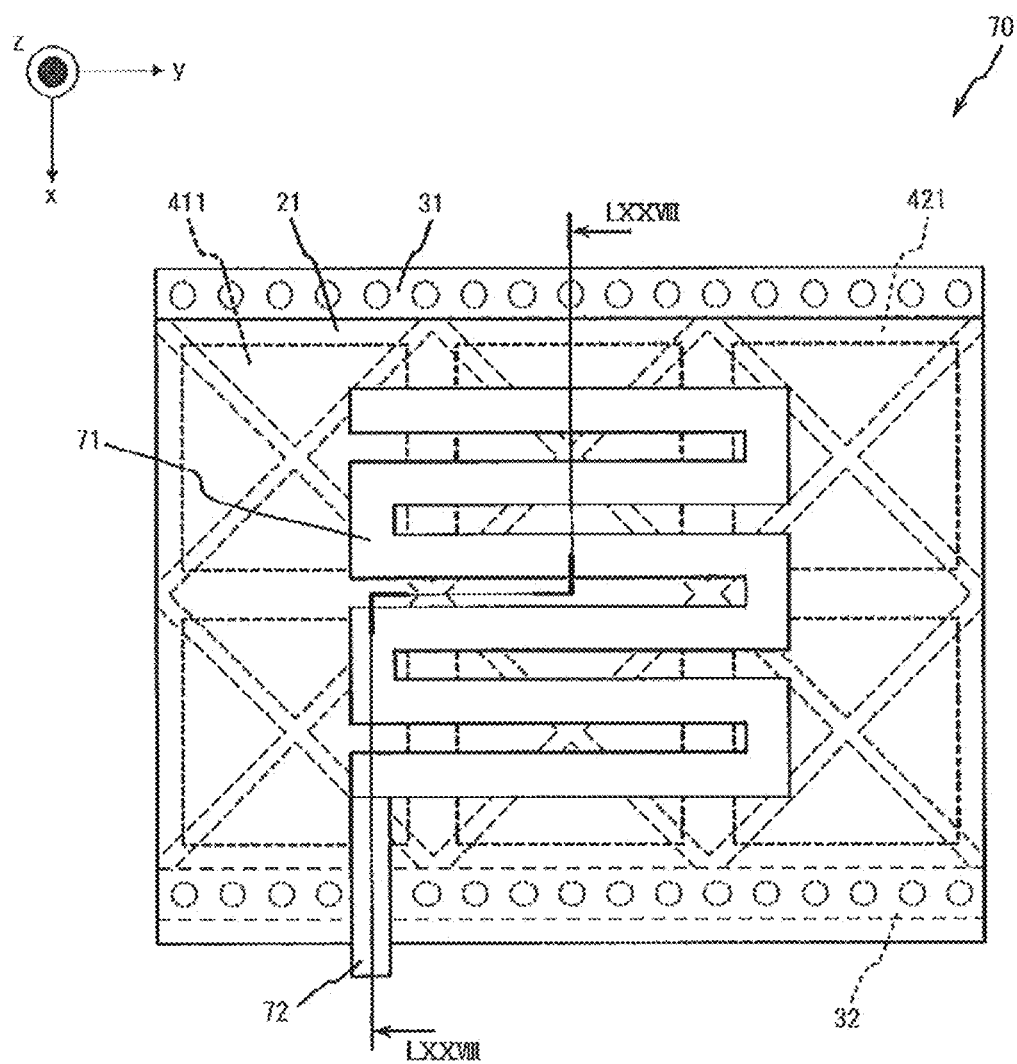
FIG. 77 is a planar view of an embodiment of an antenna.
Figure 78:
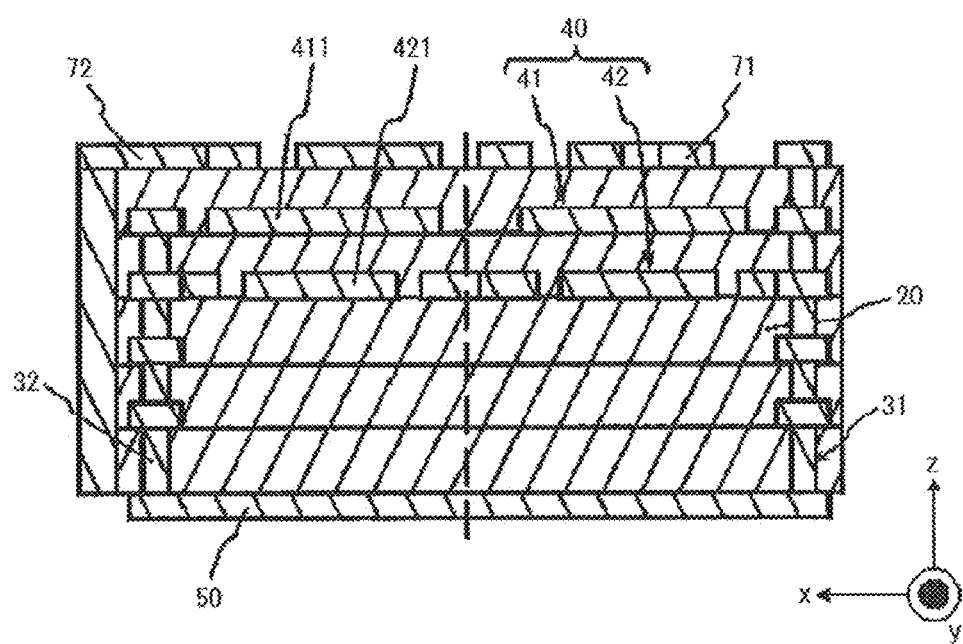
FIG. 78 is a cross-sectional view of the antenna illustrated in FIG. 43.

FIG. 77 is a planar view of the second antenna 70 on the xy plane from the z direction. FIG. 78 is a cross-sectional view taken along line LXXVIII-LXXVIII in FIG. 77. In the second antenna 70 illustrated in FIGS. 77 and 78, the third conductor 40 is positioned in the base 20. The second feeding layer 71 is positioned on the base 20. The second feeding layer 71 is positioned overlapping with the unit structure 10X as viewed in the z direction. The second feeding line 72 is positioned on the base 20. The second feeding line 72 is electromagnetically connected to the second feeding layer 71 in the xy plane.

(Wireless Communication Module)

Figure 79:
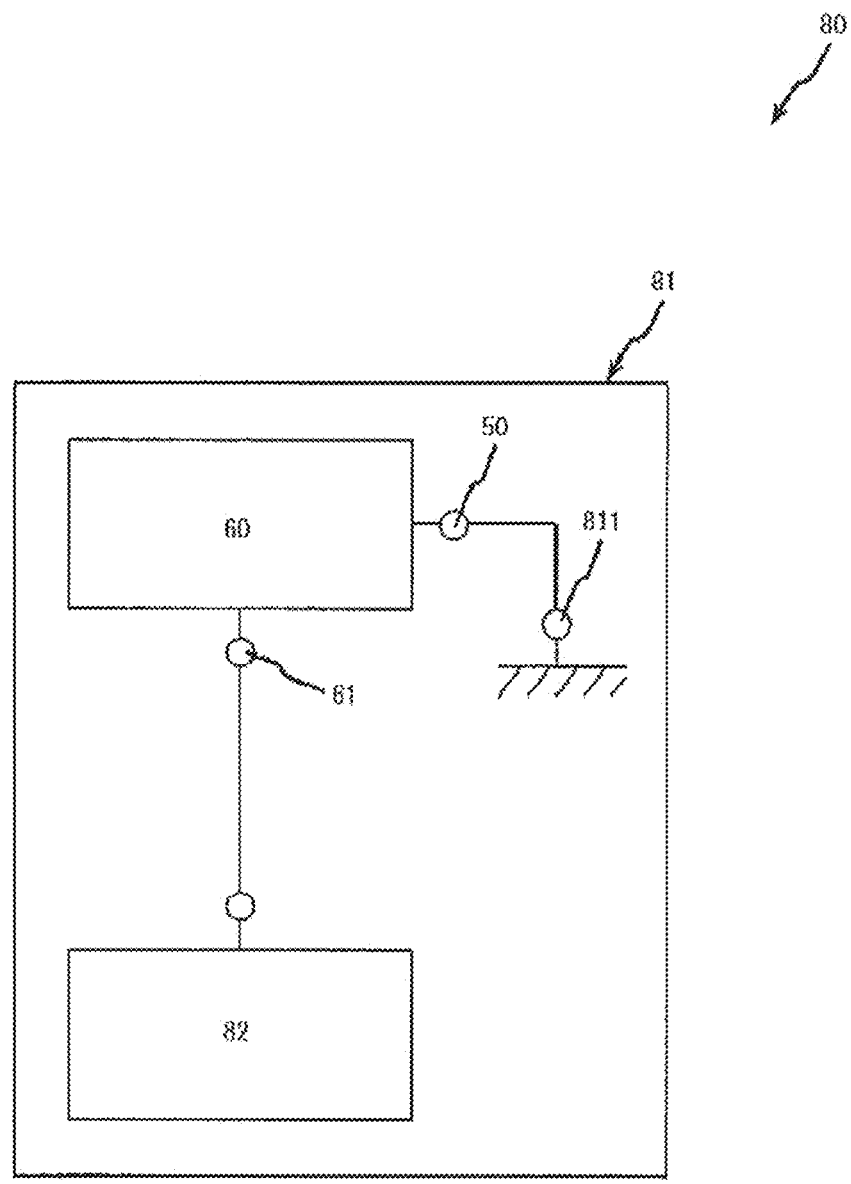
FIG. 79 is a block diagram illustrating an embodiment of a wireless communication module.
Figure 80:
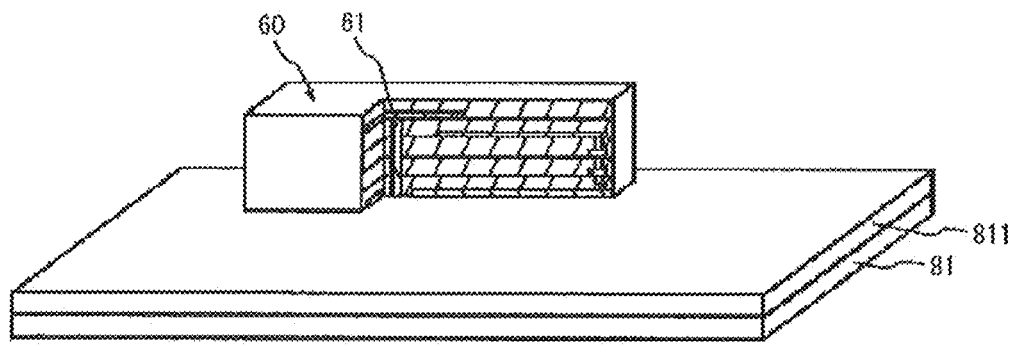
FIG. 80 is a perspective view partly in section illustrating an embodiment of a wireless communication module.

A wireless communication module in the present disclosure includes a wireless communication module 80 as an example of a plurality of embodiments. FIG. 79 is a block structure diagram of the wireless communication module 80. FIG. 80 is a schematic configuration diagram of the wireless communication module 80. The wireless communication module 80 includes a first antenna 60, a circuit board 81, and an RF module 82. The wireless communication module 80 may include a second antenna 70 instead of the first antenna 60.

The first antenna 60 is positioned on the circuit board 81. The first feeding line 61 of the first antenna 60 is electromagnetically connected to the RF module 82 through the circuit board 81. The fourth conductor 50 of the first antenna 60 is electromagnetically coupled to a ground conductor 811 of the circuit board 81.

The ground conductor 811 may extend on the xy plane. The surface integral of the ground conductor 811 on the xy plane is larger than that of the fourth conductor 50. The ground conductor 811 is longer than the fourth conductor 50 in the y direction. The ground conductor 811 is longer than the fourth conductor 50 in the x direction. The first antenna 60 may be positioned on the end side with respect to the center of the ground conductor 811 in the y direction. The center of the first antenna 60 may differ from the center of the ground conductor 811 on the xy plane. The center of the first antenna 60 may differ from the centers of the first conductor 41 and the second conductor 42. The point at which the first feeding line 61 is connected to the third conductor 40 may differ from the center of the ground conductor 811 on the xy plane.

In the first antenna 60, first current and second current loop through the pair conductors 30. The first antenna 60 is positioned on the end side in the y direction with respect to the center of the ground conductor 811, whereby the second current flowing through the ground conductor 811 is asymmetric. When the second current flowing through the ground conductor 811 is asymmetric, the antenna structure including the first antenna 60 and the ground conductor 811 has a larger polarization component in the x direction of radiation waves. Increasing the polarization component in the x direction of radiation waves can improve the total radiation efficiency.

The RF module 82 may control power supplied to the first antenna 60. The RF module 82 modulates a baseband signal and supplies the modulated signal to the first antenna 60. The RF module 82 may modulate an electrical signal received by the first antenna 60 to a baseband signal.

In the first antenna 60, variation in resonance frequency is small because of the conductor on the circuit board 81 side. The wireless communication module 80 has the first antenna 60 and thereby can reduce the effect from an external environment.

The first antenna 60 may be integrally configured with the circuit board 81. When the first antenna 60 and the circuit board 81 are integrally configured, the fourth conductor 50 and the ground conductor 811 are integrally configured.

(Wireless Communication Device)

Figure 81:
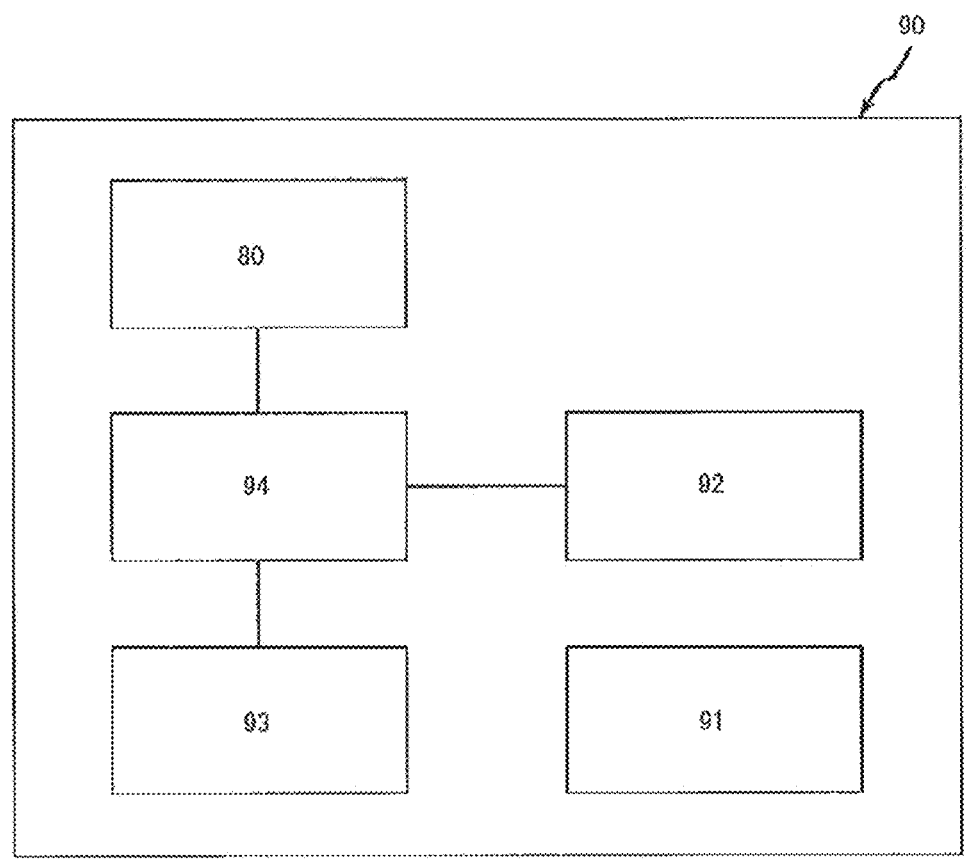
FIG. 81 is a block diagram illustrating an embodiment of a wireless communication device.
Figure 82:
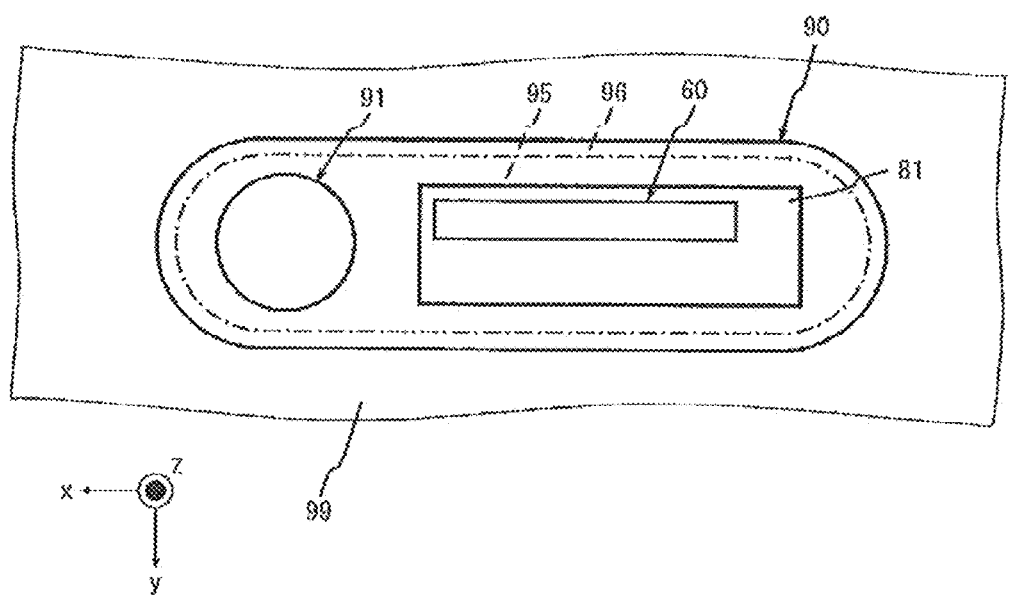
FIG. 82 is a planar view illustrating an embodiment of a wireless communication device.
Figure 83:
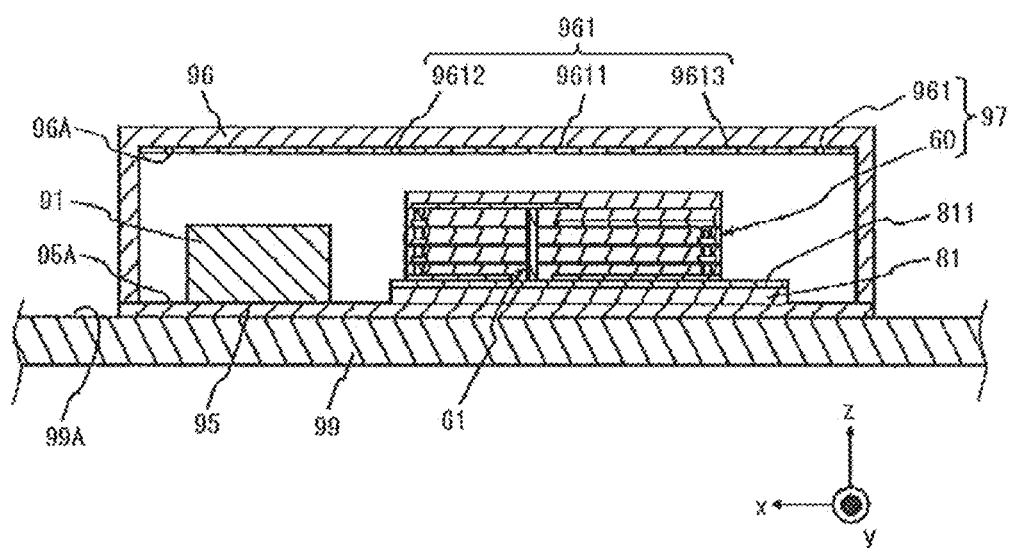
FIG. 83 is a cross-sectional view illustrating an embodiment of a wireless communication device.
Figure 84:
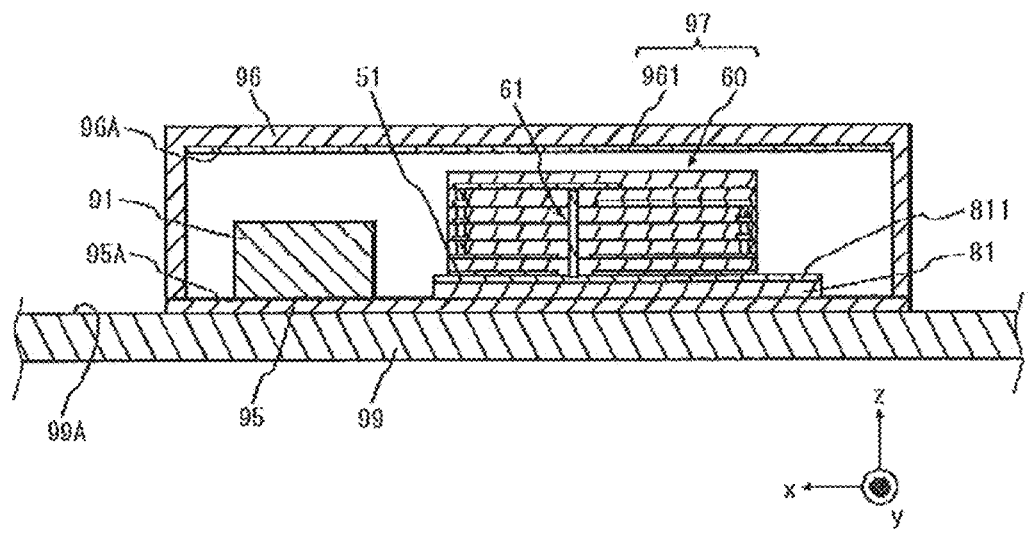
FIG. 84 is a planar view illustrating an embodiment of a wireless communication device.

A wireless communication device in the present disclosure includes a wireless communication device 90 as an example of a plurality of embodiments. FIG. 81 is a block structure diagram of the wireless communication device 90. FIG. 82 is a planar view of the wireless communication device 90. In the wireless communication device 90 illustrated in FIG. 82, a part of the configuration is omitted. FIG. 83 is a cross-sectional view of the wireless communication device 90. In the wireless communication device 90 illustrated in FIG. 83, a part of the configuration is omitted. The wireless communication device 90 includes a wireless communication module 80, a battery 91, a sensor 92, a memory 93, a controller 94, a first case 95, and a second case 96. The wireless communication module 80 of the wireless communication device 90 has the first antenna 60 but may have the second antenna 70. FIG. 84 illustrates one of other embodiments of the wireless communication device 90. The first antenna 60 of the wireless communication device 90 may have the reference potential layer 51.

Figure 90:
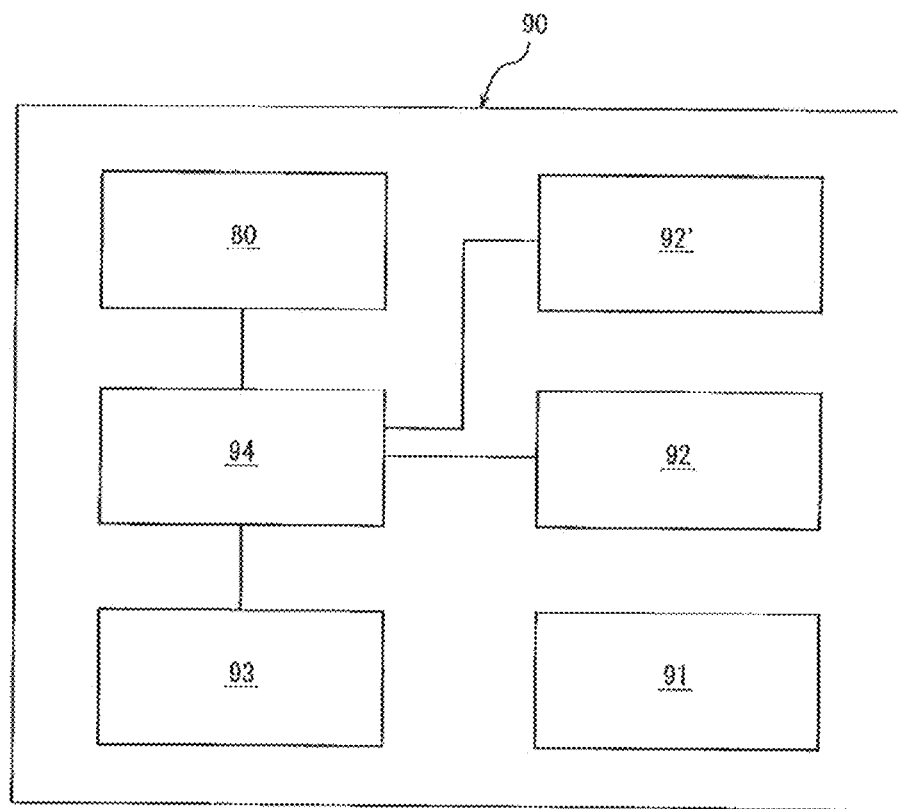
FIG. 90 is a block diagram illustrating an embodiment of a wireless communication device.

As illustrated in FIG. 90, in other embodiments, the wireless communication device 90 may include an output device 92' in addition to the wireless communication module 80, the battery 91, the sensor 92, the memory 93, and the controller 94. The wireless communication device 90 may include a plurality of sensors 92 and a plurality of output devices 92'. The wireless communication device 90 may include a plurality of sets each including the wireless communication module 80, the sensor 92, the memory 93, the controller 94, and the output device 92'. In a configuration including two sets, one of the sets includes the first antenna 60 or the second antenna 70 as a tenth antenna. The other set includes the first antenna 60 or the second antenna 70 as a twentieth antenna different from the tenth antenna. The wireless communication device 90 may include the first case 95 and the second case 96 containing the wireless communication module 80 and the like.

Figure 91:
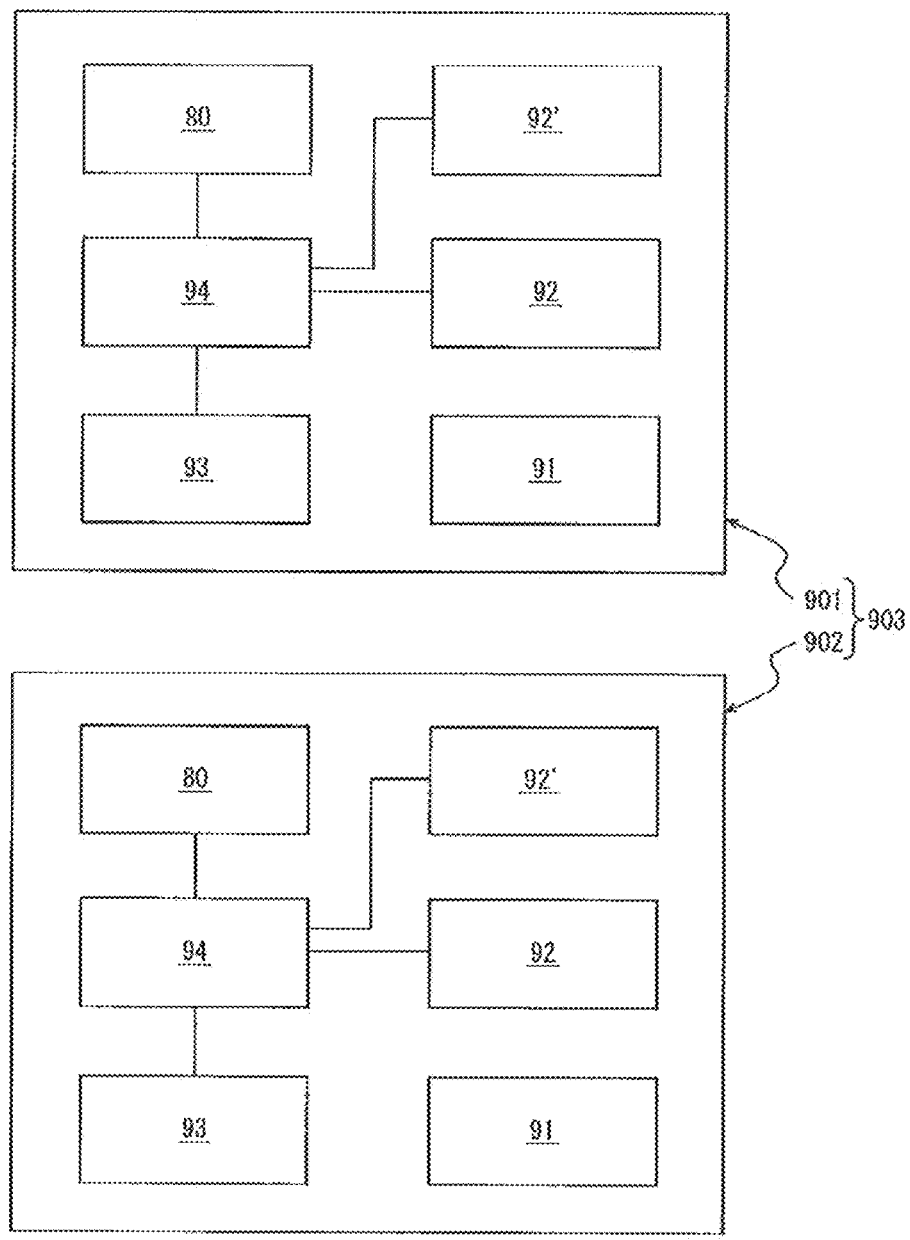
FIG. 91 is a block diagram illustrating an embodiment of a communication system.

In other embodiments, as illustrated in FIG. 91, a plurality of wireless communication devices at least including a first wireless communication device 901 and a second wireless communication device 902 may constitute a communication system 903. The first wireless communication device 901 includes a wireless communication module 80 including the first antenna 60 or the second antenna 70 as a tenth antenna, a battery 91, a sensor 92, a memory 93, a controller 94, and an output device 92'. The first wireless communication device 901 may include the first case 95 and the second case 96 containing the wireless communication module 80 and the like. The second wireless communication device 902 includes a wireless communication module 80 including the first antenna 60 or the second antenna 70 as a twentieth antenna, a battery 91, a sensor 92, a memory 93, a controller 94, and an output device 92'. The second wireless communication device 902 may include the first case 95 and the second case 96 containing the wireless communication module 80 and the like.

The battery 91 supplies power to the wireless communication module 80. The battery 91 may supply power to at least one of the sensor 92, the memory 93, and the controller 94. The battery 91 may include at least one of a primary battery and a secondary battery. The negative electrode of the battery 91 is electrically connected to the ground terminal of the circuit board 81. The negative electrode of the battery 91 is electrically connected to the fourth conductor 50 of the antenna 60.

Examples of the sensor 92 may include, but are not limited to, a speed sensor, a vibration sensor, an acceleration sensor, a gyro sensor, a rotation angle sensor, an angular velocity sensor, a geomagnetic sensor, a magnet sensor, a temperature sensor, a humidity sensor, an atmospheric pressure sensor, an optical sensor, an illuminance sensor, a UV sensor, a gas sensor, a gas concentration sensor, an atmosphere sensor, a level sensor, an odor sensor, a pressure sensor, an air pressure sensor, a contact sensor, a wind power sensor, an infrared sensor, a human detecting sensor, a displacement sensor, an image sensor, a weight sensor, a smoke sensor, a liquid leakage sensor, a vital sensor, a battery level sensor, an ultrasonic sensor, and a receiver device of Global Positioning System (GPS) signals.

In other embodiments, examples of the sensor 92 may include, but are not limited to, a sound sensor such as a microphone, and a living body sensor such as a body temperature sensor and a pulsation sensor.

Examples of the output device 92' may include, but are not limited to, a speaker for outputting sound, a vibrator for outputting vibration, a Peltier element and a heating element for changing the temperature, a device for diffusing perfume, and a display for displaying an image.

Examples of the memory 93 may include, but are not limited to, a semiconductor memory. The memory 93 may function as a work memory for the controller 94. The memory 93 may be included in the controller 94. The memory 93 stores, for example, a computer program describing the processing for implementing each function of the wireless communication device 90 and information used for the processing in the wireless communication device 90.

The memory 93 stores, for example, a computer program describing the processing for implementing each function of the wireless communication device 90 and information used for the processing in the wireless communication device 90.

The information stored in the memory 93 may include, for example, information for the wireless communication device 90 to perform wireless communication with the electronic device 12. As the information used to perform wireless communication, the memory 93 may store, for example, information such as a communication protocol for implementing communication with the electronic device 12.

The controller 94 may include, for example, a processor. The controller 94 may include one or more processors. The processor may include a general-purpose processor that reads a specific computer program to execute a specific function and a dedicated processor dedicated to a certain process. The dedicated processor may include an IC dedicated to a specific application. The IC dedicated to a specific application may be called an application specific integrated circuit (ASIC). The processor may include a programmable logic device. The programmable logic device may be called a PLD. The PLD may include a field-programmable gate array (FPGA). The controller 94 may be one of a system-on-a-chip (SoC) and a system in a package (SiP), in which one or more processors cooperate. The controller 94 may store, for example, a variety of information or a computer program for operating each component of the wireless communication device 90 in the memory 93.

The controller 94 generates a transmission signal to be transmitted from the wireless communication device 90. The controller 94 may acquire, for example, measurement data from the sensor 92. The controller 94 may generate a transmission signal in accordance with measurement data. The controller 94 may transmit a baseband signal to the RF module 82 of the wireless communication module 80.

The controller 94 may drive the output device 92' based on a reception signal received by the wireless communication device 90.

The first case 95 and the second case 96 protect another device of the wireless communication device 90. The first case 95 may extend in the xy plane. The first case 95 supports the other devices. The first case 95 may support the wireless communication module 80. The wireless communication module 80 is positioned on an upper surface 95A of the first case 95. The first case 95 may support the battery 91. The battery 91 is positioned on the upper surface 95A of the first case 95. In an example of a plurality of embodiments, the wireless communication module 80 and the battery 91 are arranged along the x direction on the upper surface 95A of the first case 95. The first conductor 31 is positioned between the battery 91 and the third conductor 40. The battery 91 is positioned beyond the pair conductor 30 as viewed from the third conductor 40.

The second case 96 may cover the other devices. The second case 96 includes an under surface 96A positioned on the z direction side of the first antenna 60. The under surface 96A extends along the xy plane. The under surface 96A is not necessarily flat and may include protrusions and depressions. The second case 96 may have an eighth conductor 961. The eighth conductor 961 is positioned on at least one of the interior, the outside, and the inside of the second case 96. The eighth conductor 961 is positioned on at least one of the upper surface and the side surface of the second case 96.

The eighth conductor 961 is opposed to the first antenna 60. A first body 9611 of the eighth conductor 961 is opposed to the first antenna 60 in the z direction. The eighth conductor 961 may include, in addition to the first body 9611, at least one of a second body opposed to the first antenna 60 in the x direction and a third body opposed to the first antenna in the y direction. A part of the eighth conductor 961 is opposed to the battery 91.

The eighth conductor 961 may include a first extra-body 9612 extending to the outside of the first conductor 31 in the x direction. The eighth conductor 961 may include a second extra-body 9613 extending to the outside of the second conductor 32 in the x direction. The first extra-body 9612 may be electrically connected to the first body 9611. The second extra-body 9613 may be electrically connected to the first body 9611. The first extra-body 9612 of the eighth conductor 961 is opposed to the battery 91 in the z direction. The eighth conductor 961 may be capacitively coupled to the battery 91. Capacitance may exist between the eighth conductor 961 and the battery 91.

The eighth conductor 961 is spaced apart from the third conductor 40 of the first antenna 60. The eighth conductor 961 is not electrically connected to the conductors of the first antenna 60. The eighth conductor 961 may be spaced apart from the first antenna 60. The eighth conductor 961 may be electromagnetically coupled to any conductor of the first antenna 60. The first body 9611 of the eighth conductor 961 may be electromagnetically coupled to the first antenna 60. When viewed two-dimensionally from the z direction, the first body 9611 may overlap with the third conductor 40. When the first body 9611 overlaps with the third conductor 40, propagation by electromagnetic coupling may increase. The electromagnetic coupling of the eighth conductor 961 with the third conductor 40 may be mutual inductance.

The eighth conductor 961 extends in the x direction. The eighth conductor 961 extends along the xy plane. The length of the eighth conductor 961 is longer than the length along the x direction of the first antenna 60. The length along the x direction of the eighth conductor 961 is longer than the length along the x direction of the first antenna 60. The length of the eighth conductor 961 may be longer than ½ of the operating wavelength λ of the wireless communication device 90. The eighth conductor 961 may include a section extending in the y direction. The eighth conductor 961 may be curved in the xy plane. The eighth conductor 961 may include a section extending in the z direction. The eighth conductor 961 may be curved from the xy plane to the yz plane or the zx plane.

Figure 85:
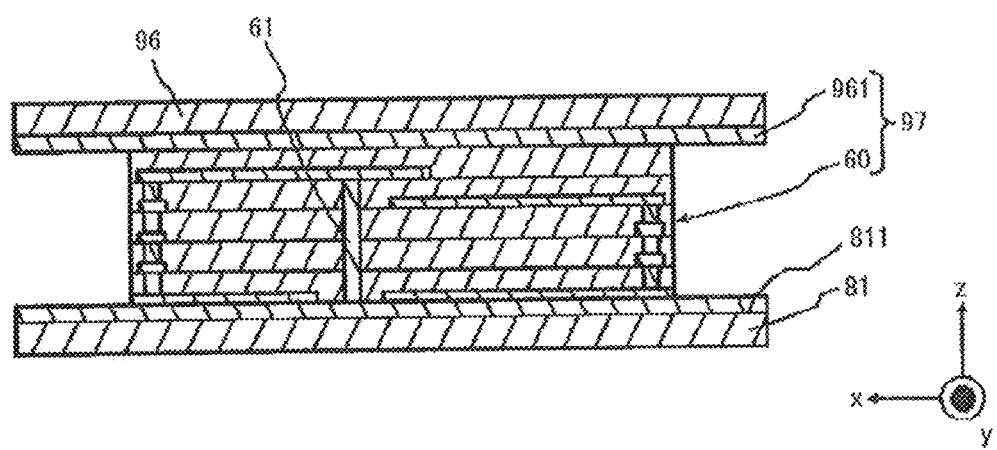
FIG. 85 is a cross-sectional view illustrating an embodiment of a wireless communication device.

In the wireless communication device 90 including the eighth conductor 961, the first antenna 60 and the eighth conductor 961 may be electromagnetically coupled to function as a third antenna 97. The operating frequency $f_c$ of the third antenna 97 may be different from the resonance frequency of the first antenna 60 alone. The operating frequency $f_c$ of the third antenna 97 may be closer to the resonance frequency of the first antenna 60 than to the resonance frequency of the eighth conductor 961 alone. The operating frequency $f_c$ of the third antenna 97 may fall within the resonance frequency band of the first antenna 60. The operating frequency $f_c$ of the third antenna 97 may fall outside the resonance frequency band of the eighth conductor 961 alone. FIG. 85 illustrates other embodiments of the third antenna 97. The eighth conductor 961 may be configured integrally with the first antenna 60. In FIG. 85, the configuration of a part of the wireless communication device 90 is omitted. In the example in FIG. 85, the second case 96 does not necessarily include the eighth conductor 961.

In the wireless communication device 90, the eighth conductor 961 is capacitively coupled to the third conductor 40. The eighth conductor 961 is electromagnetically coupled to the fourth conductor 50. The third antenna 97 includes the first extra-body 9612 and the second extra-body 9613 of the eighth conductor and thereby improves in gain compared with the first antenna 60 in the air.

Figure 86:
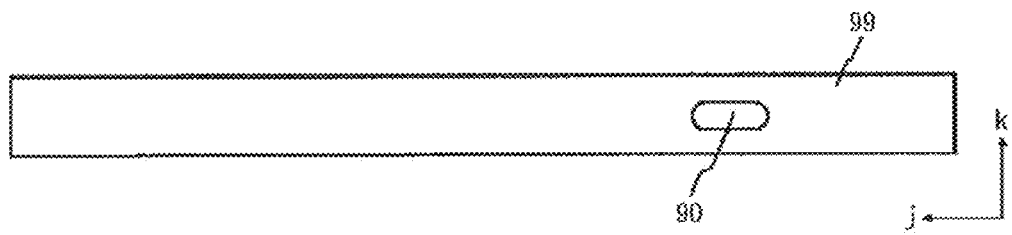
FIG. 86 is a cross-sectional view illustrating an embodiment of an antenna.

The wireless communication device 90 may be positioned on a variety of objects. The wireless communication device 90 may be positioned on an electrical conductive body 99. FIG. 86 is a planar view illustrating an embodiment of the wireless communication device 90. The electrical conductive body 99 is a conductor transmitting electricity. Examples of the material of the electrical conductive body 99 may include metal, highly doped semiconductor, conductive plastic, and liquid including ions. The electrical conductive body 99 may include a non-conductive layer that does not transmit electricity on its surface. The electricity-transmitting section and the non-conductive layer may include a common element. For example, the electrical conductive body 99 including aluminum may include a non-conductive layer of aluminum oxide on its surface. The electricity-transmitting section and the non-conductive layer may include different elements.

The shape of the electrical conductive body 99 is not limited to a flat plate and may include a three-dimensional shape such as a box shape. Examples of the three-dimensional shape of the electrical conductive body 99 include a rectangular parallelepiped and a cylinder. Examples of the three-dimensional shape may include a partially-recessed shape, a partially-penetrated shape, and a partially-protruding shape. For example, the electrical conductive body 99 may have an annular (torus) shape.

The electrical conductive body 99 includes an upper surface 99A on which the wireless communication device 90 may be rested. The upper surface 99A may extend all over the electrical conductive body 99. The upper surface 99A may be a part of the electrical conductive body 99. The surface integral of the upper surface 99A may be larger than that of the wireless communication device 90. The wireless communication device 90 may be placed on the upper surface 99A of the electrical conductive body 99. The surface integral of the upper surface 99A may be narrower than that of the wireless communication device 90. A part of the wireless communication device 90 may be placed on the upper surface 99A of the electrical conductive body 99. The wireless communication device 90 may be placed in various orientations on the upper surface 99A of the electrical conductive body 99. The wireless communication device 90 may be placed in any orientation. The wireless communication device 90 may be fixed as appropriate by a retainer on the upper surface 99A of the electrical conductive body 99. Examples of the retainer include those for surface fixing, such as double-sided tape and adhesive. The examples of the retainer include those for point fixing, such as screw and nail.

The upper surface 99A of the electrical conductive body 99 may include a section extending in the j direction. The section extending in the j direction has a length along the j direction longer than the length along the k direction. The j direction and the k direction are orthogonal to each other. The j direction is a direction in which the electrical conductive body 99 extends lengthwise. The k direction is the direction in which the length of the electrical conductive body 99 is shorter than the j direction. The wireless communication device 90 may be placed on the upper surface 99A such that the x direction extends in the j direction. The wireless communication device 90 may be placed on the upper surface 99A of the electrical conductive body 99 to be aligned with the x direction in which the first conductor 31 and the second conductor 32 are arranged. When the wireless communication device 90 is positioned on the electrical conductive body 99, the first antenna 60 may be electromagnetically coupled to the electrical conductive body 99. In the fourth conductor 50 of the first antenna 60, the second current flows along the x direction. In the electrical conductive body 99 electromagnetically coupled to the first antenna 60, current is induced by the second current. When the x direction of the first antenna 60 is aligned with the j direction of the electrical conductive body 99, current flowing along the j direction increases in the electrical conductive body 99. When the x direction of the first antenna 60 is aligned with the j direction of the electrical conductive body 99, radiation by induced current increases in the electrical conductive body 99. The angle of the x direction relative to the j direction may be equal to or smaller than 45 degrees.

The ground conductor 811 of the wireless communication device 90 is spaced apart from the electrical conductive body 99. The ground conductor 811 is spaced apart from the electrical conductive body 99. The wireless communication device 90 may be placed on the upper surface 99A such that the direction along the long side of the upper surface 99A is aligned with the x direction in which the first conductor 31 and the second conductor 32 are arranged. Examples of the shape of the upper surface 99A may include a rhombus shape and a circular shape, in addition to a quadrature surface. The electrical conductive body 99 may include a rhombus-shaped surface. This rhombus-shaped surface may be the upper surface 99A on which the wireless communication device 90 is rested. The wireless communication device 90 may be placed on the upper surface 99A such that the direction along the longer diagonal line of the upper surface 99A is aligned with the x direction in which the first conductor 31 and the second conductor 32 are arranged. The upper surface 99A is not necessarily flat. The upper surface 99A may include protrusions and depressions. The upper surface 99A may include a curved surface. The curved surface includes a ruled surface (ruled surface). The curved surface includes a columnar surface.

The electrical conductive body 99 extends along the xy plane. The electrical conductive body 99 may have a length along the x direction longer than the length along the y direction. The length along the y direction of the electrical conductive body 99 may be shorter than a half of the wavelength $\lambda_c$ at the operating frequency $f_c$ of the third antenna 97. The wireless communication device 90 may be positioned on the electrical conductive body 99. The electrical conductive body 99 is positioned away from the fourth conductor 50 in the z direction. The length along the x direction of the electrical conductive body 99 is longer than the fourth conductor 50. The electrical conductive body 99 has the surface integral in the xy plane larger than the fourth conductor 50. The electrical conductive body 99 is positioned away from the ground conductor 811 in the z direction. The length along the x direction of the electrical conductive body 99 is longer than the ground conductor 811. The surface integral in the xy plane of the electrical conductive body 99 is larger than the ground conductor 811.

The wireless communication device 90 may be placed on the electrical conductive body 99 in such an orientation that the x direction in which the first conductor 31 and the second conductor 32 are arranged is aligned with the direction in which the electrical conductive body 99 extends lengthwise. In other words, the wireless communication device 90 may be placed on the electrical conductive body 99 in such an orientation that the direction in which current of the first antenna 60 flows and the direction in which the electrical conductive body 99 extends lengthwise are aligned in the xy plane.

In the wireless communication device 90, the first antenna 60 or the second antenna 70 may be installed at an end in the extending direction of the electrical conductive body 99. In the wireless communication device 90, the first antenna 60 or the second antenna 70 may be installed between both ends in the extending direction of the electrical conductive body 99, for example, in the vicinity of the center.

In the first antenna 60, variation in resonance frequency is small because of the conductor on the circuit board 81 side. The wireless communication device 90 has the first antenna 60 and thereby can reduce the effect from an external environment.

In the wireless communication device 90, the ground conductor 811 may be capacitively coupled to the electrical conductive body 99. The wireless communication device 90 has a section extending outward from the third antenna 97 in the electrical conductive body 99, thereby improving the gain compared with the first antenna 60.

Figure 87:
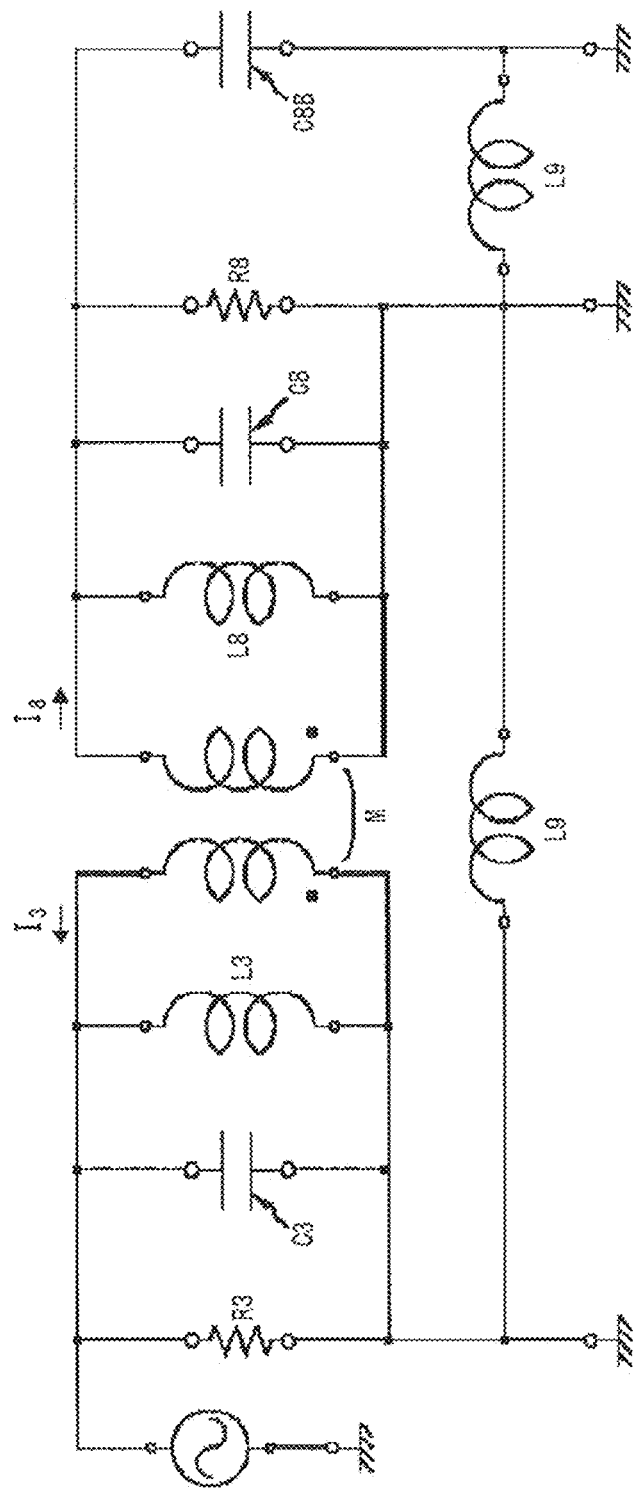
FIG. 87 is a schematic diagram illustrating a circuit of a wireless communication device.
Figure 88:
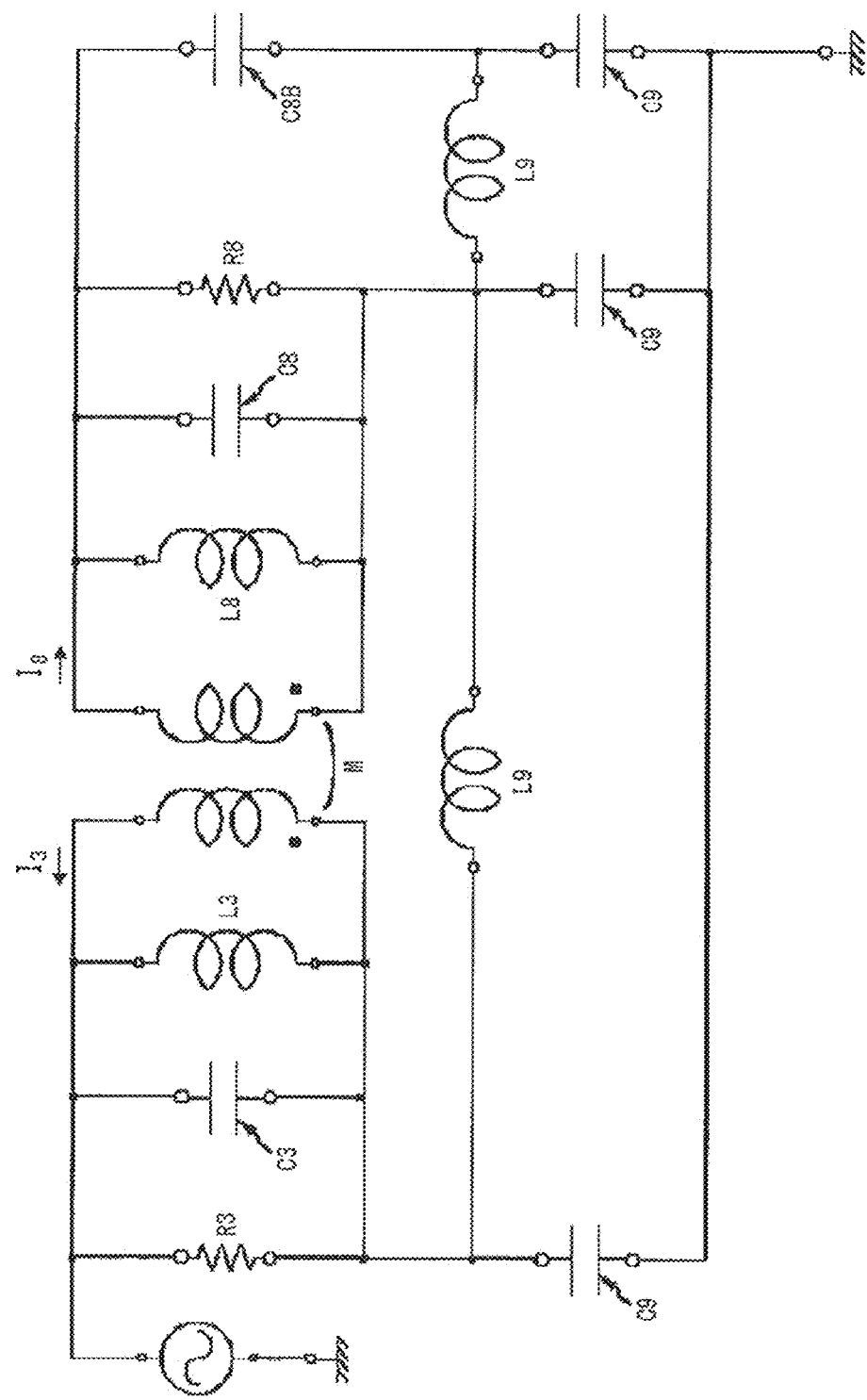
FIG. 88 is a schematic diagram illustrating a circuit of a wireless communication device.

In the wireless communication device 90, the resonant circuit in the air may differ from the resonant circuit on the electrical conductive body 99. FIG. 87 illustrates a schematic circuit of a resonant structure formed in the air. FIG. 88 illustrates a schematic circuit of a resonant structure formed on the electrical conductive body 99. L3 is inductance of the resonator 10, L8 is inductance of the eighth conductor 961, L9 is inductance of the electrical conductive body 99, and M is mutual inductance of L3 and L8. C3 is capacitance of the third conductor 40, C4 is capacitance of the fourth conductor 50, C8 is capacitance of the eighth conductor 961, C8B is capacitance of the eighth conductor 961 and the battery 91, and C9 is capacitance of the electrical conductive body 99 and the ground conductor 811. R3 is radiation resistance of the resonator 10, and R8 is radiation resistance of the eighth conductor 961. The operating frequency of the resonator 10 is lower than the resonance frequency of the eighth conductor. In the wireless communication device 90 in the air, the ground conductor 811 functions as chassis ground. In the wireless communication device 90, the fourth conductor 50 is capacitively coupled to the electrical conductive body 99. In the wireless communication device 90 on the electrical conductive body 99, the electrical conductive body 99 functions as substantial chassis ground.

In a plurality of embodiments, the wireless communication device 90 has the eighth conductor 961. This eighth conductor 961 is electromagnetically coupled to the first antenna 60 and capacitively coupled to the fourth conductor 50. The capacitance C8B by capacitive coupling is increased whereby a higher operating frequency is achieved when the wireless communication device 90 is placed from the air onto the electrical conductive body 99. The mutual inductance M by electromagnetic coupling is increased whereby a lower operating frequency is achieved when the wireless communication device 90 is placed from the air onto the electrical conductive body 99. The balance between the capacitance C8B and the mutual inductance M is changed whereby variation in operating frequency can be adjusted when the wireless communication device 90 is placed from the air onto the electrical conductive body 99. The balance between the capacitance C8B and the mutual inductance M is changed whereby variation in operating frequency can be reduced when the wireless communication device 90 is placed from the air onto the electrical conductive body 99.

The wireless communication device 90 has the eighth conductor 961 electromagnetically coupled to the third conductor 40 and capacitively coupled to the fourth conductor 50. Having such an eighth conductor 961, the wireless communication device 90 can adjust variation in operating frequency when placed from the air onto the electrical conductive body 99. Having such an eighth conductor 961, the wireless communication device 90 can reduce variation in operating frequency when placed from the air onto the electrical conductive body 99.

Similarly, in the wireless communication device 90 that does not include the eighth conductor 961, the ground conductor 811 functions as chassis ground, in the air. Similarly, in the wireless communication device 90 that does not include the eighth conductor 961, the electrical conductive body 99 functions as substantial chassis ground, on the electrical conductive body 99. A resonant structure including the resonator 10 can oscillate even when chassis ground is changed. This corresponds to that the resonator 10 including the reference potential layer 51 and the resonator 10 including no reference potential layer 51 can oscillate.

The wireless communication device 90 may include the electrical conductive body 99 in the manner described above.

At least one of the first case 95 and the second case 96 of the wireless communication device 90 forms a main body 95M and an attachment 95H. The attachment 95H attaches the wireless communication device 90 to a living body 11. The attachment 95H may attach the wireless communication device 90 to a target wearing part of the living body 11. The wearing part may be, for example, head, arm, torso, leg, and finger of the living body 11.

The attachment 95H may allow the contained fourth conductor 50 to be opposed to the living body 11. The attachment 95H may bring the electrical conductive body 99 included in the wireless communication device 90 into contact with the living body 11. The attachment 95H may allow the fourth conductor 50 to be opposed to the living body 11 with the electrical conductive body 99 interposed therebetween. The electrical conductive body 99 may have an elongated shape, and the attachment 95H may bring the electrical conductive body 99 into contact with the living body 11 such that the direction in which the electrical conductive body 99 extends is along the living body 11.

The electrical conductive body 99 may be provided exclusively for radio radiation. The electrical conductive body 99 may also double as an electrical conductive line 99L such as a power supply line and an electrical signal transmission line.

A tenth attachment that is the attachment 95H in the first wireless communication device 901 of the communication system 903 attaches the first wireless communication device 901 including a tenth antenna such that an eleventh axis of the tenth antenna of the first wireless communication device 901 is oriented in the circumferential direction of the axis of the wearing part of the living body 11. The eleventh axis is the first axis in the tenth antenna. A twentieth attachment that is the attachment 95H in the second wireless communication device 902 of the communication system 903 attaches the second wireless communication device 902 including a twentieth antenna such that a twenty-first axis of the twentieth antenna of the second wireless communication device 902 is oriented in the circumferential direction of the axis of the wearing part of the living body 11. The twenty-first axis is the first axis in the twentieth antenna.

In a configuration in which a target wearing part is head or torso, the axis of the wearing part is substantially parallel to the vertical direction of the trans-axial plane. In a configuration in which a target wearing part is arm, the axis of the wearing part is substantially parallel to the longitudinal direction of the arm. In a configuration in which a target wearing part is leg, the axis of the wearing part is substantially parallel to the longitudinal direction of the leg. In a configuration in which a wearing part is finger, the axis of the wearing part is substantially parallel to the longitudinal direction of the finger.

A plurality of embodiments to which more specific manners of the wireless communication device 90 described above are applied will be described below.

(Earphone)

Figure 94:
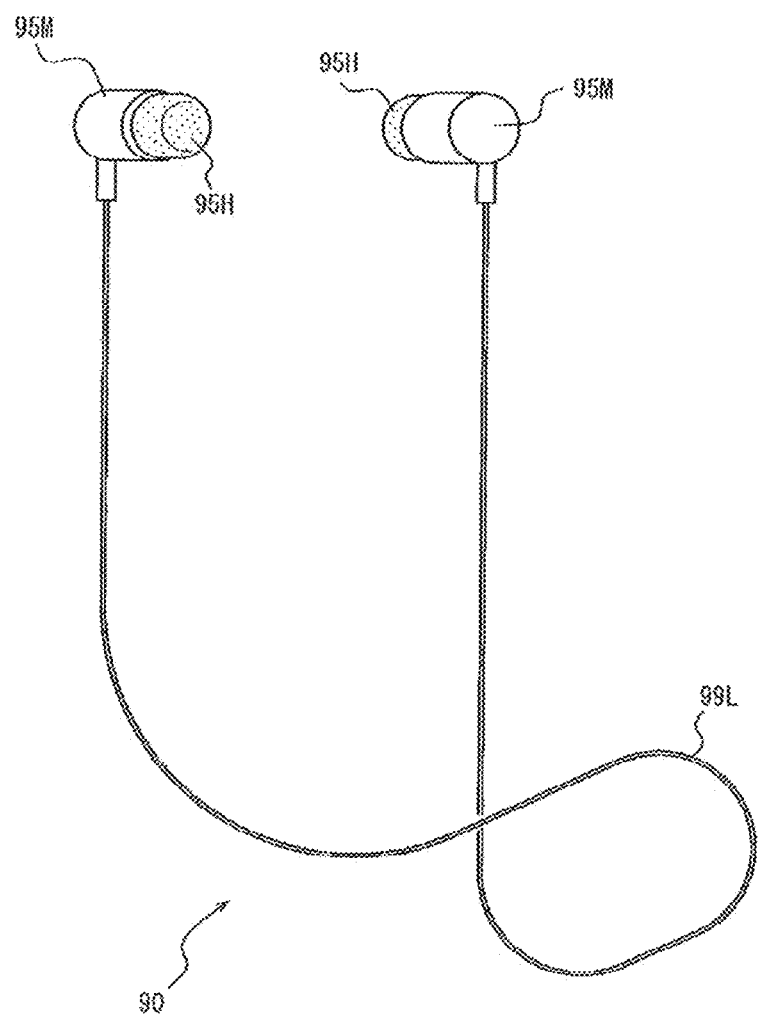
FIG. 94 is an external view illustrating an embodiment of a wireless communication device applied to an earphone.
Figure 95:
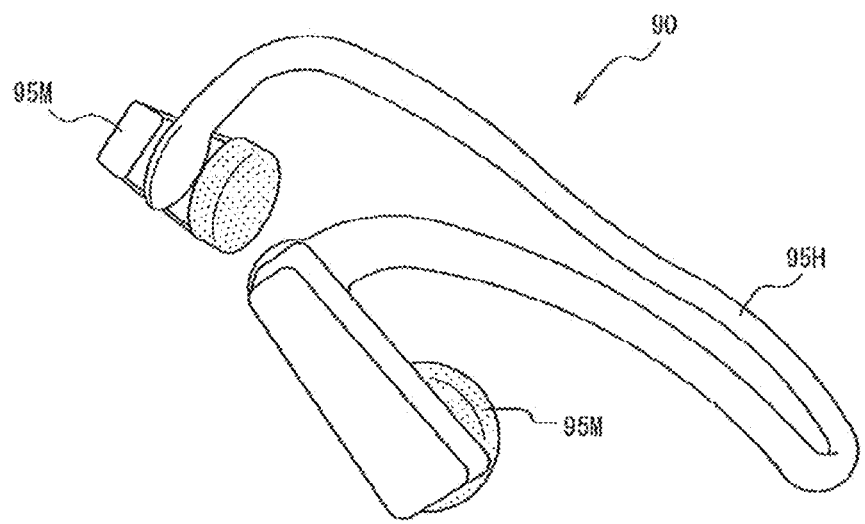
FIG. 95 is an external view illustrating an embodiment of a wireless communication device applied to an earphone.
Figure 96:
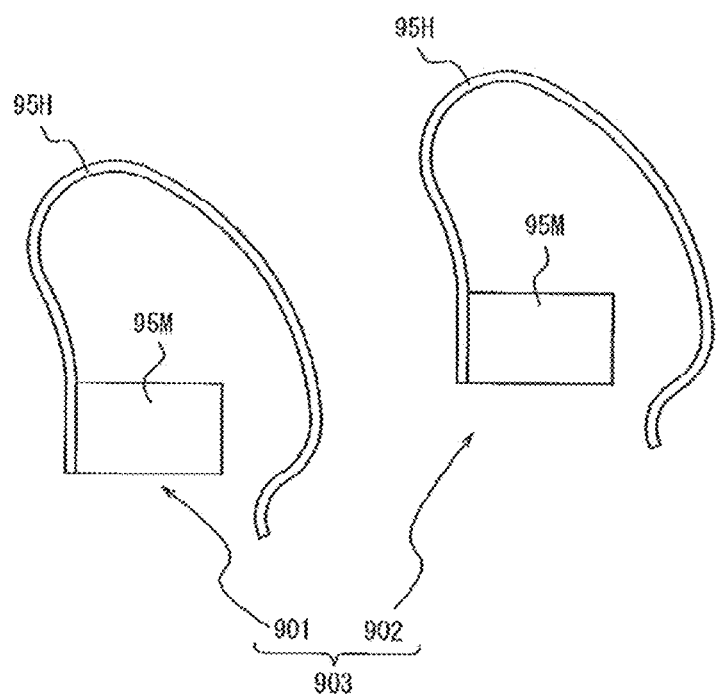
FIG. 96 is an external view illustrating an embodiment of a communication system applied to an earphone.

As illustrated in FIGS. 92 to 95, the wireless communication device 90 is, for example, an earphone. As illustrated in FIG. 96, the earphone may be embodied as the communication system 903 including the first wireless communication device 901 and the second wireless communication device 902. The attachment 95H may attach the wireless communication devices 90, 901, and 902 to the head of the living body 11. The attachment 95H may place the output device 92' of the wireless communication device 90 in the vicinity of the external auditory meatus of the living body 11.

As illustrated in FIGS. 92, 93, 94, and 95, the earphone may be, for example, any of a clip type, an inner ear type, a canal type, and a neck band type. In a configuration of a clip type, the attachment 95H is shaped like a clip engaged with helix. In a configuration of an inner ear type, the attachment 95H has a shape engaged with tragus of cavum conchae. In a configuration of a canal type, the attachment 95H is fitted in the ear canal. In a configuration of a neck band type attachment 95H, the neck band shape extends through the back of the head and across the head or the neck.

Figure 92:
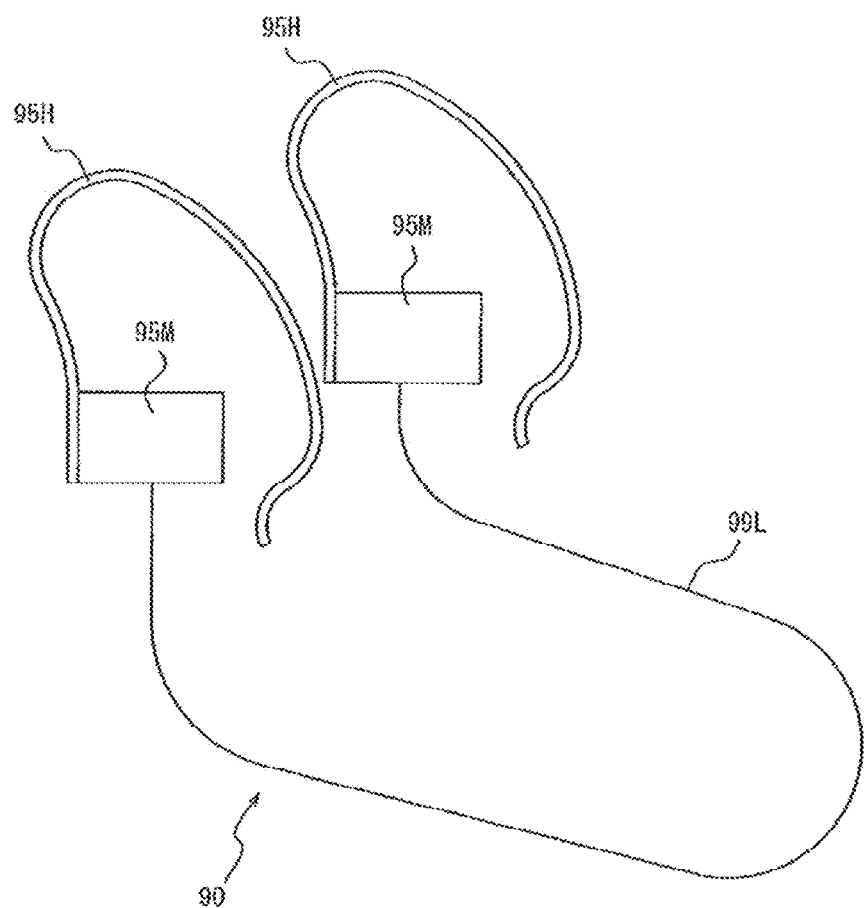
FIG. 92 is an external view illustrating an embodiment of a wireless communication device applied to an earphone.
Figure 93:
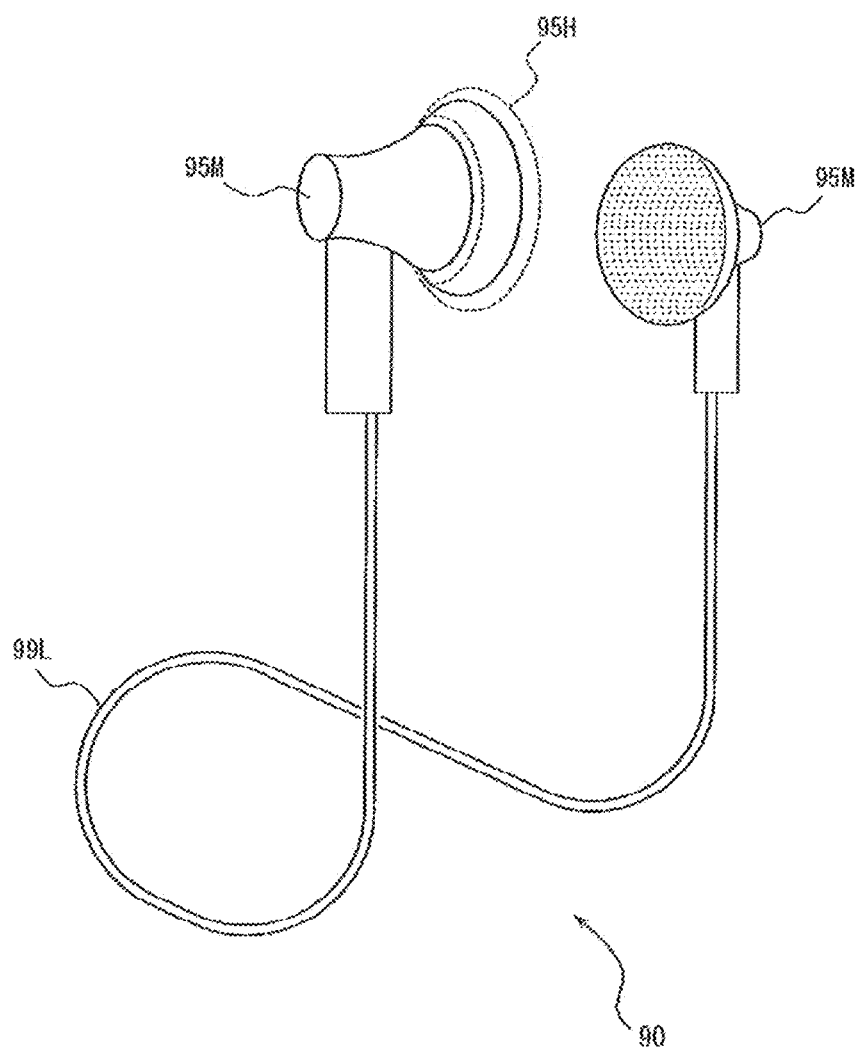
FIG. 93 is an external view illustrating an embodiment of a wireless communication device applied to an earphone.

As illustrated in FIGS. 92 to 94, in a configuration in which the wireless communication device 90 is a clip type, an inner ear type, and a canal type, the electrical conductive body 99 may also double as the electrical conductive line 99L that can connect between the respective output devices 92' of both ears. As illustrated in FIG. 95, in a configuration in which the wireless communication device 90 is a neck band type, the electrical conductive body 99 may also double as an electrical conductive line in the attachment 95H, or the electrical conductive body 99 may be a conductor exclusively for radio wave radiation juxtaposed to the attachment 95H.

As illustrated in FIG. 96, in the communication system 903 as an earphone, the tenth attachment 95H attaches the first wireless communication device 901 in a certain attitude to the ear. In the certain attitude, the eleventh axis of the tenth antenna of the first wireless communication device 901 is parallel to the vertical direction of the trans-axial plane. Similarly, the twentieth attachment 95H attaches the second wireless communication device 902 in a certain attitude to the ear different from that for the first wireless communication device 901. In the certain attitude, the twenty-first axis of the twentieth antenna of the second wireless communication device 902 is parallel to the vertical direction of the trans-axial plane.

The wireless communication device 90 and the communication system 903 as an earphone communicate with the electronic device 12 to receive a signal of at least one of voice and music by radio. The wireless communication device 90 and the communication system 903 output, from the output device 92', sound and the like corresponding to the received signal.

The wireless communication device 90 and the communication system 903 as an earphone may convert the received signal to voice in another language and output the voice from the output device 92'. In a configuration in which a plurality of output devices 92' are disposed on right and left different ears, the output device 92' in the vicinity of one ear may output the converted voice and the output device 92' for the other ear may output unconverted voice, for example.

The wireless communication device 90 and the communication system 903 as an earphone may output sound and the like corresponding to the received signal only from the output device 92' in the vicinity of one of the ears. The output of sound and the like from the output device 92' in the vicinity of the other ear may be stopped. The output device 92' in the vicinity of the other ear may output surrounding environmental sound. The environmental sound may be detected by a sound sensor.

The wireless communication device 90 and the communication system 903 as an earphone may receive an image signal from the electronic device 12. When the image corresponding to the image signal is sign language, the controller 94 may convert the sign language to voice. The converted voice may be output from the output device 92'.

The wireless communication device 90 and the communication system 903 as an earphone may receive a control signal from the electronic device 12. The control signal may be, for example, a command to change sound volume and sound quality of the output device 92'. The controller 94 may control the output device 92' based on the received control signal.

Figure 97:
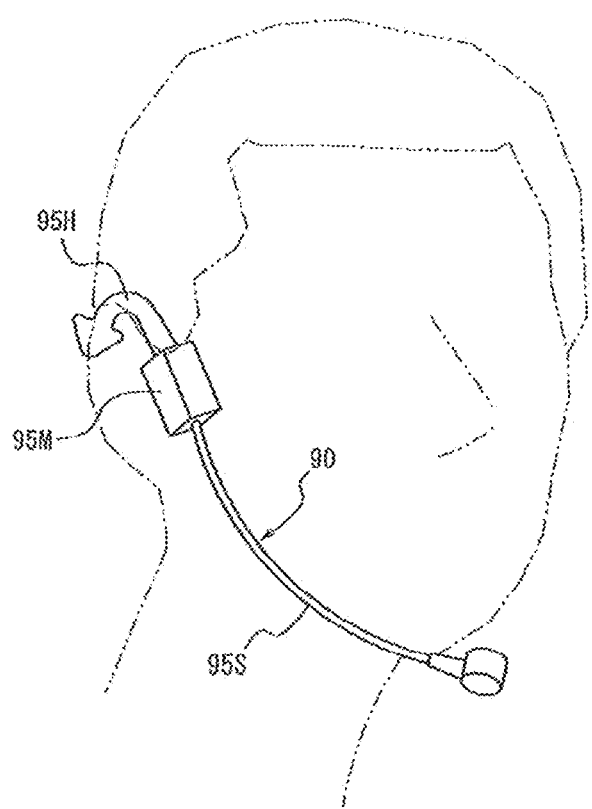
FIG. 97 is an external view illustrating an embodiment of a communication system applied to a headset.

The wireless communication device 90 and the communication system 903 as an earphone transmit, to the electronic device 12, a detection result such as sound or biological data detected by the sensor 92. The earphone detecting sound is known as a headset. As illustrated in FIG. 97, the wireless communication device 90 that is a headset has a support part 95S to place the sensor 92 detecting sound in the vicinity of the mouth of the living body 11 when attached to the living body 11. In such a configuration, the electrical conductive body 99 may also double as the electrical conductive line 99L in the support part 95S or may be a conductor exclusively for electromagnetic radiation juxtaposed to the support part 95S.

In the wireless communication device 90 and the communication system 903 as an earphone, a signal such as sound received by any one of a plurality of wireless communication modules 80 may be transferred to another wireless communication module 80.

(Biological Data Acquisition System)

The wireless communication device 90 is, for example, a data detecting terminal that constitutes a biological data acquisition system together with the electronic device 12 that is a management terminal. The wireless communication device 90 may allow the sensor 92 to detect biological data of the wearing living body 11. The wireless communication device 90 may transmit the detected biological data to the electronic device 12. The electronic device 12 may be dedicated hardware executing a variety of functions or a general-purpose mobile terminal or personal computer loaded with an application executing the functions. The electronic device 12 may store the received biological data into a database. The electronic device 12 may analyze the biological data stored and accumulated. The electronic device 12 may manage biological data received from a plurality of wireless communication devices 90, for each wireless communication device 90.

In the wireless communication device 90 as a data detecting terminal, the attachment 95H may attach the wireless communication device 90 to any one of the head, arm, torso, leg, and finger of a living body. The attachment 95H may bring the sensor 92 of the wireless communication device 90 in proximity to the living body 11.

(Animal Monitoring Device)

The wireless communication device 90 is, for example, an animal monitoring device monitoring the behavior of pet animals and livestock animals. The wireless communication device 90 may allow the sensor 92 to detect biological data of, for example, a wearing pet animal. The wireless communication device 90 may transmit the detected biological data to the electronic device 12 that executes a wide variety of functions for monitoring animals.

The electronic device 12 may be dedicated hardware executing a variety of functions or a general-purpose mobile terminal or personal computer loaded with an application executing the functions. The electronic device may store the received biological data into a database. The electronic device 12 may analyze the biological data stored and accumulated. The electronic device 12 may manage biological data received from a plurality of wireless communication devices 90, for each wireless communication device 90.

The electronic device 12 may have a function of calling a pet animal and the like. When the operator operates the electronic device 12 to call a pet animal and the like, the electronic device 12 may transmit a calling signal to the wireless communication device 90. When a calling signal is received, the wireless communication device 90 may output, from the output device 92', sound for calling the animal wearing the wireless communication device 90 or pattern vibration for calling.

The wireless communication device 90 having a configuration described above includes: an antenna 60, 70 including a first conductor 31 and a second conductor 32, at least one third conductor 40, a fourth conductor 50 extending in the first axis, and a feeding line 61, 72 connected to any one of at least one third conductor 40, the first conductor 31 and the second conductor 32 being capacitively connected to each other through the third conductor 40; and an attachment 95H configured to allow the fourth conductor 50 to be opposed to the living body 11. With such a configuration, the wireless communication device 90 serves as an artificial magnetic conductor having a ground conductor. Thus, the wireless communication device 90 is less influenced by a conductive body when emitting electromagnetic waves even when the antenna 60, 70 is placed in the vicinity of a conductive body such as a living body 11. The wireless communication device 90 therefore improves the intensity of transmission/reception of electromagnetic waves by the antenna 60, 70 and improves the quality of communication. In this way, the wireless communication device 90 improves the availability of wireless communication techniques using the antenna 60, 70 placed in the vicinity of a conductive body such as a living body 11.

In the wireless communication device 90, the fourth conductor 50 is opposed to the living body 11 with the electrical conductive body 99 interposed therebetween. With such a configuration, the wireless communication device 90 can reduce absorption of electromagnetic waves into a living body and achieves at least one of improvement in at least one of communication distance and transmission speed, and reduction in transmission power. The wireless communication device 90 reduces absorption of electromagnetic waves into a living body and therefore can reduce the influence of exposing a living body 11 to electromagnetic waves.

In the wireless communication device 90, the first axis is along the direction in which the electrical conductive body 99 extends. With such a configuration, the wireless communication device 90 can increase radiation by induced current, improves the intensity of transmission/reception of electromagnetic waves by the antenna 60, 70, and improves the quality of communication more.

In the communication system 903, the tenth attachment 95H attaches the tenth antenna to the living body 11 such that the eleventh axis of the tenth antenna is oriented in the circumferential direction of the axis of the wearing part of the living body 11, and the twentieth attachment 95H attaches the twentieth antenna to the living body 11 such that the twenty-first axis of the twentieth antenna is oriented in the circumferential direction of the axis of the wearing part of the living body 11. With such an arrangement of the tenth antenna and the twentieth antenna, the polarization component of the antenna relative to the direction vertical to the living body 11 is oriented in the direction vertical to the axis of the wearing part, so that the electromagnetic wave easily propagates around the circumferential direction. With the above configuration, the communication system 903 can improve the intensity of transmission/reception of electromagnetic waves between the first wireless communication device 901 and the second wireless communication device 902.

The configuration according to the present disclosure is not limited to the embodiments described above and is susceptible to various modifications and changes. For example, the functions included in the components may be rearranged without logical contradiction, or a plurality of components may be combined into one or may be divided.

The drawings that illustrate the configurations according to the present disclosure are schematic. The dimensional ratio and the like on the drawings does not necessarily match the actual one.

In the present disclosure, the notation such as "first", "second", and "third" is an example of the identifier for distinguishing the configuration. The configurations distinguished by the notation such as "first" and "second" in the present disclosure may have the numerals interchangeable. For example, the identifiers "first" and "second" of the first frequency and the second frequency are interchangeable. The identifiers are interchanged simultaneously. The configurations are distinguished even after the identifiers are interchanged. The identifiers may be deleted. The configuration with the identifier deleted is distinguished by a reference sign. For example, the first conductor 31 may be denoted as conductor 31. The notation of identifiers such as "first" and "second" alone should not be used for interpretation of the order of the configurations, the ground that an identifier with a smaller number exists, and the ground that an identifier with a larger number exists. In the present disclosure, although the second conductive layer 42 has the second unit slot 422, the configuration in which the first conductive layer 41 does not have a first unit slot is intended to be embraced.

The invention claimed is:

1. A wireless communication device wearable on a living body, comprising:
   an antenna including
      a base,
      a first conductor and a second conductor supported by the base and opposed to each other in a first axis, at least one third conductor supported by the base, positioned between the first conductor and the second conductor, and extending in the first axis, a fourth conductor supported by the base, opposed to the at least one third conductor in a second axis perpendicular to the first axis, connected to the first conductor and the second conductor, and extending in the first axis, and a feeding line electromagnetically connected to the at least one third conductor, wherein the first conductor and the second conductor are capacitively connected to each other through the at least one third conductor; and an attachment configured to allow the fourth conductor to be opposed to the living body, wherein the base includes a cavity between the at least one third conductor and the fourth conductor in the second axis.

2. The wireless communication device according to claim 1, further comprising an electrical conductive body configured to be brought into contact with the living body, wherein the fourth conductor is opposed to the living body with the electrical conductive body interposed therebetween.

3. The wireless communication device according to claim 2, wherein the attachment is configured to bring the electrical conductive body into contact with the living body such that a direction in which the electrical conductive body extends is along the living body, and the first axis is along the direction in which the electrical conductive body extends.

4. The wireless communication device according to claim 1, further comprising:

a further antenna including a further first conductor and a further second conductor opposed to each other in a further first axis, at least one further third conductor positioned between the further first conductor and the further second conductor and extending in the further first axis, a further fourth conductor connected to the further first conductor and the further second conductor and extending in the further first axis, and a further feeding line electromagnetically connected to the at least one further third conductor, wherein the further first conductor and the further second conductor are capacitively connected to each other through the at least one further third conductor; and a further attachment configured to allow the further fourth conductor to be opposed to the living body.

5. The wireless communication device according to claim 1, wherein the base includes a ceramic material or a resin material.

6. The wireless communication device according to claim 1, wherein the at least one third conductor includes a first conductive layer on the base, and a second conductive layer in the base between the first conductive layer and the fourth conductor.

7. A communication system comprising: a first wireless communication device; and a second wireless communication device, the first wireless communication device comprising:

an antenna including a base, a first conductor and a second conductor supported by the base and opposed to each other in a first axis, at least one third conductor supported by the base, positioned between the first conductor and the second conductor, and extending in the first axis, a fourth conductor supported by the base, opposed to the at least one third conductor in a second axis perpendicular to the first axis, connected to the first conductor and the second conductor, and extending in the first axis, and a feeding line electromagnetically connected to the at least one third conductor, wherein the first conductor and the second conductor are capacitively connected to each other through the at least one third conductor; and an attachment configured to attach the first antenna to a living body such that the first axis is oriented in a circumferential direction of an axis of a wearing part of the living body, and the second wireless communication device comprising:

a further antenna including a further first conductor and a further second conductor opposed to each other in a further first axis, at least one further third conductor positioned between the further first conductor and the further second conductor and extending in the further first axis, a further fourth conductor connected to the further first conductor and the further second conductor and extending in the further first axis, and a further feeding line electromagnetically connected to the at least one further third conductor, wherein the further first conductor and the further second conductor are capacitively connected to each other through the at least one further third conductor; and a further attachment configured to attach the further antenna to the living body such that the further first axis is oriented in the circumferential direction of the axis of the wearing part, wherein the base includes a cavity between the at least one third conductor and the fourth conductor in the second axis.

8. The communication system according to claim 7, wherein the wearing part is a head of the living body, and the axis of the wearing part is substantially parallel to a vertical direction of a trans-axial plane.

9. The communication system according to claim 7, wherein the wearing part is an arm of the living body, and the axis of the wearing part is substantially parallel to a longitudinal direction of the arm.

10. The communication system according to claim 7, wherein the wearing part is a torso of the living body, and the axis of the wearing part is substantially parallel to a vertical direction of a trans-axial plane.

11. The communication system according to claim 7, wherein the wearing part is a leg of the living body, and the axis of the wearing part is substantially parallel to a longitudinal direction of the leg.

12. The communication system according to claim 7, wherein the wearing part is a finger of the living body, and the axis of the wearing part is substantially parallel to a longitudinal direction of the finger.

13. The communication system according to claim 7, wherein the base includes a ceramic material or a resin material.

14. The communication system according to claim 7, wherein the at least one third conductor includes
- a first conductive layer on the base, and
- a second conductive layer in the base between the first conductive layer and the fourth conductor.

* * * * *